United States Patent
Kostenich et al.

(10) Patent No.: US 11,827,687 B2
(45) Date of Patent: *Nov. 28, 2023

(54) SYNTHETIC SOMATOSTATIN RECEPTOR LIGANDS

(71) Applicants: TEL HASHOMER MEDICAL RESEARCH INFRASTRUCTURE AND SERVICES LTD., Ramat Gan (IL); RAMOT AT TEL AVIV UNIVERSITY LTD., Tel Aviv (IL)

(72) Inventors: Genady Kostenich, Ramat Gan (IL); Mor Oron-Herman, Ramat Efal (IL); Arie Orenstein, Tel Aviv (IL); Talia Shekhter Zahavi, Petah Tikva (IL); Ehud Gazit, Ramat Hasharon (IL); Yoseph Salitra, Rehovot (IL); Ludmilla Buzhansky, Ariel (IL)

(73) Assignee: TEL HASHOMER MEDICAL RESEARCH INFRASTRUCTURE AND SERVICES LTD., Ramat Gan (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/591,620

(22) Filed: Feb. 3, 2022

(65) Prior Publication Data
US 2022/0162284 A1 May 26, 2022

Related U.S. Application Data

(63) Continuation of application No. 16/914,388, filed on Jun. 28, 2020, now Pat. No. 11,261,230, which is a continuation of application No. 16/357,340, filed on Mar. 19, 2019, now Pat. No. 10,723,780, which is a continuation of application No. 15/509,842, filed as application No. PCT/IB2015/056941 on Sep. 10, 2015, now Pat. No. 10,266,579.

(60) Provisional application No. 62/050,155, filed on Sep. 14, 2014, provisional application No. 62/050,153, filed on Sep. 14, 2014.

(51) Int. Cl.
| | |
|---|---|
| *C07K 14/655* | (2006.01) |
| *A61K 38/08* | (2019.01) |
| *A61K 47/62* | (2017.01) |
| *A61K 47/69* | (2017.01) |
| *A61K 38/12* | (2006.01) |
| *A61K 49/00* | (2006.01) |

(52) U.S. Cl.
CPC ............ *C07K 14/655* (2013.01); *A61K 38/08* (2013.01); *A61K 38/12* (2013.01); *A61K 47/62* (2017.08); *A61K 47/6923* (2017.08); *A61K 47/6933* (2017.08); *A61K 47/6937* (2017.08); *A61K 49/0043* (2013.01); *A61K 49/0056* (2013.01); *A61K 49/0093* (2013.01)

(58) Field of Classification Search
None
See application file for complete search history.

(56) References Cited

U.S. PATENT DOCUMENTS

| 5,595,756 A | 1/1997 | Bally et al. |
|---|---|---|
| 6,051,206 A | 4/2000 | Dean et al. |
| 7,700,717 B2 | 4/2010 | Bonasera et al. |
| 2005/0090429 A1 | 4/2005 | Bonasera et al. |

FOREIGN PATENT DOCUMENTS

| GB | 2 241 167 | 8/1991 |
|---|---|---|
| WO | 98/10786 | 3/1998 |
| WO | 1998/010786 | 3/1998 |
| WO | 02/100888 | 12/2002 |
| WO | 2011/117851 | 9/2011 |
| WO | 2012054923 | 4/2012 |
| WO | 2012166923 | 12/2012 |
| WO | 2014004361 | 1/2014 |
| WO | 2014043625 | 3/2014 |

OTHER PUBLICATIONS

Kostenich et al., "Diagnostic targeting of colon cancer using a novel fluorescent somatostatin conjugate in a mouse kenograft model", Int. J. Cancer: 122,2044-2049 (2008).

International Search Report and Written Opinion dated Dec. 13, 2015 in PCT/IB2015/056941 (15 pages).

Jong et al., PEGylation of Oetreotide: I. Separation of Positional Isomers and Stability Against Acylalion by Poly(D,L-lactide-co-glycolide), Pharmaceutical Research, vol. 22, No. 5, May 2005, DOI: 10.1007/s11095-005-2589-4, 736-42.

Capello et al., Anticancer Activity of Targeted Proapoptotic Peptides, The Journal of Nuclear Medicine vol. 47 No. Jan. 1, 2006, 122-29.

Erfani-Jabariana et al.,PEGylation of Octreotide Using an .alpha.,.beta.-unsaturated-.beta.'-mono-sulfone Functionalized PEG Reagent, Iranian Journal of Pharmaceutical Research (2012). 11(3): 747-753.

Andreoli et al., Preparation and evaluation of polyethyleneimine-single walled carbon nanotube conjugates as vectors for pancreatic cancer treatment. J Mater Chem. B 2014;2:4740-4747.

Falb et al., A bicyclic and hsst2 selective somatostatin analogue: design, synthesis, conformational analysis and binding. Bioorg Med Chem. Dec. 2001;9(12):3255-3264.

(Continued)

*Primary Examiner* — Thomas S Heard
(74) *Attorney, Agent, or Firm* — JMB Davis Ben-David

(57) ABSTRACT

Disclosed are Somatostatin receptor ligands comprising a peptide moiety, pharmaceutical compositions and uses thereof. Disclosed are also synthetic Somatostatin receptor ligands comprising a cyclic peptide moiety and an active agent moiety covalently bonded to the cyclic peptide moiety through a nitrogen atom of a side chain functional group of an internal residue of the cyclic peptide moiety, pharmaceutical compositions and uses thereof. Disclosed are also synthetic Somatostatin receptor ligands comprising a cyclic peptide moiety and a nanoparticle active agent moiety covalently bonded to the cyclic peptide moiety, pharmaceutical compositions and uses thereof.

13 Claims, 10 Drawing Sheets

Specification includes a Sequence Listing.

(56) References Cited

OTHER PUBLICATIONS

Gazal et al., Synthesis of novel protected Nalpha(omega-thioalkyl) amino acid building units and their incorporation in backbone cyclic disulfide and thioetheric bridged peptides. J Pept Res. Dec. 2001;58(6):527-539.

Murthy, Nanoparticles in modern medicine: state of the art and future challenges. Int J Nanomedicine. 2007;2(2):129-141.

Tai et al., Folding Graft Copolymer with Pedant Drug Segment for Co-Delivery of Anticancer Drugs. Biomaterials. Aug. 2014;35(25):7194-7203.

Zugazagoilia et al, Current Challenges in Cancer Treatment, Clinical Therapies, vol. 38, (2016), pp. 1551-1566 (year 2016).

Spron et al. "Chemoprevention of Cancer," Carcinogenesis, vol. 21 (2000), 525-530 (Year 2000).

*There is an ATG upstream of the Xbz i site

A - 150228

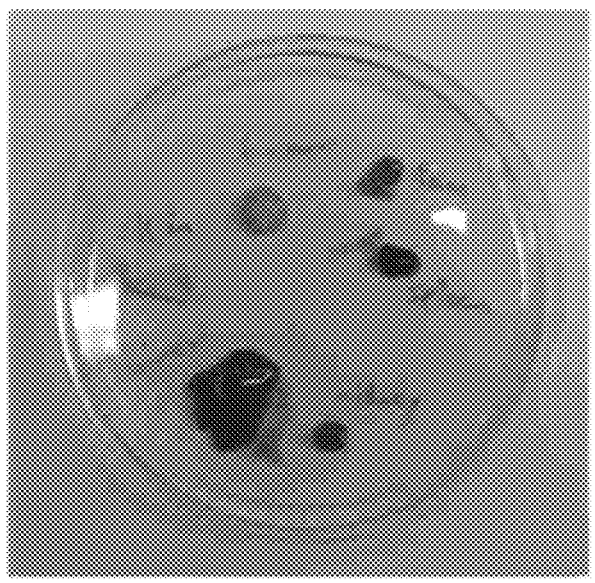
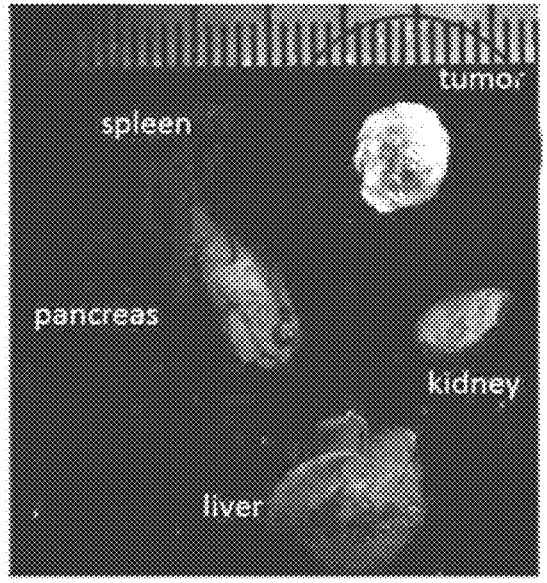
FIG. 7A          FIG. 7B
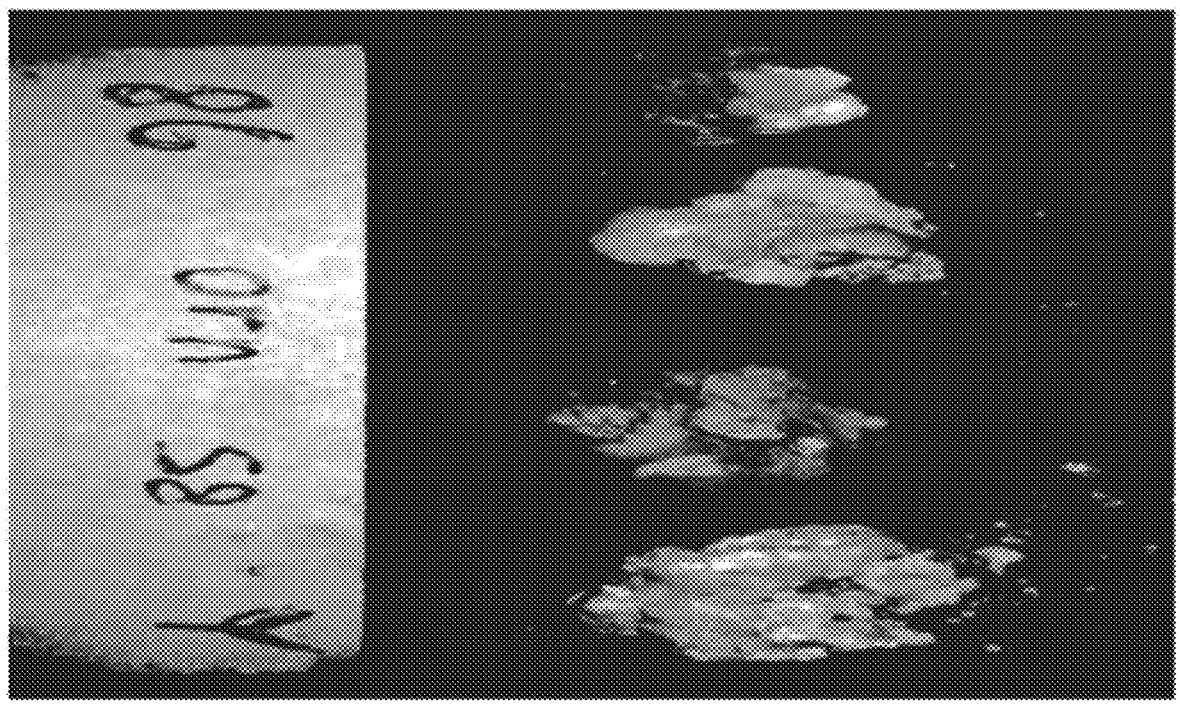
FIG. 8

SYNTHETIC SOMATOSTATIN RECEPTOR LIGANDS

CROSS-REFERENCE TO RELATED APPLICATIONS

This is a Continuation of U.S. patent application Ser. No. 16/914,388 filed Jun. 28, 2020, which is a Continuation of U.S. patent application Ser. No. 16/357,340 filed Mar. 19, 2019 which is a Continuation of U.S. patent application Ser. No. 15/509,842, filed Mar. 8, 2017, which is the US National Stage of International Patent Application No. PCT/IB2015/056941, filed Sep. 10, 2015, which in turn claimed priority to U.S. Provisional Application Nos. 62/050,153 and 62/050,155, both filed 14 Sep. 2014. The foregoing patent applications are incorporated by reference herein in their entirety.

SEQUENCE LISTING

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named "3194_5_3003_SEQ_LIST_ST25", which is 36 kbytes in size, and which was created on Feb. 2, 2022, which is incorporated by reference herein.

FIELD AND BACKGROUND OF THE INVENTION

The invention, in some embodiments, relates to the field of receptor ligands, and more particularly to ligands for Somatostatin Receptors.

Somatostatin is an endogenous protein 116 amino acid residues long (SEQ ID NO:1) that is secreted, inter alia, in the brain, stomach, intestine and pancreatic delta cells which C-terminus is cleaved in vivo to make two circulatory active forms, SST-14 (14 amino acid residues, 103-116; SEQ ID NO:2):

Ala-Gly-Cys-Lys-Asn-Phe-Phe-Trp-Lys-Thr-Phe-Thr-Ser-Cys and SST-28 (28 amino acid residues, 89-116; SEQ ID NO:3):

Ser-Ala-Asn-Ser-Asn-Pro-Ala-Met-Ala-Pro-Arg-Glu-Arg-Lys-(SST-14).

SST-14 and SST-28 are both ligands and agonists for a family of five G-protein coupled 7-transmembrane receptors called Somatostatin Receptors, SSTR1-SSTR5, collectively referred to as SSTRx herein. SSTRx are expressed in cells of healthy tissue and are also overexpressed in some pathological cells, including many different types of cancerous cells.

Both SST-14 and SST-28 act primarily as regulatory hormones by binding to the five SSTRx to be internalized into the cells expressing the SSTRx. As regulatory hormones, endogenous SST-14 and SST-28 are known to regulate other hormones of the endocrine system, affect neurotransmission, affect cell proliferation and inhibit the release of numerous hormones and secretory proteins from cells expressing SSTRx. Specifically, internalization of endogenous SST-14 and SST-28 into a cell expressing SSTRx potentially activates several signaling pathways that induce complex signaling cascades (e.g. inhibition of adenylate cyclase and cAMP production, activation of potassium ion channels, activation of a number of protein phosphatases from different families), the specific effect varying according to the SSTR subtype and the type of tissue type in which the cell is located. Further, a single cell or tissue type (both pathological and non-pathological cells and tissue) typically expresses more than one SSTRx subtype, and the relative proportion of the different SSTRx of a given cell can change over time and as a result of different conditions, including the development stage of the cell, exposure to non-Somatostatin hormones, neuropeptides and other biochemical stimuli.

To date, there exist two synthetic Somatostatin analogues approved for therapeutic use: Octreotide and Lanreotide, both display high-affinity binding to SSTR2, moderate affinity binding to SSTRR3 and SSTR5, and almost no affinity binding to SSTR1 and SSTR4

Lanreotide (commercially available in acetate form as Somatuline® by Ipsen Pharma S.A.S, Paris, France) is a synthetic Somatostatin analogue that is an octopeptide with a six-amino acid residue cyclic portion, having the amino acid residue sequence set forth in SEQ ID NO:4:

Napht-Cys*-Tyr-Trp-Lys-Val-Cys*-Thr where Napht is the alpha amino acid residue —NH—CH($CH_2$—$C_{10}H_7$)—C(O)O— (D-naphthylalanine D-Nal), and the asterisks indicate cyclization by an S—S bond between two cysteine amino acid residues. Lanreotide has been prescribed for treatment of acromegaly and symptoms caused by neuroendocrine tumors, most notably carcinoid syndrome.

Octreotide (commercially available in acetate form as Sandostatin® by Novartis, Basel, Switzerland) is a synthetic Somatostatin analogue that is an octopeptide with a six-amino acid residue cyclic portion, having the amino acid residue sequence set forth in SEQ ID NO:5:

DPhe-Cys*-Phe-DTrp-Lys-Thr-Cys*-Throl where Throl is the beta amino acid residue —NH—CH($CH_2OH$)—CH($CH_3$)—OH (L-threoninol) and the asterisks indicate cyclization by an S—S bond between the two amino acid residues.

Additional synthetic peptide Somatostatin analogues have been disclosed by one of the present Inventors in U.S. Pat. No. 7,700,717. A prominent such analogue (designated 3207) has amino acid residue sequence set forth in SEQ ID NO:6:

DPhe-Cys*-Phe-Trp-DTrp-Lys-Thr-Phe-

GlyS2*-$NH_2$ and the peptide-fluorescent conjugate designated "86" thereof:

FITC-GABA-DPhe-Cys*-Phe-Trp-DTrp-Lys-

Thr-Phe-GlyS2*-$NH_2$ which is also identified herein as "Compound 1", where GlyS2 is the alpha-secondary amino acid residue —N($CH_2CH_2S$—)$CH_2CO$— (glycine with a —$CH_2CH_2S$— moiety added to the terminal amino group, as described in Gazal S et al J Pept Res 2001, 58(6), 527-539; which in the sequence listing is referred to as N-thioethyl Glycine), the asterisks indicate cyclization by a disulfide (S—S) bond between two amino acid residues, and FITC-GABA is a fluorescent active agent made up of the fluorophore FITC (fluorescein isothiocyanate) and the linker GABA (gamma-aminobutyric acid).

It would be useful to have therapeutically-active, stable and receptor-specific somatostatin analogues.

SUMMARY OF THE INVENTION

The invention, in some embodiments, relates to the field of receptor ligands, and more particularly to ligands for Somatostatin Receptors.

The teachings herein may be considered as including at least three aspects that partially overlap:

a first aspect relates to a Somatostatin receptor ligand that comprises a peptide moiety including an amino acid residue sequence set forth as SEQ ID NO:7, which in some embodiments is linear, and in some embodiments is cyclic; and optionally includes an active agent moiety covalently attached thereto;

a second aspect relates to a synthetic Somatostatin receptor ligand that comprises a cyclic peptide moiety with a covalently bonded active agent moiety, an embodiment of which is schematically depicted in FIG. 13; and a third aspect relates to a synthetic Somatostatin receptor ligand that comprises a cyclic peptide moiety with a covalently bonded nanoparticle active agent moiety.

First Aspect

Thus, according to an aspect of some embodiments of the invention, there is provided a Somatostatin receptor ligand, comprising: a peptide moiety including an amino acid residue sequence set forth as SEQ ID NO:7:

-Xxx3-Xxx4-DTrp-Xxx6-Thr-Phe-A wherein:
Xxx3 is selected from the group consisting of Phe and Tyr;
Xxx4 is present or absent and if present is selected from the group consisting of Trp and Phe;
Xxx6 is selected from the group consisting of amino acid residues having a side chain with at least one nitrogen atom;
A is any chemical entity;
and wherein at least one of:
a. Xxx3 is Tyr;
b. Xxx4 is present or absent and if present is Phe; and
c. Xxx6 is other than Lys; and
salts, esters and amides thereof.

According to an aspect of some embodiments of the invention, there is also provided a Somatostatin receptor ligand, comprising: a peptide moiety wherein an arginine amino acid residue is covalently bonded to the N terminus of SEQ ID NO:7 and includes the amino acid sequence set forth in SEQ ID NO:8:

-Arg-Xxx3-Xxx4-DTrp-Xxx6-Thr-Phe-A wherein:
Xxx3 is selected from the group consisting of Phe and Tyr;
Xxx4 is present or absent and if present is selected from the group consisting of Trp and Phe;

Xxx6 is selected from the group consisting of amino acid residues having a side chain with at least one nitrogen atom;
A is any chemical entity
and wherein at least one of:
a. Xxx3 is Tyr;
b. Xxx4 is present or absent and if present is Phe; and
c. Xxx6 is other than Lys; and
salts, esters and amides thereof.

According to an aspect of some embodiments of the invention, there is also provided a Somatostatin receptor ligand, comprising: a peptide moiety including the amino acid sequence set forth in SEQ ID NO:9:

-Xxx1-Xxx2-Xxx3-Xxx4-DTrp-Xxx6-Thr-Phe-A wherein:
Xxx1 is selected from the group consisting of Cys, HCys and DCys;
Xxx2 is present or absent and when present is Arg; and
Xxx3 is selected from the group consisting of Phe and Tyr;
Xxx4 is present or absent and if present is selected from the group consisting of Trp and Phe;
Xxx6 is selected from the group consisting of amino acid residues having a side chain with at least one nitrogen atom; and
A is any chemical entity;
and salts, esters and amides thereof. In some preferred embodiments, Xxx1 is selected from the group consisting of HCys and DCys.

It is important to note that the chemical entity designated "A" in the sequences recited herein (SEQ ID NOS:7, 8, 9 above, as well as in other sequences recited herein) is any suitable chemical entity bonded to complete the valency of the Phe amino acid residue near the C-terminus. The nature of A, as well as the nature of chemical entities bonded to the N-terminal amino acid residue to complete the valency thereof of the sequences recited herein (SEQ ID NOS:7, 8, 9 above, as well as other sequences recited herein) are discussed in greater detail hereinbelow. In some embodiments of the first aspect that are also related to the second and/or third aspects, chemical entity A is Xxx9-A', where Xxx9 is an amino acid residue as described below, and A' is any suitable chemical entity bonded to complete the valency of the Xxx9 amino acid residue. In some preferred embodiments, Xxx9 is a GlyS2 amino acid residue.

Second Aspect

According to a second aspect of some embodiments of the present invention there is also provide a synthetic Somatostatin receptor ligand (an embodiment of which is schematically depicted in FIG. 13), comprising:
a cyclic peptide moiety;
the cyclic peptide moiety consisting of from 6 to 9 amino acid residues, including an N-terminal amino acid residue, a C-terminal amino acid residue and 4, 5, 6 or 7 internal amino acid residues therebetween;
each of the N-terminal amino acid residue and the C-terminal amino acid residue having a sulfur-containing functional group, mutually covalently bonded through a sulfur-sulfur bond, thereby cyclizing the peptide moiety;

wherein at least one of the 4, 5, 6 or 7 the internal amino acid residues includes a side chain functional group having a nitrogen atom; and covalently bonded to the cyclic peptide moiety through the nitrogen atom of the functional group of the internal amino acid residue, an active agent moiety (e.g., in the embodiment depicted in FIG. 13, designated Q bonded to the nitrogen atom N) selected from the group consisting of:

an imaging moiety, a therapeutic moiety, a dye, a fluorescent moiety, a toxin, a chelator, a moiety with a metal atom, a moiety with a radioactive atom, a nanoparticle, an ethylene glycol polymer, photosensitizer, a liposome constituent and a micelle constituent and salts, esters and amides thereof.

In some preferred embodiments of the second aspect, the internal amino acid residue of the cyclic peptide moiety that includes a side chain functional group having a nitrogen atom is Xxx6 as depicted in FIG. 13. In other embodiments, the internal amino acid residue of the cyclic peptide moiety that includes a side chain functional group having a nitrogen atom is different than Xxx6.

Third Aspect

According to a third aspect of some embodiments of the invention, there is also provided a synthetic Somatostatin receptor ligand (an embodiment of which is depicted in FIG. 13), comprising:

a cyclic peptide moiety;
the cyclic peptide moiety consisting of from 6 to 9 amino acid residues, including an N-terminal amino acid residue, a C-terminal amino acid residue and 4, 5, 6 or 7 internal amino acid residues therebetween;
each of the N-terminal amino acid residue and the C-terminal amino acid residue having a sulfur-containing functional group, mutually covalently bonded through a sulfur-sulfur bond, thereby cyclizing the peptide moiety;
optionally wherein at least one of the 4, 5, 6 or 7 the internal amino acid residues includes a side chain functional group having a nitrogen atom; and
covalently bonded to the cyclic peptide moiety, a nanoparticle active agent moiety and salts, esters and amides thereof.

In some embodiments of the third aspect, the nanoparticle active agent moiety is covalently bonded to the nitrogen atom of the side chain of the internal amino acid residue (e.g., the receptor ligand is as depicted in FIG. 13 where the nanoparticle active agent moiety is Q bonded to Xxx6 through the nitrogen atom N). In some such embodiments, the nanoparticle active agent moiety is covalently bonded to the N-terminal amino acid residue of the cyclic peptide moiety (e.g., the receptor ligand is as depicted in FIG. 13 where the nanoparticle active agent moiety is B' bonded to amino acid residue Xxx1. In some such embodiments, the nanoparticle active agent moiety is covalently bonded to the C-terminal amino acid residue of the cyclic peptide moiety (e.g., the receptor ligand is as depicted in FIG. 13 where the nanoparticle active agent moiety is B bonded to amino acid residue Xxx9).

According to an aspect of some embodiments of the invention, there is also provided a pharmaceutical composition comprising: as an active ingredient, at least one (synthetic) Somatostatin receptor ligand according to any one of the aspects (e.g., first, second or third aspects) of the teachings herein; and a pharmaceutically acceptable carrier.

According to an aspect of some embodiments of the invention, there is also provided a method of making a pharmaceutical composition comprising: combining at least one (synthetic) Somatostatin receptor ligand according to any one of the aspects (e.g., first, second or third aspects) of the teachings herein; and a pharmaceutically acceptable carrier.

According to an aspect of some embodiments of the invention, there is also provided the use of a (synthetic) Somatostatin receptor ligand according to any one of the aspects (e.g., first, second or third aspects) of the teachings herein for the treatment of a living organism.

According to an aspect of some embodiments of the invention, there is also provided a method of treating a cell expressing a Somatostatin Receptor comprising: administering at least one (synthetic) Somatostatin receptor ligand according to any one of the aspects (e.g., first, second or third aspects) of the teachings herein to a cell expressing a Somatostatin Receptor, thereby treating the cell.

Unless otherwise defined, all technical and scientific terms used herein have the same meaning as commonly understood by one of ordinary skill in the art to which the invention pertains. In case of conflict, the specification, including definitions, will take precedence.

Amino acids are referred to by the standard three letter code. Amino acids are L-amino acids unless otherwise noted, for example, by addition of the prefix "D". For example, the code Trp refers to L-tryptophan, while the code DTrp refers to D-tryptophan. The code Aib refers to 2-Aminoisobutyric acid. The code Orn refers to Ornithine. The code Lys-Ac refers to acetyllysine. The code HomoLys refers to homolysine. The code HCys refers to homocysteine. The code Napht refers to D-naphthylalanine. The code Throl refers to L-threoninol. The code GlyS2 refers to N-thioethyl Gly amino acid residue (Gazal et al, ibid) as described above.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 4A (left image): Green fluorescence of Compound 1;

FIG. 4B (middle image): Red Fluorescence Protein (RFP) indicating transfection of human SSTR gene;

FIG. 4C (right image) a combined image;

FIG. 5A: show green fluorescence of Compound 1;

FIG. 5B: show combined image of Red Fluorescence Protein (RFP) indicating transfection of human SSTR gene and PTR-86;

FIG. 6A (Control): Native, non transfected cells; FIG. 6B (RFP): SSTR-5 transfected cells without Compound 1; FIG. 6C (PTR86) SSTR-5 overexpressing transfected cells incubated for 1 hr with 500 nM Compound 1;

FIGS. 7A and 7B show a typical ex vivo assessment of compound biodistribution in mice bearing pancreatic BON1 tumor using fluorescence imaging:

FIG. 7A: tissue samples;

FIG. 7B: fluorescence of the tissue samples 24 hrs after IV administration of a compound disclosed herein (excitation 460 nm, emission >500 nm);

FIG. 8 shows fluorescence of gross sections of BON1 tumors 24 hr after IV administration of Compound 1 (top labelled 86), Compound 3 (second from top labelled Orn), Compound 2 (penultimate labelled 58) and Compound 4 (bottom labelled Y) (10 mg/kg);

DESCRIPTION OF SOME EMBODIMENTS OF THE INVENTION

Figure 1:
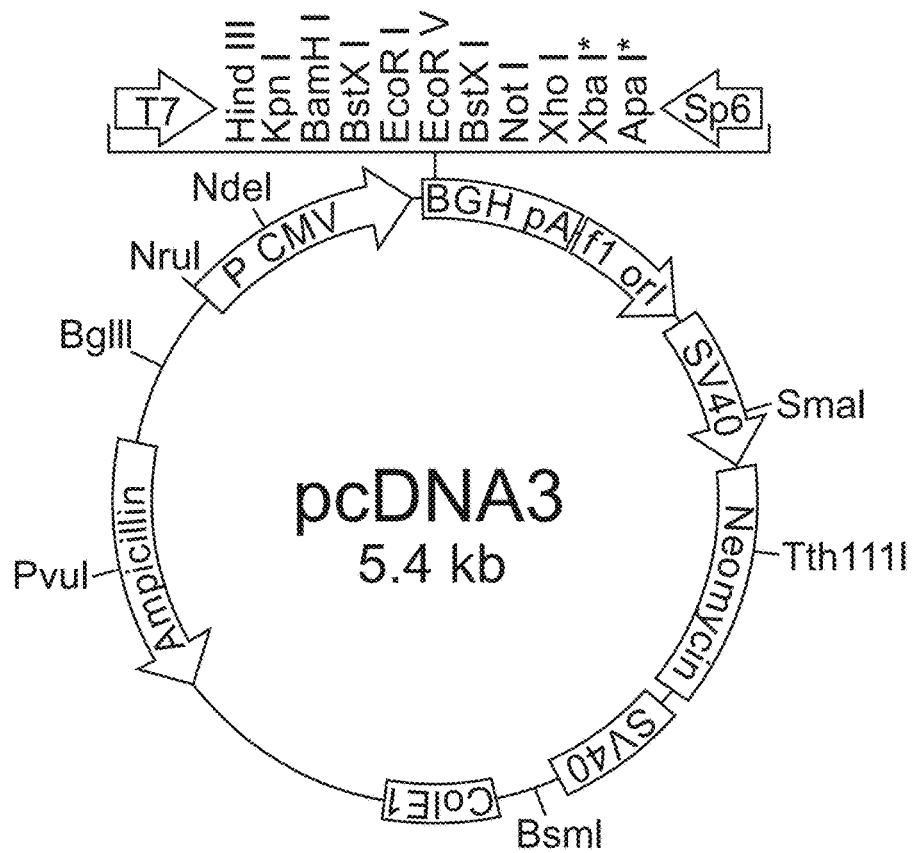
FIG. 1 illustrates the transfection vector and transfection process used for preparing cell lines for evaluating the binding affinity of Somatostatin receptor ligands according to the teachings herein.
Figure 1:
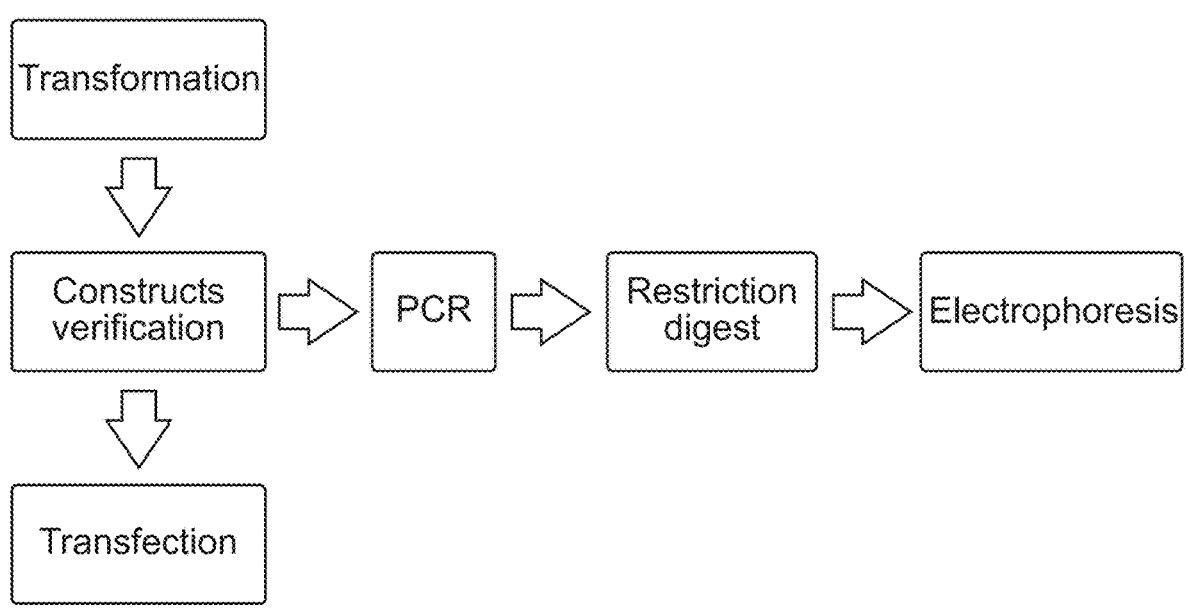

The invention, in some embodiments, relates to the field of receptor ligands, and more particularly to ligands for Somatostatin Receptors.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings and/or the Examples. The invention can be implemented with other embodiments and can be practiced or carried out in various ways. It is also understood that the phraseology and terminology employed herein is for descriptive purpose and should not be regarded as limiting.

In the field of biology, it is known that biological processes in a living organism are regulated by endogenous receptor ligands that bind to an appropriate receptor, thereby affecting cellular processes with which the receptor is involved. The exact effect a given receptor ligand has when binding to a receptor depends on various factors, including whether the receptor ligand is an agonist, antagonist, inverse agonist, partial agonist or co-agonist for the receptor.

Many endogenous receptor ligands are proteins of which a small portion (typically between 3 and 20 amino acid residues long) is the pharmacophore that actually binds to the receptor, typically through one or more of ionic bonds, hydrogen bonds and van der Waals forces. The non-pharmacophore portion of the endogenous receptor ligand defines and fixes the exact conformation of the pharmacophore allowing efficient, specific and/or and selective binding to the receptor. Subtle differences in the structure or conformation of a given receptor or corresponding receptor ligand, for instance, may in some instances change the effect or magnitude of effect triggered by a receptor ligand binding to a receptor. Such differences may be related to side-effects, drug-drug interactions, and why two different organisms of the same species may react to a given synthetic receptor ligand in different ways, an effect that has motivated the need for personalized medicine.

A representative example of such differences is the Somatostatin ligand/receptor system.

Somatostatin Receptors, SSTR1-SSTR5, collectively referred to as SSTRx herein are expressed in cells of healthy tissue:

SSTR1 is expressed in highest levels in the jejunum and stomach;

SSTR2 is expressed in highest levels in the cerebrum and kidney;

SSTR3 is expressed in highest levels in the brain and pancreatic islets;

SSTR4 is expressed in highest levels in the fetal and adult brain and lungs; and SSTR5 is expressed in highest levels in the brain, pituitary gland, pancreas (alpha and gamma cells) as well as in the gastrointestinal tract.

SSTRx are also overexpressed in some pathological cells, including many different types of cancerous cells.

Despite both being SSTRx ligands and agonists, endogenous SST-14 and SST-28 have similar but not identical biological effects, and in some instances even have distinct effects. It is known that the affinity of SST-28 to SSTR5 is substantially greater than that of SST-14 to SSTR5. It has been demonstrated that SST-28 is more potent than SST-14 in blocking insulin release from pancreatic beta cells while SST-14 is more potent in inhibiting glucagon secretion from alpha cell islets of Langerhans. Furthermore, there is some evidence that SST-14 and SST-28 induce opposite changes in voltage-dependent potassium ion currents in cerebral cortical neurons.

Further, the specific in vivo functions of the different SSTR subtypes are still poorly understood, although various studies have demonstrated that different SSTRx may mediate similar (not necessarily identical) or opposing effects. Additionally, the fact that a single cell or tissue type (both pathological and non-pathological cells and tissue) typically expresses more than one SSTRx subtype, and the fact that the relative proportion of the different SSTRx of a given cell can change over time (apparently at least in part as a result of exposure to non-Somatostatin hormones, neuropeptides and other biochemical changes) makes it difficult if not impossible to determine the function of a specific SSTRx or SST hormone in a specific tissue type or tissue organism.

The binding affinity of both Octreotide and Lanreotide to SSTR2 is substantially greater than to the other SSTRx. As a result, Octreotide and Lanreotide are potentially less effective or ineffective in some instances, and may potentially cause side-effects in other instances as a result of different and time-varying distribution of different SSTRx in a given cell type in a given organism. The variation of the distribution of SSTRx in different cells may at least in part responsible for the extensive list of indications for which administration of Octreotide has been suggested.

Octreotide is reported to have many pharmacological effects, including: inhibition of secretion of gastrin, cholecystokinin, glucagon, growth hormone, insulin, secretin, pancreatic peptide, TSH, and vasoactive intestinal peptide; reduction of secretion of fluids by the intestine and pancreas; reduction of gastrointestinal motility and inhibition of contraction of the gallbladder; inhibition of the action of certain hormones from the anterior pituitary; vasoconstriction in the blood vessels; and reduction of portal vessel pressures in bleeding varices. Octreotide has been used for the treatment of growth hormone producing tumors (acromegaly and gigantism), pituitary tumors that secrete thyroid stimulating hormone (thyrotropinoma), diarrhea and flushing episodes associated with carcinoid syndrome, and diarrhea in patients with vasoactive intestinal peptide-secreting tumors (VIPomas). Octreotide has also been used off-label or experimentally for the treatment of other pathologies including: severe, refractory diarrhea; prolonged recurrent hypoglycemia after sulfonylurea and possibly meglitinides overdose; nesidioblastosis in infants to help decrease insulin hypersecretion; obesity, particularly obesity caused by lesions in the hunger and satiety centers of the hypothalamus; pain from chronic pancreatitis; thymic neoplasms; hypertrophic pulmonary osteoarthropathy (HPOA) secondary to non-small cell lung carcinoma; malignant bowel obstruction; chylothorax; acute haemorrhage from esophageal varices in liver cirrhosis; and idiopathic intracranial hypertension. Octreotide may be used in conjunction with midodrine to partially reverse peripheral vasodilation in the hepatorenal syndrome or treat refractory chronic hypotension.

Octreotide—active agent conjugates (a single molecule including an Octreotide moiety covalently bonded to a distinct active agent moiety) are known where a therapeutic or imaging active agent is covalently bonded to the Octreotide moiety through the nitrogen atom of the N-terminal DPhe amino acid residue. In such conjugates, the Octreotide moiety functions as a guiding moiety to concentrate and cause internalization of the active agent moiety by binding to SSTR2 of neuroendocrine and other tumors overexpressing SSTR2.

In the field of medicinal chemistry, the synthesis of analogues of endogenous receptor ligands for pharmaceutical administration as exogenous receptor ligands is known. Although small-molecule synthetic analogues are known, research of peptide synthetic analogues is considered exceptionally attractive. In such research, the amino acid residue sequence of the pharmacophore of the endogenous receptor ligands is identified. Subsequently, potential exogenous ligands are made by synthesizing peptides (in some instance cyclic peptides for conformational constraint and to protect the peptide from in vivo proteolysis) that have a pharmacophore amino acid residue sequence that is similar to that of the endogenous receptor ligand pharmacophore. Many peptides are synthesized as ligand candidates including variants with various sequences, different ring sizes and cyclization chemistry to vary the conformation of the pharmacophore, as well as variation of the constituent amino acid residues of the pharmacophore, e.g., varying with D-isomers, non-natural amino acids, or similar amino acids. The synthesized ligand candidates are then tested for binding affinity and inherent pharmaceutical activity.

A found synthetic ligand is typically used in one or both of two ways. In some instances, the inherent pharmaceutical activity of the synthetic ligand (e.g., as an agonist or antagonist) renders the synthetic ligand pharmaceutically useful as-is. Additionally or alternatively, when the binding affinity to the receptor is sufficiently high, the synthetic ligand is covalently bonded to an active agent moiety to form a conjugate where the synthetic ligand moiety functions as a guiding moiety to concentrate the active agent moiety in the vicinity of cells by binding to the appropriate receptor, and in some instances also allowing internalization of the active agent moiety. Typical active agents are therapeutic or diagnostic and include toxins and photosensitizers (that, once internalized, potentially kill a cell), dyes and fluorescent active agents (useful in identifying types of tissue, e.g. for diagnosis and guiding surgery), chelators (useful in delivering metals into cells), moieties with metal atoms, radioactive active agents (useful in diagnosis and, in some cases, killing of cells), and "packages" such as nanoparticles, micelles and liposomes (inter alia, for delivering large amounts of other secondary active agents contained therein).

While studying synthetic Somatostatin analogue variants of the cyclic peptides designated "3207" in U.S. Pat. No. 7,700,717:

```
                                        (SEQ ID NO: 6)
        DPhe-Cys*-Phe-Trp-DTrp-Lys-Thr-

Phe-GlyS2*-NH2
``` and the peptide-fluorescent agent conjugate designated "86" thereof:

```
        FITC-GABA-DPhe-Cys*-Phe-Trp-DTrp-

Lys-Thr-Phe-GlyS2*-NH2
``` the present Inventors synthesized fifteen new compounds, all Somatostatin receptor ligands comprising a peptide moiety and a fluorescent moiety, that demonstrated effective in vitro binding to cells overexpressing SSTRx. Surprisingly, the disclosed Somatostatin receptor ligands had affinities to the various SSTRx, that are different than the known preferential binding of Octreotide and Lanreotide to SSTR2 and the preferential binding of SST-14 and SST-28 to SSTR5. The synthesized peptide-fluorescent compounds are described in Table 1 and the relative binding affinities to the different SSTRx are presented in Tables 2, 2-A and 2-B, hereinbelow.

Provided herein are, inter alia, compounds and methods as follows:
  disclosed are peptide moieties (e.g., proteins, peptides) including amino acid residue sequences having different relative affinities to the different SSTRx, that in some embodiments are Somatostatin receptor ligands;
  disclosed are Somatostatin receptor ligands each having a different relative affinity to the different SSTRx, that are useful, inter alia, for characterizing tissue and cells that overexpress SSTRx in vitro;
  disclosed are peptides, that are useful, inter alia, for the synthesis of the Somatostatin receptor ligands comprising a fluorescent moiety, as well as of other Somatostatin receptor ligands;
  disclosed are peptides that are useful, inter alia, for the synthesis of Somatostatin receptor ligands for treating diseases and disorders associated with SSTRx expression;
  disclosed are peptides that are useful, inter alia, for the synthesis of Somatostatin receptor ligands for diagnosis of diseases and disorders associated with SSTRx expression;
  further disclosed are peptides that are useful, inter alia, for the synthesis of the Somatostatin receptor ligands for the preparation of a medicament or the treatment and diagnosis of diseases and disorders associated with SSTRx expression.

First Aspect

Thus, according to an aspect of some embodiments of the teachings herein, there is provided a Somatostatin receptor ligand (in some embodiments, a synthetic Somatostatin receptor ligand), comprising: a peptide moiety including the amino acid residue sequence (SEQ ID NO:7):

-Xxx3-Xxx4-DTrp-Xxx6-Thr-Phe-A wherein:
  Xxx3 is selected from the group consisting of Phe and Tyr;
  Xxx4 is present or absent and if present is selected from the group consisting of Trp and Phe;
  Xxx6 is selected from the group consisting of amino acid residues having a side chain with at least one nitrogen atom;
  A is any chemical entity
and wherein at least one of:
  a. Xxx3 is Tyr;
  b. Xxx4 is present or absent and if present is Phe; and
  c. Xxx6 is other than Lys
and salts, esters and amides thereof.

In some embodiments, the peptide moiety sequence comprises amino acid residue sequence set forth as SEQ ID NO:7: -Xxx3-Xxx4-DTrp-Xxx6-Thr-Phe-A, wherein Xxx3 is Tyr, for example, compounds 4, 6 and 7 (SEQ ID NOS:21, 30 and 35, respectively).

In some embodiments, the peptide moiety sequence comprises amino acid residue sequence set forth as SEQ ID NO:7: -Xxx3-Xxx4-DTrp-Xxx6-Thr-Phe-A, wherein Xxx4 is present or absent and if present is Phe, for example, compounds 2 and 5-10 (SEQ ID NOS:12, 25, 30, 35, 39, 45, 46, respectively).

In some embodiments, the peptide moiety sequence comprises amino acid residue sequence set forth as SEQ ID NO:7: -Xxx3-Xxx4-DTrp-Xxx6-Thr-Phe-A, wherein Xxx6 is selected from the group consisting of amino acid residues having a side chain with at least one nitrogen atom excluding natural amino acid Lys, for example, compounds 3, 5, 7 and 13-16 (SEQ ID NOS: 17, 25, 35, 54, 58, 62, 64 respectively). In some such embodiments, Xxx6 is selected from the group consisting of Orn, Aib, LysAc, Arg and homolysine.

In some embodiments, there is provided a Somatostatin receptor ligand (in some embodiments, a synthetic Somatostatin receptor ligand), comprising: a peptide moiety including the amino acid residue sequence set forth in SEQ ID NO:8: -Xxx2-Xxx3-Xxx4-DTrp-Xxx6-Thr-Phe-A, wherein Xxx2 is Arg, for example, compounds 8-10 (SEQ ID NOS:39, 45, 46, respectively).

In some embodiments, there is provided a Somatostatin receptor ligand (in some embodiments, a synthetic Somatostatin receptor ligand), comprising: a peptide moiety including the amino acid residue sequence set forth in SEQ ID NO:9: Xxx1-Xxx2-Xxx3-Xxx4-DTrp-Xxx6-Thr-Phe-A, wherein Xxx2 is present or absent and if present is Arg; and wherein Xxx1 is a an amino acid having a side chain with a sulfur atom. In some embodiments, Xxx1 is selected from the group consisting of GlyS2, Cys, HCys and DCys.

According to an aspect of some embodiments of the teachings herein, there is also provided a Somatostatin receptor ligand (in some embodiments, a synthetic Somatostatin receptor ligand), comprising: a peptide moiety including the amino acid residue sequence set forth as SEQ ID NO:9:

-Xxx1-Xxx2-Xxx3-Xxx4-DTrp-Xxx6-Thr-Phe-A wherein:
  Xxx1 is selected from the group consisting of GlyS2, Cys, HCys and DCys;
  Xxx2 is present or absent and if present is Arg;
  Xxx3 is selected from the group consisting of Phe and Tyr;
  Xxx4 is present or absent and if present is selected from the group consisting of Trp and Phe;
  Xxx6 is selected from the group consisting of amino acid residues having a side chain with at least one nitrogen atom; and
  A is any chemical entity
and salts, esters and amides thereof, for example, compounds 11 and 12 (SEQ ID NOS: 50 and 52).

In some embodiments, the Somatostatin receptor ligand above comprises an amino acid sequence set forth as SEQ ID NO:10: -Arg-Xxx1-Xxx2-Xxx3-Xxx4-DTrp-Xxx6-Thr-Phe-A (SEQ ID NOS:12, 25, 30, respectively).

In some embodiments, the Somatostatin receptor ligand comprises an amino acid sequence set forth as SEQ ID NO:11: -DPhe-Xxx0-Xxx1-Xxx2-Xxx3-Xxx4-DTrp-Xxx6-Thr-Phe-A, wherein Xxx0 is present or absent and if present is Arg (SEQ ID NO:6, 12, 17, 21, 25, 30, 35, 39, 46, 50, 52, 54, 58, 62, 64, e.g. Arg in SEQ ID NOS:12, 25, 35; absent in remainder).

In some embodiments, a portion of the peptide moiety of the Somatostatin receptor ligand is cyclic, the cyclic portion comprising at least a portion of an amino acid sequence selected from the group consisting of:

Xxx3-Xxx4-DTrp-Xxx6-Thr-Phe- (SEQ ID NO: 7 devoid of the C-terminal chemical entity A);
Arg-Xxx3-Xxx4-DTrp-Xxx6-Thr-Phe- (SEQ ID NO: 8 devoid of the C-terminal chemical entity A); and
Xxx1-Xxx2-Xxx3-Xxx4-DTrp-Xxx6-Thr-Phe- (SEQ ID NO: 9 devoid of the C-terminal chemical entity A).

In some embodiments, the portion of the peptide moiety of the Somatostatin receptor ligand that is cyclic comprises an amino acid sequence selected from the group consisting of:

Xxx3-Xxx4-DTrp-Xxx6-Thr-Phe- (SEQ ID NO: 7 devoid of the C-terminal chemical entity A);
Arg-Xxx3-Xxx4-DTrp-Xxx6-Thr-Phe- (SEQ ID NO: 8 devoid of the C-terminal chemical entity A); and
Xxx1-Xxx2-Xxx3-Xxx4-DTrp-Xxx6-Thr-Phe- (SEQ ID NO: 9 devoid of the C-terminal chemical entity A).

In some embodiments, the portion of the peptide moiety that is cyclic is cyclized by a sulfur-sulfur (disulfide) bond, for example, between two cysteine residues, a cysteine residue and a GlyS2 residue, a cysteine residue and a cysteine analog or two GlyS2 residues.

In some such embodiments, the sequence comprises an amino acid sequence set forth as SEQ ID NO:9:

```
-Xxx1-Xxx2-Xxx3-Xxx4-DTrp-Xxx6-Thr-Phe-A
``` wherein:
Xxx1 is selected from the group consisting of Cys, HCys and DCys; the chemical entity A is a chemical entity Xxx9-A' wherein Xxx9 is an amino acid residue directly bonded to the Phe residue and that includes a sulfur atom; A' is any suitable chemical entity; and the sulfur-sulfur bond is that cyclizes the amino acid sequence is between the sulfur atom of Xxx9 and a sulfur atom of Cys, HCys or DCys of Xxx1. As noted above, A' is any suitable chemical entity bonded to complete the valency of the Xxx9 amino acid residue. In some such embodiments, Xxx9 is a GlyS2 residue. Some such embodiments relate to the second and/or third aspects of the teachings herein, in addition to being related to the first aspect of the teachings herein.

In some embodiments, the peptide moiety includes an amino acid residue sequence selected from the group consisting of:
related to compound 2 (SEQ ID NO:12):

```
                                     (SEQ ID NO: 13)
-Phe-DTrp-Lys-Thr-Phe-A;

(SEQ ID NO: 14)
-Cys-Phe-DTrp-Lys-Thr-Phe-A;

(SEQ ID NO: 15)
-Arg-Cys-Phe-DTrp-Lys-Thr-Phe-A;

(SEQ ID NO: 16)
-DPhe-Arg-Cys-Phe-DTrp-Lys-Thr-Phe-A
```

(e.g., compound 2, (SEQ ID NO:12)
related to compound 3 (SEQ ID NO:17):

```
                                     (SEQ ID NO: 18)
-Phe-Trp-DTrp-Orn-Thr-Phe-A;

(SEQ ID NO: 19)
-Cys-Phe-Trp-DTrp-Orn-Thr-Phe-A;

(SEQ ID NO: 20)
-DPhe-Cys-Phe-Trp-DTrp-Orn-Thr-Phe-A
```

(e.g., compound 3, (SEQ ID NO:17);
related to compound 4 (SEQ ID NO:21):

```
                                     (SEQ ID NO: 22)
-Tyr-Trp-DTrp-Lys-Thr-Phe-A;

(SEQ ID NO: 23)
-Cys-Tyr-Trp-DTrp-Lys-Thr-Phe-A;

(SEQ ID NO: 24)
-DPhe-Cys-Tyr-Trp-DTrp-Lys-Thr-Phe-A
```

(e.g., compound 4, (SEQ ID NO:21);
related to compound 5 (SEQ ID NO:25):

```
                                     (SEQ ID NO: 26)
-Phe-DTrp-Orn-Thr-Phe-A;

(SEQ ID NO: 27)
-Cys-Phe-DTrp-Orn-Thr-Phe-A;

(SEQ ID NO: 28)
-Arg-Cys-Phe-DTrp-Orn-Thr-Phe-A;

(SEQ ID NO: 29)
-DPhe-Arg-Cys-Phe-DTrp-Orn-Thr-Phe-A
```

(compound 5, (SEQ ID NO:25);
related to compound 6 (SEQ ID NO:30):

```
                                     (SEQ ID NO: 31)
-Tyr-DTrp-Lys-Thr-Phe-A;

(SEQ ID NO: 32)
-Cys-Tyr-DTrp-Lys-Thr-Phe-A;

(SEQ ID NO: 33)
-Arg-Cys-Tyr-DTrp-Lys-Thr-Phe-A;

(SEQ ID NO: 34)
DPhe-Arg-Cys-Tyr-DTrp-Lys-Thr-Phe-A
```

(e.g., compound 6, (SEQ ID NO:30);
related to compound 7 (SEQ ID NO:35):

```
                                     (SEQ ID NO: 36)
-Tyr-DTrp-Orn-Thr-Phe-A;

(SEQ ID NO: 37)
-Cys-Tyr-DTrp-Orn-Thr-Phe-A;

(SEQ ID NO: 38)
-DPhe-Cys-Tyr-DTrp-Orn-Thr-Phe-A
```

(e.g., compound 7, (SEQ ID NO:35);
related to compound 8 (SEQ ID NO:39):

```
                                     (SEQ ID NO: 40)
-Phe-DTrp-Lys-Thr-Phe-A;

(SEQ ID NO: 41)
-Phe-Phe-DTrp-Lys-Thr-Phe-A;
```

```
                                                  (SEQ ID NO: 42)
    -Arg-Phe-Phe-DTrp-Lys-Thr-Phe-A;

(SEQ ID NO: 43)
    -Cys-Arg-Phe-Phe-DTrp-Lys-Thr-Phe-A;

(SEQ ID NO: 44)
    -DPhe-Cys-Arg-Phe-Phe-DTrp-Lys-Thr-Phe-A
```

(e.g., compound 8, (SEQ ID NO:39);
related to compounds 9 (SEQ ID NO:45) and 10 (SEQ ID NO:46):

```
                                                  (SEQ ID NO: 47)
    -Arg-Phe-DTrp-Lys-Thr-Phe-A;

(SEQ ID NO: 48)
    -Cys-Arg-Phe-DTrp-Lys-Thr-Phe-A
```

(e.g., compound 9, (SEQ ID NO:45);

```
                                                  (SEQ ID NO: 49)
    -DPhe-Cys-Arg-Phe-DTrp-Lys-Thr-Phe-A
```

(e.g., compound 10 (SEQ ID NO:46);
related to compound 11 (SEQ ID NO:50):

```
                                                  (SEQ ID NO: 51)
    -DPhe-HCys-Phe-Trp-DTrp-Lys-Thr-Phe-A
```

(e.g., compound 11, (SEQ ID NO:50);
related to compound 12 (SEQ ID NO:52):

```
                                                  (SEQ ID NO: 53)
    -DPhe-DCys-Phe-Trp-DTrp-Lys-Thr-Phe-A
```

(e.g., compound 12, (SEQ ID NO:52);
related to compound 13 (SEQ ID NO:54):

```
                                                  (SEQ ID NO: 55)
    -Phe-Trp-DTrp-Aib-Thr-Phe-A;

(SEQ ID NO: 56)
    -Cys-Phe-Trp-DTrp-Aib-Thr-Phe-A;

(SEQ ID NO: 57)
    -DPhe-Cys-Phe-Trp-DTrp-Aib-Thr-Phe-A
```

(e.g., compound 13, (SEQ ID NO:54);
related to compound 14 (SEQ ID NO:58):

```
                                                  (SEQ ID NO: 59)
    -Phe-Trp-DTrp-LysAc-Thr-Phe-A;

(SEQ ID NO: 60)
    -Cys-Phe-Trp-DTrp-LysAc-Thr-Phe-A;

(SEQ ID NO: 61)
    -DPhe-Cys-Phe-Trp-DTrp-LysAc-Thr-Phe-A
```

(e.g., compound 14, (SEQ ID NO:58);
related to compound 15 (SEQ ID NO:62):

```
                                                  (SEQ ID NO: 63)
    DPhe-Cys-Phe-Trp-DTrp-Arg-Thr-Phe-A
```

(e.g., compound 15; (SEQ ID NO:62),
related to compound 16 (SEQ ID NO:64)

```
                                                  (SEQ ID NO: 65)
    -Phe-Trp-DTrp-HomoLys-Thr-Phe-A;

(SEQ ID NO: 66)
    -Cys-Phe-Trp-DTrp-HomoLys-Thr-Phe-A;
    and (SEQ ID NO: 67)
    -DPhe-Cys-Phe-Trp-DTrp-HomoLys-Thr-Phe-A
```

(e.g., compound 16, (SEQ ID NO:64)).

In some embodiments, a Somatostatin receptor ligand comprising an amino acid residue sequence selected from the above group further includes an additional amino acid residue selected from the group consisting of GlyS2, Cys, HCys and DCys, covalently bonded to the N-terminal amino acid of the selected sequence;

the chemical entity A is a chemical entity Xxx9-A' wherein Xxx9 is an amino acid residue directly bonded to the Phe residue located at the C-terminus of the selected sequence and that includes a sulfur atom;

A' is any chemical entity; and the selected amino acid sequence is cyclized with a sulfur-sulfur bond between the sulfur atom of Xxx9 and a sulfur atom of GlyS2, Cys, HCys or DCys. As noted above, A' is any suitable chemical entity bonded to complete the valency of the Xxx9 amino acid residue. In some such embodiments, Xxx9 is a GlyS2 residue. Some such embodiments relate to the second and/or third aspects of the teachings herein, in addition to being related to the first aspect of the teachings herein.

It is important to note that a peptide moiety that includes an amino acid residue sequence as described hereinabove is not necessarily an entire Somatostatin receptor ligand according to the teachings herein. Rather, a given Somatostatin receptor ligand according to the teachings herein comprises the peptide moiety including the recited amino acid sequence and typically further comprises one or more additional chemical entity at the N-terminus of the peptide moiety to complete the valency thereof, for example chemical entities bonded to the -Xxx3 residue of SEQ ID NO: 7 or bonded to Arg or -Xxx1 residue of SEQ ID NO:8 and 9, respectively).

In some embodiments, the N-terminal amino acid of the amino acid residue sequence is the N-terminal amino acid of the peptide moiety of the Somatostatin receptor ligand, that is to say, the -Xxx3 residue of SEQ ID NO: 7 or the Arg or -Xxx1 residue of SEQ ID NOS: 8 and 9, respectively. In some embodiments, there is at least one additional amino acid residue covalently bonded to the N-terminal amino acid of the amino acid residue sequence.

In some embodiments, the N-terminal amine of the N-terminal amino acid of the peptide moiety of the Somatostatin receptor ligand is bonded to any suitable chemical entity, e.g., one or two H atoms, one or two alkyl groups, one or two active agent moieties (as detailed hereinbelow), and combinations thereof. In some embodiments, the nitrogen atom of the N-terminal amino acid of the peptide moiety is selected from the group consisting of a primary amine, a secondary amine and a tertiary amine. In some embodiments, there is a chemical entity covalently bonded to the N-terminal amino acid of the peptide moiety of the Somatostatin receptor ligand, in some embodiments, through the terminal nitrogen thereof. In some embodiments, the chemical entity is covalently bonded to the N-terminal amino acid through the terminal nitrogen with a bond selected from the group consisting of an amide bond, an imine bond, an amine bond, a sulfamide bond and a phosphamide bond.

As noted above, in embodiments of the first aspect of the teachings herein, chemical entity A is any suitable chemical entity bonded to complete the valency of the Phe amino acid residue near the C-terminus of the amino acid residue sequence of a peptide moiety of a Somatostatin receptor ligand. In some embodiments, the chemical entity A is covalently bonded to the Phe amino acid residue of the amino acid residue sequence through the terminal carbonyl group of the Phe amino acid residue with a bond selected from the group consisting of an amide bond. In some embodiments, chemical entity A is selected from the group consisting of: an entity comprising an amino acid residue, an entity comprising —OH, an entity comprising —O$^-$M$^+$, (where M+ is a metal cation so that the Somatostatin receptor ligand is an acid salt), an entity comprising an alkoxy group, an entity comprising an amine, an entity comprising an active agent moiety and combinations thereof.

In some embodiments, chemical entity A comprises at least one amino acid residue that is directly bonded with a peptide bond to the C-terminal carbonyl of the Phe amino acid residue of the amino acid residue sequence. In some embodiments, chemical entity A comprises at least two, at least four and even at least eight amino acid residues. In some embodiments of the first aspect that are also related to the second and/or third aspects of the teachings herein, chemical entity A is -Xxx9-A', where Xxx9 is an amino acid residue, and A' is any suitable chemical entity bonded to complete the valency of the Xxx9 amino acid residue. In some preferred embodiments, Xxx9 is a GlyS2 amino acid residue. In some embodiments, chemical entity A' comprises at least one, at least two, at least four and even at least eight amino acid residues. In some embodiments, A' is selected from the group consisting of: —OH (in which case the receptor ligand is a free acid), —O$^-$M$^+$ (in which case the receptor ligand is an acid salt), an alkoxy group (in which case the receptor ligand is an ester), an amine (in which case the receptor ligand is a C-terminal amide), an active agent moiety (as detailed hereinbelow), an entity comprising an amino acid residue, an entity comprising —OH, an entity comprising —O$^-$M$^+$, an entity comprising an alkoxy group, an entity comprising an amine, an entity comprising an active agent moiety and combinations thereof.

In some embodiments, the portion of chemical entity A that is directly bonded to the C-terminal carbonyl of the Phe amino acid residue of the amino acid residue sequence is not an amino acid residue. For example, in some embodiments, A is selected from the group consisting of: —OH (in which case the receptor ligand is a free acid), —O$^-$M$^+$ (in which case the receptor ligand is an acid salt), an alkoxy group (in which case the receptor ligand is an ester), an amine (in which case the receptor ligand is a C-terminal amide), an active agent moiety (as detailed hereinbelow), an entity comprising an amino acid residue (that is not directly bonded to the Phe residue), an entity comprising —OH, an entity comprising —O$^-$M$^+$, an entity comprising an alkoxy group, an entity comprising an amine, an entity comprising an active agent moiety and combinations thereof.

As noted above, the peptide moiety of the Somatostatin receptor ligand includes the above-referenced amino acid residue sequence and optionally includes additional amino acid residues bonded to the N-terminal amino acid residue of the amino acid residue sequence as described above, and/or additional amino acid residues bonded to the C-terminal amino acid residue (which additional amino acid residues constitute at least part of chemical entity A) of the amino acid residue sequence as described above. The length of the peptide moiety of the Somatostatin receptor ligand is any suitable length. In some embodiments, the peptide moiety comprises not more than 1000 amino acid residues, not more than 500 amino acid residues, not more than 100 amino acid residues, not more than 50 amino acid residues, not more than 30 amino acid residues, not more than 20 amino acid residues, not more than 15 amino acid residues and even not more than 11 amino acid residues. In some embodiments, the peptide moiety comprises an amino acid sequence of 5, 6, 7, 8, 9, 10 or 11 amino acid residues.

In some embodiments, the peptide moiety of a Somatostatin receptor ligand according to the first aspect of the teachings herein is non-cyclical, that is to say, along the entire length of the peptide moiety, the only covalent bonds between any two amino acid residues are the peptide backbone peptide bonds. In some embodiments, the peptide moiety of a Somatostatin receptor ligand according to the first aspect of the teachings herein is cyclical, that is to say, there is at least one covalent bond between two amino acid residues of the peptide moiety in addition to the peptide backbone peptide bonds, for example the linear sequences disclosed herein further include sulfur-containing amino acid residues at or near each of the N- and C-termini (for example at N-terminus and penultimate position at C-terminus, at N-terminus and C-terminus or or at C-terminus and penultimate position at N-terminus. In some such embodiments, the cyclical portion includes the subsequence -Xxx3-Xxx4-DTrp-Xxx6-Thr-Phe- (SEQ ID NO:7). In some such embodiments, the cyclical portion includes the subsequence -Arg-Xxx3-Xxx4-DTrp-Xxx6-Thr-Phe- (SEQ ID NO:8). In some such embodiments, the cyclical portion includes the subsequence -Xxx1-Xxx2-Xxx3-Xxx4-DTrp-Xxx6-Thr-Phe- (SEQ ID NO:9).

In some embodiments of the first aspect of the teachings herein (e.g., SEQ ID NOS: 7-68), the peptide moiety (cyclic or not-cyclic) is bonded to a solid-phase peptide synthesis (SPPS) support, e.g., glass support, cellulose fiber support, polystyrene support, polyacrylamide support, polyethylene glycol support.

In some embodiments of the first aspect of the teachings herein, the peptide moiety (cyclic or not cyclic, bonded to a SPPS support or not bonded to an SPSS support) includes one or more protecting groups on the functional groups of the peptide moiety. A person having ordinary skill in the art is able to select and add suitable protecting groups to functional groups, upon perusal of the specification and, if necessary, consultation with standard chemical synthesis literature. Suitable protecting groups include t-Boc, Fmoc, benzyloxy-carbonyl, Alloc, benzyl and tert-butyl.

In some embodiments, a Somatostatin receptor ligand according to the first aspect of the teachings herein consists essentially of the peptide moiety, that is to say, is devoid of an active agent conjugated therewith. For example, in some such embodiments, a Somatostatin receptor ligand consists essentially of the cyclic peptide moiety of compounds 2-16, without the FITC-GABA-active agent moiety, and is selected form the group consisting of:

```
                                               (SEQ ID NO: 12)
Z-DPhe-Arg-Cys*-Phe-DTrp-Lys-Thr-Phe-GlyS2*-A';

(SEQ ID NO: 17)
Z-DPhe-Cys*-Phe-Trp-DTrp-Orn-Thr-Phe-GlyS2*-A';
```

-continued

```
                                         (SEQ ID NO: 21)
Z-DPhe-Cys*-Tyr-Trp-DTrp-Lys-Thr-Phe-GlyS2*-A';

(SEQ ID NO: 25)
Z-DPhe-Arg-Cys*-Phe-DTrp-Orn-Thr-Phe-GlyS2*-A';

(SEQ ID NO: 30)
Z-DPhe-Arg-Cys*-Tyr-DTrp-Lys-Thr-Phe-GlyS2*-A';

(SEQ ID NO: 35)
Z-DPhe-Cys*-Tyr-DTrp-Orn-Thr-Phe-GlyS2*-A';

(SEQ ID NO: 39)
Z-DPhe-Cys*-Arg-Phe-Phe-DTrp-Lys-Thr-Phe-GlyS2*-
A';

(SEQ ID NO: 45)
Z-Cys*-Arg-Phe-DTrp-Lys-Thr-Phe-GlyS2*-A';

(SEQ ID NO: 46)
Z-DPhe-Cys*-Arg-Phe-DTrp-Lys-Thr-Phe-GlyS2*-A';

(SEQ ID NO: 50)
Z-DPhe-HCys*-Phe-Trp-DTrp-Lys-Thr-Phe-GlyS2*-A';

(SEQ ID NO: 52)
Z-DPhe-DCys*-Phe-Trp-DTrp-Lys-Thr-Phe-GlyS2*-A';

(SEQ ID NO: 54)
Z-DPhe-Cys*-Phe-Trp-DTrp-Aib-Thr-Phe-GlyS2*-A';

(SEQ ID NO: 58)
Z-DPhe-Cys*-Phe-Trp-DTrp-LysAc-Thr-Phe-GlyS2*-A';

(SEQ ID NO: 62)
Z-DPhe-Cys*-Phe-Trp-DTrp-Arg-Thr-Phe-GlyS2*-A';
and (SEQ ID NO: 64)
Z-DPhe-Cys*-Phe-Trp-DTrp-HomoLys-Thr-Phe-GlyS2*-
A',
``` wherein Z is a chemical entity covalently bonded to the terminal amino group of the N-terminal amino acid residue to complete the valency thereof as described above, e.g., 2H (2 hydrogen atoms. in which case the receptor ligand is a primary amine), an alkyl group and an H (in which case the receptor ligand is a secondary amine), or two alkyl groups (in which case the receptor ligand is a tertiary amine); and A' (A prime) is chemical entity covalently bonded to the terminal carbonyl group of the C-terminal amino acid residue as described above, e.g., —OH, an alkoxy group, an amine. In some embodiments, the asterisks indicate cyclization by an S—S bond between the two amino acid residues. In some embodiments, such Somatostatin receptor ligands are useful, inter alia, as starting materials for the synthesis of other Somatostatin receptor ligands according to the teachings herein.

In some embodiments according to any one of the first, second or third aspects of the teachings herein, there is provided a Somatostatin receptor ligand having any one of the cited amino acid residue sequences excepting SEQ ID NO:54), and further comprising an active agent moiety covalently bonded to the nitrogen atom of the side-chain of the amino acid residue (i.e., Lys, Orn, Arg, LysAc, homo-Lys). In embodiments of the third aspect having only one active agent moiety, the active agent moiety is a nanoparticle active agent moiety.

Peptide Moiety-Active Agent Moiety Conjugates

In some embodiments, a Somatostatin receptor ligand according to the first aspect of teachings herein, comprises at least one active agent moiety covalently bonded to the peptide moiety. In some embodiments, the at least one active agent moiety is at least two active agent moieties covalently bonded to the peptide moiety. In some embodiments, the at least one active agent moiety is at least three active agent moieties covalently bonded to the peptide moiety.

In some embodiments, an active agent moiety is covalently bonded to the peptide moiety through a terminal nitrogen atom of an N-terminal amino acid residue of the peptide moiety.

In some embodiments, an active agent moiety is covalently bonded to the peptide moiety through a terminal carbonyl group of a C-terminal amino acid residue of the peptide moiety, and constitutes at least a portion of the chemical entity A.

In some embodiments, an active agent moiety covalently bonded to the peptide moiety through a side chain of an amino acid residue of the peptide moiety.

In some embodiments, an active agent moiety is covalently bonded to the peptide moiety through a nitrogen atom present in the side chain of the Xxx6 nitrogen-containing amino acid residue.

The covalent bond between the active agent moiety and the peptide moiety is any suitable covalent bond. A person having ordinary skill in the art is able to select and synthesize a suitable covalent bond upon perusal of the specification. In some embodiments, the covalent bond between the peptide moiety and the active agent moiety is selected from the group of bonds consisting of:

an amide bond, e.g., formed by the coupling reaction of a primary or secondary amine with an acid or ester function;

an imine bond, e.g., formed by the coupling reaction of a primary or secondary amine with a ketone or aldehyde function;

an amine bond, e.g., formed by an amine-alkylation reaction of a primary or secondary amine with an alkyl halide function;

a sulfamide bond, e.g., formed by a coupling reaction of a primary or secondary amine with a sulfonyl chloride function; and a phosphamide bond, e.g., formed by a coupling reaction of a primary or secondary amine with a phophoryl chloride function.

A given active agent moiety is any suitable active agent moiety. In some embodiments, an active agent moiety selected from the group consisting of: an imaging moiety, a therapeutic moiety, a dye, a fluorescent moiety, a toxin, a chelator, a moiety with a metal atom, a radioactive atom or a moiety with a radioactive atom, a nanoparticle, an ethylene glycol polymer, photosensitizer, a liposome constituent and a micelle constituent. It is important to note that in some instances a single active agent moiety falls within the definition of two or more elements of the above group, for example: in some embodiments an active agent moiety is a nanoparticle and an ethylene glycol polymer and either or both therapeutic/imaging; in some embodiments an active agent moiety is a dye, and/or fluorescent moiety and/or a photosensitizer and either or both therapeutic/imaging; in some embodiments an active agent moiety includes a radioactive atom and falls within one or more of the other definitions.

In some embodiments, during use of a Somatostatin receptor ligand according to the teachings herein, the receptor ligand preferentially (or even selectively) binds to a cell expressing or overexpressing one or more Somatostatin receptor, in some embodiments at least partially due to the affinity of the peptide moiety to a Somatostatin receptor, which in some embodiments is followed by internalization of the receptor ligand into the cell. Such preferential or selective binding to the cell concentrates the active agent on or in the cell, which subsequently has a desired effect that depends on the nature of the active agent.

Further details relating to active agent moieties suitable for implementing embodiments of the first aspect of the teachings herein are discussed herein below.

Second and Third Aspect

In the field of biology, it is known that biological processes in a living organism are regulated by endogenous receptor ligands that bind to an appropriate receptor, thereby affecting cellular processes with which the receptor is involved. The exact effect a given receptor ligand has when binding to a receptor depends on various factors, including whether the receptor ligand is an agonist, antagonist, inverse agonist, partial agonist or co-agonist for the receptor.

Many endogenous receptor ligands are proteins of which a small portion (typically between 3 and 20 amino acid residues long) is the pharmacophore that actually binds to the receptor, typically through one or more of ionic bonds, hydrogen bonds and van der Waals forces. The non-pharmacophore portion of the endogenous receptor ligand defines and fixes the exact conformation of the pharmacophore allowing efficient, specific and/or and selective binding to the receptor.

In the field of medicinal chemistry, the synthesis of analogues of endogenous receptor ligands for pharmaceutical administration as exogenous receptor ligands is known. Although small-molecule synthetic analogues are known, research of peptide synthetic analogues is considered exceptionally attractive. In such research, the amino acid residue sequence of the pharmacophore of the endogenous receptor ligands is identified. Subsequently, potential exogenous ligands are made by synthesizing peptides that are cyclic (for conformational constraint and to protect the peptide from in vivo digestion) and have a pharmacophore amino acid residue sequence that is similar to that of the endogenous receptor ligand pharmacophore. Many peptides are synthesized as ligand candidates including variants with different ring sizes and cyclization chemistry to vary the conformation of the pharmacophore, as well as variation of the constituent amino acid residues of the pharmacophore, e.g., varying with D-isomers, non-natural amino acids, or similar amino acids. The synthesized ligand candidates are then tested for binding affinity and inherent pharmaceutical activity.

A found synthetic ligand is typically used in one or both of two ways. In some instances, the inherent pharmaceutical activity of the synthetic ligand (e.g., as an agonist or antagonist) renders the synthetic ligand pharmaceutically useful as-is. Additionally or alternatively, when the binding affinity to the receptor is sufficiently high, the synthetic ligand is covalently bonded to an active agent moiety to form a conjugate where the synthetic ligand moiety functions as a guiding moiety to concentrate the active agent moiety in the vicinity of cells by binding to the appropriate receptor, and in some instances also allowing internalization of the active agent moiety. Typical active agents are therapeutic or diagnostic and include toxins and photosensitizers (that, once internalized, potentially kill a cell), dyes and fluorescent active agents (useful in identifying types of tissue, e.g. for diagnosis and guiding surgery), chelators (useful in delivering metals into cells), moieties with metal atoms, radioactive active agents (useful in diagnosis and, in some cases, killing of cells), and "packages" such as nanoparticles, micelles and liposomes (inter alia, for delivering large amounts of other secondary active agents contained therein).

Such research has met with great success, for example, with the discovery of synthetic Somatostatin analogues based on endogenous SST-14, leading to commercially-available Somatostatin analogues as pharmaceuticals (Lanreotide, Octreotide, Octreotide conjugates) and many additional potential Somatostatin analogues such as described in U.S. Pat. No. 7,700,717.

While studying synthetic Somatostatin analogue variants of the cyclic peptide designated "3207" in U.S. Pat. No. 7,700,717:

(SEQ ID NO: 6)
DPhe-Cys*-Phe-Trp-DTrp-Lys-Thr-Phe-GlyS2*-NH$_2$ the Inventors synthesized Somatostatin receptor ligands comprising a peptide moiety and an active agent moiety where the active agent moiety (a nanoparticle) was covalently bonded to the nitrogen atom of the side chain of the Lys internal amino acid residue of the peptide moiety. The resulting Somatostatin receptor ligands selectively recognized and bonded to in vivo cells overexpressing Somatostatin Receptors and was internalized.

This binding result is unexpected and still unexplained for a number of reasons, including:

the six internal amino acid residues of the cyclic peptide define the pharmacophore thereof, and such a radical change accompanied by steric hindrance of the nanoparticle would be expected to prevent binding to Somatostatin receptors; and since the amino group of the Lys amino acid residue is basic and not sterically hindered, it is assumed that the Lys amino group is an important factor in binding of the pharmacophore to the SSTR, an assumption supported by the fact that SST-14, SST-28, Octreotide, Lanreotide and the cyclic peptides described in U.S. Pat. No. 7,700,717 all include a Lys amino acid residue in an equivalent position.

These unexpected results provide for novel synthetic Somatostatin receptor ligands that substantially comprise a Somatostatin Receptor-binding part that includes a cyclic peptide moiety and an active agent moiety that is covalently bonded to the cyclic peptide moiety through a nitrogen atom of the side chain of the amino acid residue that is equivalent to the Lys amino acid residue discussed above.

Additionally, since a desired active agent moiety is bonded to the cyclic peptide moiety via the Lys internal amino acid residue, the N-terminus and C-terminus of the cyclic peptide moiety are free for covalent bonding to other desired moieties, for example, additional active agent moieties.

Further, at least some of the cyclic peptide moieties according to the teachings herein have been demonstrated to effect in vivo internalization of nanoparticle active agent moieties into pathological cells over-expressing Somatostatin Receptors, thereby providing new pharmaceutical compositions and methods of making such compositions, therapeutic and diagnostic uses of the compositions, and methods of treatment.

Synthetic Somatostatin Receptor Ligands

Second Aspect

Thus, according to a second aspect of some embodiments of the teachings herein, there is provided a synthetic Somatostatin receptor ligand according to the second aspect of the teachings herein, comprising;

a cyclic peptide moiety:
  the cyclic peptide moiety consisting of from 6 to 9 amino acid residues, including an N-terminal amino acid residue, a C-terminal amino acid residue and 4, 5, 6 or 7 internal amino acid residues therebetween;
  each of the N-terminal amino acid residue and the C-terminal amino acid residue having a sulfur-containing functional group, mutually covalently bonded through a sulfur-sulfur bond, thereby cyclizing the peptide moiety;
  wherein at least one of the 4, 5, 6 or 7 internal amino acid residues includes a side chain functional group having a nitrogen atom; and
covalently bonded to the cyclic peptide moiety through the nitrogen atom of the functional group of the internal amino acid residue, an active agent moiety selected from the group consisting of:
  an imaging moiety, a therapeutic moiety, a dye, a fluorescent moiety, a toxin, a chelator, a moiety with a metal atom, a moiety with a radioactive atom, a nanoparticle, an ethylene glycol polymer, a photosensitizer, a liposome constituent and a micelle constituent
and salts, esters and amides thereof.

In some embodiments according to the second aspect of the teachings herein, the cyclic peptide moiety has the amino acid residue sequence set forth in SEQ ID NO:68:

-Xxx1*-Xxx2-Xxx3-Xxx4-Xxx5-Xxx6-Xxx7-Xxx8-Xxx9*- wherein:
  Xxx1 is the N-terminal amino acid residue,
  Xxx9 is the C-terminal amino acid residue,
  the asterisks indicate cyclization by an S—S bond between the amino acid residues Xxx1 and Xxx9, and
  each of Xxx2-Xxx8 is independently present or absent and if present is an internal amino acid, wherein at least 4 of Xxx2-Xxx8 are present, and wherein at least one of the present Xxx2-Xxx8 includes a side chain functional group having a nitrogen atom.

Figure 13:
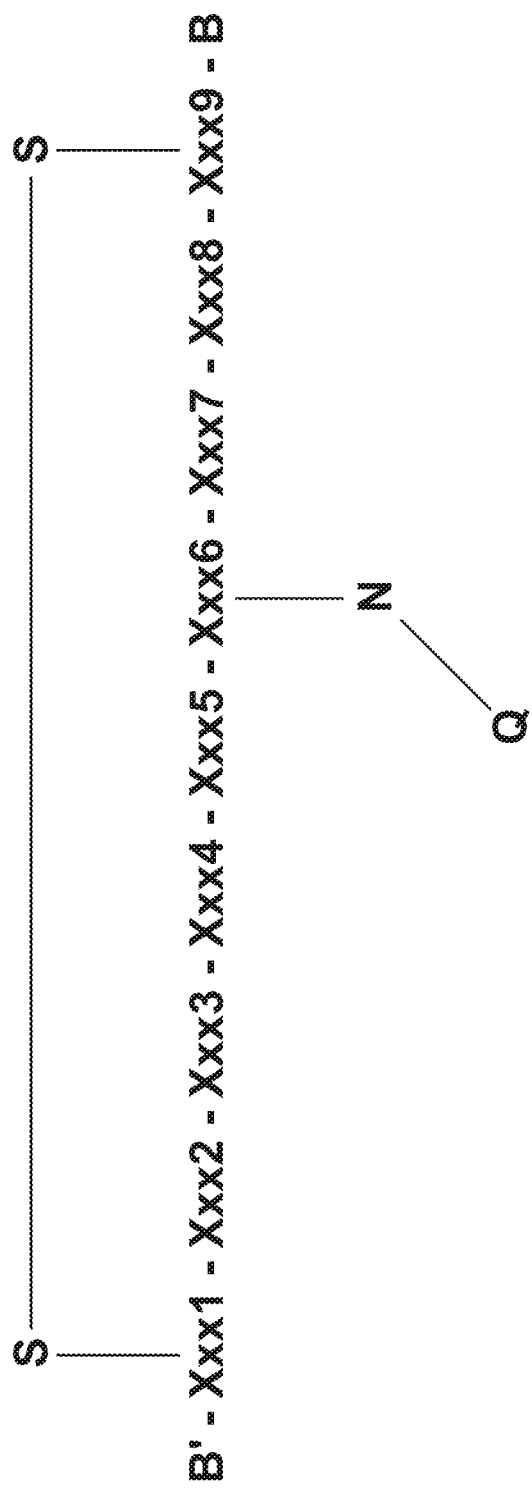
FIG. 13 is a schematic depiction of an embodiment of a synthetic Somatostatin receptor ligand according to the teachings herein and includes a cyclic peptide moiety having an amino acid sequence set forth in SEQ ID NO:68. In some embodiments, at least four of the amino acid residues at positions 2, 3, 4, 5, 6, 7 and 8 are present as discussed hereinabove and hereinbelow.

An embodiment of a synthetic Somatostatin receptor ligand according to the second aspect of the teachings herein having an amino acid sequence set forth in SEQ ID NO:68 is schematically depicted in FIG. 13, wherein: Xxx1 represents the N-terminal amino acid of the cyclic peptide moiety; Xxx9 represents the C-terminal amino acid residue of the cyclic peptide moiety; the asterisks indicate cyclization by an S—S bond between the amino acid residues Xxx1 and Xxx9; Xxx6 represents the internal amino acid residue that includes a side chain functional group having a nitrogen atom; N is the nitrogen atom of the side chain functional group of Xxx6; Q is an active agent moiety bonded through the nitrogen atom; B' is any chemical entity covalently bonded to the terminal amino group of the N-terminal amino acid residue of the cyclic peptide moiety Xxx1 (e.g., 2H (in which case in some embodiments the ligand is a primary amine), an alkyl group and an H (in which case in some embodiments the ligand is a secondary amine), or two alkyl groups (in which case the ligand is a tertiary amine) or an active agent moiety); and B is any chemical entity covalently bonded to the terminal carbonyl group of the C-terminal amino acid residue of the cyclic peptide moiety Xxx9 (e.g., —OH (in which case the ligand is a free acid), an alkoxy group (in which case the ligand is an ester), an amine (in which case the ligand is a C-terminal amide), an active agent moiety). In FIG. 13, each of Xxx2, Xxx3, Xxx4, Xxx5, Xxx7 and Xxx8 is independently either present or absent, and when present represents an amino acid residue, with the proviso that at least 4 of Xxx2, Xxx3, Xxx4, Xxx5, Xxx7 and Xxx8 are present.

With regard to the embodiment of a synthetic Somatostatin receptor ligand of SEQ ID NO:68 and the embodiment depicted in FIG. 13, the cyclic peptide moiety has 4, 5, 6 or 7 internal amino acid residues between the sulfur-containing N-terminal and C-terminal amino acid residues (Xxx1 and Xxx9, respectively), one of which internal amino acid residues (Xxx6 in the embodiment depicted in FIG. 13) includes a side chain functional group having a nitrogen atom. The other 3, 4, 5 or 6 internal amino acid residues are any suitable combination of amino acid residues that together with the other amino acid residues render the peptide moiety a Somatostatin ligand, including residues of L- and D-isomers of the 23 proteinogenic amino acids ("natural" amino acids) as well as non-proteinogenic amino acids.

As noted above, for SEQ ID NO:68 each one of Xxx2, Xxx3, Xxx4, Xxx5, Xxx7 and Xxx8 is independently either present or absent, and if present represents an amino acid residue, wherein at least 3 of Xxx2, Xxx3, Xxx4, Xxx5, Xxx7 and Xxx8 are present. For example, when the receptor ligand has 4 internal amino acid residues, three of Xxx2, Xxx3, Xxx4, Xxx5, Xxx7 and Xxx8 are absent, when the receptor ligand has 5 internal amino acid residues, two of Xxx2, Xxx3, Xxx4, Xxx5, Xxx7 and Xxx8 are absent; when the receptor ligand has 6 internal amino acid residues, one of Xxx2, Xxx3, Xxx4, Xxx5, Xxx7 and Xxx8 are absent; and when the receptor ligand has 7 internal amino acid residues, all of Xxx2, Xxx3, Xxx4, Xxx5, Xxx7 and Xxx8 are present.

In some embodiments, the cyclic peptide moiety is bonded to a solid-phase peptide synthesis (SPPS) support, e.g., glass support, cellulose fiber support, polystyrene support, polyacrylamide support, polyethylene glycol support.

In some embodiments, the cyclic peptide moiety (bonded to a SPPS support or not bonded to an SPSS support) includes one or more protecting groups on the functional groups of the peptide moiety. A person having ordinary skill in the art is able to select and add suitable protecting groups to functional groups, upon perusal of the specification and, if necessary, consultation with standard chemical synthesis literature. Suitable protecting groups include t-Boc, Fmoc, benzyloxy-carbonyl (Z), Alloc, benzyl and tert-butyl.

Internal Amino Acid Residue with Side Chain Nitrogen

The internal amino acid residue with the nitrogen atom (Xxx6 in the embodiment depicted in FIG. 13) is any suitable amino acid residue.

In some embodiments, the internal amino acid residue with the nitrogen atom is a residue selected from the group consisting of Lys, Orn, Arg, LysAc, and Homo-Lys. In embodiments that relate to the second aspect of the teachings herein, there is an active agent moiety covalently bonded to the nitrogen atom of the side chain thereof.

The covalent bond between the cyclic peptide moiety and the active agent moiety that is covalently bonded to the nitrogen atom is any suitable bond. In some embodiments, the covalent bond between the cyclic peptide moiety and the active agent moiety is selected from the group of bonds consisting of:
  an amide bond, e.g., formed by the coupling reaction of a primary or secondary amine of the internal amino acid residue with an acid or ester function of the active agent moiety precursor;

an imine bond, e.g., formed by the coupling reaction of a primary or secondary amine of the internal amino acid residue with a ketone or aldehyde function of the active agent moiety precursor;

an amine bond, e.g., formed by an amine-alkylation reaction of a primary or secondary amine of the internal amino acid residue with an alkyl halide function of the active agent moiety precursor;

a sulfamide bond, e.g., formed by a coupling reaction of a primary or secondary amine of the internal amino acid residue with a sulfonyl chloride function of the active agent moiety precursor; and a phosphamide bond, e.g., formed by a coupling reaction of a primary or secondary amine of the internal amino acid residue with a phophoryl chloride function of the active agent moiety precursor.

In some embodiments, the internal amino acid residue is an Arg residue, and the active agent moiety is covalently bonded to a nitrogen atom of side chain thereof. Any suitable chemistry may be used in implementing such embodiments, for example acylation, in some embodiments using dicarbonyls, vicinal diketones or glyoxals.

Terminal Amino Acid Residues

As noted above, in some embodiments according to the first aspect of the teachings herein, the cyclic peptide moiety (such as the set forth in SEQ ID NO:68) has an N-terminal amino acid residue and a C-terminal amino acid residue (Xxx1 and Xxx9), both the N-terminal amino acid residue and the C-terminal amino acid residue having a sulfur-containing functional group, mutually covalently bonded through a sulfur-sulfur bond, thereby cyclizing the peptide moiety.

The N-terminal amino acid residue and the C-terminal amino acid residue are any suitable amino acid residue having a sulfur-containing functional group that are mutually covalently bonded to cyclize the peptide moiety through a sulfur-sulfur bond. In some embodiments, the N-terminal amino acid residue and the C-terminal amino acid residue of the cyclic peptide moiety are independently selected from the group consisting of Cys, H-Cys (homo cysteine), D-Cys and GlyS2.

Active Agent

As noted above, embodiments of a Somatostatin receptor ligand according to the second aspect of the teachings herein comprise an active agent moiety (Q in the embodiment depicted in FIG. 13) covalently bonded to the cyclic peptide moiety such as set forth in SEQ ID NO:68 through the nitrogen atom of the functional group of the internal amino acid residue, where the active agent moiety is selected from the group consisting of: an imaging moiety, a therapeutic moiety, a dye, a fluorescent moiety, a toxin, a chelator, a moiety with a metal atom, a moiety with a radioactive atom, a nanoparticle, an ethylene glycol polymer, a photosensitizer, a liposome constituent and a micelle constituent. It is important to note that in some instances a single active agent moiety falls within the definition of two or more elements of the above group, for example: in some embodiments an active agent moiety is a nanoparticle and an ethylene glycol polymer and either or both of a therapeutic/imaging agent moiety; in some embodiments an active agent moiety is a dye, and/or fluorescent moiety and/or a photosensitizer and either or both of a therapeutic/imaging agent moiety; in some embodiments an active agent moiety includes a radioactive atom and falls within one or more of the other definitions.

In some embodiments, during use of a synthetic Somatostatin receptor ligand according to the teachings herein, the ligand preferentially (or even selectively) binds to a cell expressing or overexpressing a Somatostatin receptor, in some embodiments at least partially due to the affinity of the cyclic peptide moiety to a Somatostatin receptor, which in some embodiments is followed by internalization of the ligand into the cell. Such preferential or selective binding to the cell concentrates the active agent on or in the cell, which subsequently has a desired effect that depends on the nature of the active agent.

N-Terminus of Cyclic Peptide Moiety

As noted above, in some embodiments the cyclic peptide moiety of a Somatostatin receptor ligand according to the teachings herein includes an N-terminal amino acid having a sulfur-containing functional group (e.g., Xxx1 in embodiments described by SEQ ID NO: 68 and embodiments depicted in FIG. 13).

In some embodiments, the nitrogen atom of the N-terminus of the N-terminal amino acid (e.g., the terminal nitrogen atom of Xxx1 in embodiments described by SEQ ID NO: 68 and embodiments depicted in FIG. 13) is selected from the group consisting of a primary amine, a secondary amine and a tertiary amine.

In some embodiments, there is a chemical entity (represented by B' in the embodiment depicted in FIG. 13) covalently bonded to the N-terminal amino acid, in some embodiments, through the terminal nitrogen, which chemical entity completes the valency thereof. In some embodiments, the chemical entity (e.g., B') is covalently bonded to the N-terminal amino acid through the terminal nitrogen with a bond selected from the group consisting of an amide bond, an imine bond, an amine bond, a sulfamide bond and a phosphamide bond. In some embodiments, the chemical entity bonded to the N-terminal amine of the N-terminal amino acid of the peptide moiety of the Somatostatin receptor ligand according to the second aspect is bonded to any suitable chemical entity, e.g., one or two H atoms, one or two alkyl groups, one or two active agent moieties (as detailed hereinbelow), and combinations thereof. In some embodiments, the nitrogen atom of the N-terminal amino acid of the peptide moiety is selected from the group consisting of a primary amine, a secondary amine and a tertiary amine. In some embodiments, there is a chemical entity covalently bonded to the N-terminal amino acid of the peptide moiety of the Somatostatin receptor ligand, in some embodiments, through the terminal nitrogen thereof.

In some embodiments, the chemical entity (e.g., B' in the embodiment depicted in in FIG. 13) comprises an amino acid or peptide chain so that the Somatostatin receptor ligand further comprises an amino acid residue or a peptide chain covalently bonded to the N-terminal amino acid, typically with an amide bond.

In some embodiments, the Somatostatin receptor ligand according to the second aspect of the teachings herein further comprises an active agent moiety covalently bonded to the N-terminal amino acid residue of the cyclic peptide moiety in addition to the active agent moiety bonded to the internal amino acid side chain. In the embodiment depicted in FIG. 13, such an additional active agent moiety is or constitutes a portion of B'. In some embodiments, such an active agent moiety is bonded directly to the N-terminal amino acid. In some embodiments, such an active agent moiety is bonded indirectly to the N-terminal amino acid, e.g., through a linker (e.g., GABA (gamma-aminobutyric acid), an amino acid, a peptide chain). Any suitable active agent moiety may be used in implementing such embodiments. In some such embodiments, the active agent moiety is selected from the group consisting of an imaging moiety, a therapeutic moiety, a dye, a fluorescent moiety, a toxin, a chelator, a moiety with a metal atom, a moiety with a radioactive atom, a nanoparticle, an ethylene glycol polymer, photosensitizer, a liposome constituent and a micelle constituent, substantially as discussed above. In some embodiments, an active agent bonded to the N-terminal amino acid residue is of a different type from the active agent bonded to the internal amino acid residue, e.g., one therapeutic and one imaging. In some embodiments, an active agent bonded to the N-terminal amino acid residue is of the same type as the active agent bonded to the internal amino acid residue, e.g., both imaging or both therapeutic. In some embodiments, an active agent bonded to the N-terminal amino acid residue is substantially the same as the active agent bonded to the internal amino acid residue.

C-Terminus of Cyclic Peptide Moiety

As noted above, in some embodiments of the cyclic peptide moiety of a Somatostatin receptor ligand according to the teachings herein includes a C-terminal amino acid residue having a sulfur-containing functional group (e.g., Xxx9 in embodiments described by SEQ ID NO:68 and embodiments depicted in FIG. 13).

In some embodiments, the end of the C-terminal amino acid residue is selected from the group consisting of a free acid, an acid salt, an ester and an amide.

In some embodiments of the second aspect according to the teachings herein, there is a chemical entity (that is represented by B in the embodiment depicted in FIG. 13) covalently bonded to the C-terminal amino acid residue, especially through the terminal carbonyl group which chemical entity completes the valency thereof. In some embodiments, the chemical entity is covalently bonded to the C-terminal amino acid residue through the terminal carbonyl group with a bond selected from the group consisting of an amide bond. Any suitable chemistry can be used in implementing such embodiments, for example, carbodiimide chemistry.

The chemical entity covalently bonded to the C-terminal amino acid residue is any suitable chemical entity bonded to complete the valency of the C-terminal amino acid residue.

In some embodiments, the chemical entity bonded to the C-terminal amino acid residue comprises at least one amino acid residue that is directly bonded with a peptide bond to the C-terminal carbonyl of the C-terminal amino acid residue. In some embodiments, the chemical entity comprises at least two, at least four and even at least eight amino acid residues. Accordingly, in some embodiments, the chemical moiety is an amino acid or peptide chain so that the Somatostatin receptor ligand further comprises an amino acid residue or a peptide chain covalently bonded to the C-terminal amino acid, typically with an amide bond.

In some embodiments, the portion of the chemical entity that is directly bonded to the C-terminal carbonyl of the C-terminal amino acid residue is not an amino acid residue. For example, in some embodiments, the chemical entity is selected from the group consisting of: —OH (in which case the receptor ligand is a free acid), —O⁻M⁺ (in which case the receptor ligand is an acid salt), an alkoxy group (in which case the receptor ligand is an ester), an amine (in which case the receptor ligand is a C-terminal amide), an active agent moiety (as detailed hereinbelow), an entity comprising an amino acid residue (that is not directly bonded to the Pjhe residue), an entity comprising —OH, an entity comprising —O⁻M⁺, an entity comprising an alkoxy group, an entity comprising an amine, an entity comprising an active agent moiety and combinations thereof.

In some embodiments, the Somatostatin receptor ligand according to the second aspect of the teachings herein further comprises an active agent moiety covalently bonded to the C-terminal amino acid residue of the cyclic peptide moiety, in addition to the active agent moiety bonded to the internal amino acid side chain and the optional active agent moiety bonded to the N-terminal amino acid. In the embodiment depicted in FIG. 13, such an additional active agent moiety is or constitutes a portion of B. In some embodiments, such an active agent moiety is bonded directly to the C-terminal amino acid. In some embodiments, such an active agent moiety is bonded indirectly to the C-terminal amino acid, e.g., through a linker (e.g., GABA (gamma-aminobutyric acid), an amino acid, a peptide chain). Any suitable active agent moiety may be used in implementing such embodiments. In some such embodiments, the active agent moiety is selected from the group consisting of an imaging moiety, a therapeutic moiety, a dye, a fluorescent moiety, a toxin, a chelator, a moiety with a metal atom, a moiety with a radioactive atom, a nanoparticle, an ethylene glycol polymer, photosensitizer, a liposome constituent and a micelle constituent, substantially as discussed above. In some embodiments, an active agent bonded to the C-terminal amino acid residue is of a different type from the active agent bonded to the internal amino acid residue, and/or the active agent bonded to the N-terminal amino acid residue if present. In some embodiments, an active agent bonded to the C-terminal amino acid residue is of the same type as the active agent bonded to the internal amino acid residue, and/or the active agent bonded to the N-terminal amino acid residue if present. In some embodiments, an active agent bonded to the C-terminal amino acid residue is substantially the same as the active agent bonded to the internal amino acid residue, and/or the active agent bonded to the N-terminal amino acid residue if present.

Other Internal Amino Acid Residues

As noted above, the cyclic peptide moiety according to the second aspect of the teachings herein (such as having an amino acid residue sequence set forth in SEQ ID NO:68) has 4, 5, 6 or 7 internal amino acid residues between the sulfur-containing N-terminal and C-terminal amino acid residues, one of which internal amino acid residues includes a side chain functional group having a nitrogen atom. The other 3, 4, 5 or 6 internal amino acid residues are any suitable combination of amino acid residues that together with the other amino acid residues render the Somatostatin receptor ligand a Somatostatin ligand, including residues of L- and D-isomers of the 23 proteinogenic amino acids as well as non-proteinogenic amino acids.

As noted above, in some embodiments including embodiments described by SEQ ID NO:68 and/or depicted in FIG. 13, each of Xxx2, Xxx3, Xxx4, Xxx5, Xxx7 and Xxx8 independently is either present or absent and, if present, represent an amino acid residue, wherein at least 4 of Xxx2, Xxx3, Xxx4, Xxx5, Xxx7 and Xxx8 are present. When the receptor ligand has 4 internal amino acid residues, three of Xxx2, Xxx3, Xxx4, Xxx5, Xxx7 and Xxx8 are absent, when the receptor ligand has 5 internal amino acid residues, two of Xxx2, Xxx3, Xxx4, Xxx5, Xxx7 and Xxx8 are absent; when the receptor ligand has 6 internal amino acid residues, one of Xxx2, Xxx3, Xxx4, Xxx5, Xxx7 and Xxx8 are absent; and when the receptor ligand has 7 internal amino acid residues, all of Xxx2, Xxx3, Xxx4, Xxx5, Xxx7 and Xxx8 are present.

In some embodiments, a second of the internal amino acid residues is selected from the group consisting of Tyr and Phe and a third one of the internal amino acid residues is selected from the group consisting of Trp and DTrp (e.g., Lanreotide (SEQ ID NO:4); Octreotide (SEQ ID NO:5); Compounds 1-12, 14-16 (Table 1 below); cyclic peptide Somatostatin analogues that have been synthesized and disclosed by one of the present Inventors in U.S. Pat. No. 7,700,717: compound 30 (GlyS2*-Phe-Trp-DTrp-Lys-Thr-Phe-GlyS2*-NH₂ 'SEQ ID NO:69, disclosed in U.S. Pat. No. 7,700,717, designated 3213); and compound 31 (DPhe-GlyS2*-Phe-Trp-DTrp-Lys-Thr-Phe-GlyS2*-NH₂ SEQ ID NO:70, disclosed in U.S. Pat. No. 7,700,717, designated 3173). It is important to note that in some embodiments, the second and/or third aspect of the teachings herein is implemented by providing one of the above-listed compounds (e.g., Lanreotide, Octreotide, Compounds 1-12, 14-16, 30 or 31 or variants such as salts, esters, functional-group protected and/or resin-bound variants thereof) and covalently bonding an active agent moiety to the peptide moiety, particularly through a nitrogen atom of a functional group of an internal amino acid residue. In some such embodiments, a further internal amino acid residue is selected from the group consisting of Trp and Phe, especially Trp (e.g., Compounds 1, 3, 4, 8, 11, 12, 14-16, 30, 31). In some such embodiments, a further internal amino acid residue is Arg (e.g., Compounds 8-10).

In some embodiments, a second of the internal amino acid residues is selected from the group consisting of Tyr and Phe, a third one of the internal amino acid residues is selected from the group consisting of Trp and DTrp, and a fourth one of the internal amino acid residues is Phe (e.g., Compounds 1-12, 14-16 and 30-31). In some such embodiments, a further internal amino acid residue is selected from the group consisting of Trp and Phe, especially Trp (e.g., Compounds 1, 3, 4, 8, 11, 12, 14-16, 30, 31). In some such embodiments, a further internal amino acid residue is Arg (e.g., Compounds 8-10).

In some embodiments, a second of the internal amino acid residues is selected from the group consisting of Tyr and Phe, a third one of the internal amino acid residues is selected from the group consisting of Trp and DTrp, and an additional one of the internal amino acid residues is Thr (e.g., Compounds 1-12, 14-16 and 30-31). In some such embodiments, a further internal amino acid residue is selected from the group consisting of Trp and Phe, especially Trp (e.g., Compounds 1, 3, 4, 8, 11, 12, 14-16, 30, 31). In some such embodiments, a further internal amino acid residue is Arg (e.g., Compounds 8-10).

In some embodiments, a second of the internal amino acid residues is selected from the group consisting of Tyr and Phe, a third one of the internal amino acid residues is selected from the group consisting of Trp and DTrp, a fourth one of the internal amino acid residues is Phe and a fifth one of the internal amino acid residues is Thr (e.g., Compounds 1-12, 14-16 and 30-31). In some such embodiments, a further internal amino acid residue is selected from the group consisting of Trp and Phe, especially Trp (e.g., Compounds 1, 3, 4, 8, 11, 12, 14-16, 30, 31). In some such embodiments, a further internal amino acid residue is Arg (e.g., Compounds 8-10).

In some embodiments, a second of the internal amino acid residues is Phe and a third one of the internal amino acid residues is Thr (e.g., Compounds 1-12, 14-16 and 30-31). In some such embodiments, a further internal amino acid residue is selected from the group consisting of Trp and Phe, especially Trp (e.g., Compounds 1, 3, 4, 8, 11, 12, 14-16, 30, 31). In some such embodiments, a further internal amino acid residue is Arg (e.g., Compounds 8-10).

In some embodiments, the cyclic peptide moiety has the sequence:

(SEQ ID NO: 68)
-Xxx1*-Xxx2-Xxx3-Xxx4-Xxx5-Xxx6-Xxx7-Xxx8-Xxx9*- wherein Xxx1 is the N-terminal amino acid residue,
Xxx9 is the C-terminal amino acid residue;
the asterisks indicate cyclization by an S—S bond, and
each of Xxx2-Xxx8 is independently present or absent and if present is an internal amino acid, wherein at least 4 of Xxx2-Xxx8 are present.

In some embodiments, the Xxx6 is the internal amino acid residue including the side chain functional group having a nitrogen atom. In some such embodiments, the Xxx6 is selected from the group consisting of Lys (e.g., Lanreotide, Octreotide, Compounds 1, 2, 4, 6, 8-12, 30-31), Orn (e.g., Compounds 3, 5, 7), Homo-Lys (e.g., Compound 16) and Arg (e.g., Compounds 15).

In some embodiments, the Xxx2 is selected from the group consisting of Arg (e.g., Compounds 1-7, 11, 12, 14-16, 30, 31) or is not present (e.g., Compounds 8-10).

In some embodiments, the Xxx3 is selected from the group consisting of Tyr (e.g., Lanreotide, Compounds 4, 6, 7) and Phe (e.g., Octreotide, Compounds 1-3, 5, 8-12, 14-16, 30-31).

In some embodiments, the Xxx4 is selected from the group consisting of Trp (e.g., Compounds 1, 3, 4, 11, 12, 14-16, 30, 31), Phe (e.g., Compounds 8), and not present (e.g., Lanreotide, Octreotide, Compounds 2, 5-7, 9, 10).

In some embodiments, the Xxx5 is selected from the group consisting of Trp (e.g., Lanreotide) and DTrp (e.g., Octreotide, Compounds 1-12, 14-16, 30, 31).

In some embodiments, the Xxx7 is selected from the group consisting of Thr (Compounds 1-12, 14-16, 30, 31) and not present (e.g., Lanreotide, Octreotide).

In some embodiments, the Xxx8 is selected from the group consisting of Val (e.g., Lanreotide), Thr (e.g., Octreotide) and Phe (e.g., Compounds 1-12, 14-16, 30, 31).

In some embodiments, the Somatostatin receptor ligand according to the teachings herein is selected from the group consisting of Lantreotide, Octreotide and compounds 1, 2, 4, 6, 8, 9, 10, 11, 12, 14, 30 and 31 covalently bonded to the active agent moiety through the nitrogen atom of the Lys amino acid residue of the respective cyclic peptide moiety.

In some embodiments, the Somatostatin receptor ligand according to the teachings herein is selected from the group consisting of compounds 3, 5 and 7 covalently bonded to the active agent moiety through the nitrogen atom of the Orn amino acid residue of the respective cyclic peptide moiety.

In some embodiments, the Somatostatin receptor ligand according to the teachings herein is Compound 15 covalently bonded to the active agent moiety through the nitrogen atom of the Arg amino acid residue of the respective cyclic peptide moiety of Compound 15.

In some embodiments, the Somatostatin receptor ligand according to the teachings herein is Compound 16 covalently bonded to the active agent moiety through a nitrogen atom of a Homo-Lys amino acid residue of the cyclic peptide moiety of Compound 16.

Third Aspect

In addition to the described above, there is also provided a synthetic Somatostatin receptor ligand that includes a nanoparticle active agent moiety according to the third aspect of the teachings herein. Thus, according to an aspect of some embodiments of the teachings herein, there is also provided a synthetic Somatostatin receptor ligand, comprising:

a cyclic peptide moiety;
the cyclic peptide moiety consisting of from 6 to 9 amino acid residues, including an N-terminal amino acid residue, a C-terminal amino acid residue and 4, 5, 6 or 7 internal amino acid residues therebetween;
each of the N-terminal amino acid residue and the C-terminal amino acid residue having a sulfur-containing functional group, mutually covalently bonded through a sulfur-sulfur bond, thereby cyclizing the peptide moiety;
optionally wherein at least one of the 4, 5, 6 or 7 internal amino acid residues includes a side chain functional group having a nitrogen atom; and
covalently bonded to the cyclic peptide moiety, a nanoparticle active agent moiety and salts, esters and amides thereof. In some embodiments, the internal amino acid residue including a side chain functional group having a nitrogen atom is selected from the group consisting of Lys, Orn and HomoLys.

In some embodiments, the nanoparticle active agent moiety is covalently bonded to the nitrogen atom of the side chain of the internal amino acid residue, directly or indirectly (that is to say, optionally comprising at least one intervening atom that functions as a linker). Such embodiments are also embodiments of the second aspect of the teachings herein.

In some embodiments, the nanoparticle active agent moiety is covalently bonded to the N-terminal amino acid residue of the cyclic peptide moiety, directly or indirectly (that is to say, optionally comprising at least one intervening atom that functions as a linker).

In some embodiments, the nanoparticle active agent moiety is covalently bonded to the C-terminal amino acid residue of the cyclic peptide moiety, directly or indirectly (that is to say optionally comprising at least one intervening atom that functions as a linker).

In some embodiments, a linker comprises at least one amino acid residue.

In some embodiments, the covalent bond between the cyclic peptide moiety and the nanoparticle active agent moiety is selected from the group of bonds consisting of: an amide bond, an imine bond, an amine bond, a sulfamide bond, a phosphamide bond and an acyl bond.

In some embodiments, the N-terminal amino acid residue and the C-terminal amino acid residue of the cyclic peptide moiety are independently selected from the group consisting of Cys, H-Cys, D-Cys and GlyS2.

In some embodiments, the Somatostatin receptor ligand further comprises at least one amino acid residue covalently bonded to the N-terminal amino acid.

In some embodiments, the Somatostatin receptor ligand further comprises at least one amino acid residue covalently bonded to the C-terminal amino acid.

In some embodiments, the Somatostatin receptor ligand further comprises a second active agent moiety different from the nanoparticle active agent moiety covalently bonded to the cyclic peptide moiety. In some embodiments, the second active agent moiety is covalently bonded to the cyclic peptide moiety through the C-terminal amino acid residue of the cyclic peptide moiety, through the N-terminal amino acid residue of the cyclic peptide moiety, or through the nitrogen atom of the side chain of the internal amino acid residue, directly or indirectly (optionally comprising at least one intervening atom that functions as a linker). In some embodiments, the second active agent moiety is selected from the group consisting of: an imaging moiety, a therapeutic moiety, a dye, a fluorescent moiety, a toxin, a chelator, a moiety with a metal atom, a moiety with a radioactive atom, a nanoparticle, an ethylene glycol polymer, photosensitizer, a liposome constituent and a micelle constituent.

In some embodiments, the Somatostatin receptor ligand further comprises a third active agent moiety different from the nanoparticle active agent moiety covalently bonded to the cyclic peptide moiety. In some embodiments, the third active agent moiety is covalently bonded to the cyclic peptide moiety through the C-terminal amino acid residue of the cyclic peptide moiety, through the N-terminal amino acid residue of the cyclic peptide moiety, or through the nitrogen atom of the side chain of the internal amino acid residue, directly or indirectly (optionally comprising at least one intervening atom that functions as a linker). In some embodiments, the third active agent moiety is selected from the group consisting of: an imaging moiety, a therapeutic moiety, a dye, a fluorescent moiety, a toxin, a chelator, a moiety with a metal atom, a moiety with a radioactive atom, a nanoparticle, an ethylene glycol polymer, photosensitizer, a liposome constituent and a micelle constituent.

Other specific embodiments, details and options of the Somatostatin receptor ligands according to the third aspect (e.g., of the amino acid residues that make up the cyclic peptide moiety, chemical entities bonded to the N-terminal amino acid to complete the valency thereof, chemical entities bonded to the C-terminal amino acid to complete the valency thereof, are as described hereinabove with reference to the second aspect of the teachings herein with necessitated changes, but are not repeated here in the interest of brevity.

Active Agent Moieties

As discussed hereinabove, in some embodiments of the first, second and/or third aspect of the teachings the Somatostatin receptor ligand comprises at least one active agent moiety. Any suitable active agent moiety, having any suitable property or properties may be used in implementing the teachings herein.

Size of Active Agent Moiety

The size of the active agent moiety is any suitable size. That said, in some embodiments, the active agent moiety has a molecular weight of not less than 250, not less than 500, not less than 750, not less than 1000, not less than 2000, not less than 4000, not less than 8000, and even not less than 16000.

Imaging Moiety

In some embodiments, the active agent moiety is an imaging moiety, that is to say, is an agent that is distinctly observable when concentrated in a cell under suitable conditions and/or when using a suitable imaging modality.

Any suitable imaging moiety may be used in implementing the teachings herein. Typical imaging moieties include moieties having a distinct color allowing visual identification, moieties having distinct fluorescence allowing visual identification under appropriate lighting conditions, or positron emitters allowing imaging by Positron Emission Tomography.

In some such embodiments, subsequent to administration of the Somatostatin receptor ligand to cells, the imaging moieties become concentrated in cells expressing Somatostatin receptor to a greater degree than others, allowing identification of such cells. A typical utility of such embodiments is to differentiate between normal cells and pathological cells overexpressing Somatostatin receptors.

Therapeutic Moiety

In some embodiments, the active agent moiety is a therapeutic moiety, that is to say when concentrated in a cell the active agent moiety has some desired pharmacological effect, typically including helping a targeted cell develop or attenuating growth of or killing a targeted cell, for example when the targeted cell is pathological.

Any suitable therapeutic moiety may be used in implementing the teachings herein, for example, a toxin, a vitamin and a photosensitizer. Typical therapeutic moieties include moieties that are cytotoxic when concentrated in a cell, for example by influencing cell processes or free radical or radiation damage.

In some such embodiments, subsequent to administration of the Somatostatin receptor ligand to cells, the therapeutic moieties become concentrated in cells expressing Somatostatin receptors (e.g., especially cells overexpressing Somatostatin receptors), to a greater degree than cells not expressing Somatostatin receptors or cells expressing low levels of Somatostatin receptors allowing specific targeting and treatment of such cells. A typical utility of such embodiments is to administer a cell-killing active agent to pathological cells overexpressing Somatostatin receptors (e.g., some cancers) while causing little or no damage to normal cells.

Dye

In some embodiments, the active agent moiety is a dye, that is to say, is an active agent moiety that includes a chromophore having a distinct color that can be observed at sufficient concentration.

Any suitable dye with any suitable chromophore may be used in implementing the teachings herein, for example, derivatives of methyl violet.

In some such embodiments, subsequent to administration of the Somatostatin receptor ligand to cells (in vivo or in vitro), the dyes become concentrated in cells expressing Somatostatin receptors to a greater degree than others (e.g., especially cells overexpressing Somatostatin receptors), allowing identification of such cells by visual or microscopic inspection.

Fluorescent Agent

In some embodiments, the active agent moiety is fluorescent, that is to say, is an active agent moiety that includes a fluorophore that absorbs energy at a first wavelength of light, and then emits at least some of the energy at a second wavelength of light higher than the first.

Any suitable fluorescent agent with any suitable fluorophore may be used in implementing the teachings herein, for example, derivatives of fluorescein or rhodamine.

In some such embodiments, subsequent to administration of the Somatostatin receptor ligand to cells (in vivo or in vitro), the fluorescent agents become concentrated in cells expressing Somatostatin receptors to a greater degree than others (e.g., especially cells overexpressing Somatostatin receptors), allowing identification of such cells due to the distinct fluorescence of the fluorophore.

In some such embodiments, the Somatostatin receptor ligands are selected from the group consisting of: Compound 2, 3, 4, 5, 6, 7, 8, 9, 10, 11, 12, 13, 14, 15 and 16 (SEQ ID NOS: 12, 17, 21, 25, 30, 35, 39, 45, 46, 50, 52, 54, 58, 62, and 64, respectively) that include a FITC-GABA active agent moiety.

Toxin

In some embodiments, the active agent moiety is a toxin, that is to say, is an active agent that has a deleterious effect on cells, for example, by disrupting biological processes in the cell, for example by attenuating or stopping cell development (e.g., cytostatic) or even killing the cell (e.g., cytotoxic).

In some such embodiments, subsequent to administration of the Somatostatin receptor ligand to cells, the toxin becomes concentrated in cells expressing Somatostatin receptors to a greater degree than others, e.g., especially cells overexpressing Somatostatin receptors, thereby having a deleterious effect on the cells.

Any suitable toxin may be used in implementing the teachings herein, for example, derivatives of actinomycin, camptothecin, doxorubicin, gentamicin. Some such embodiments can be used in vivo to damage or kill cells overexpressing one or more Somatostatin receptor.

Chelator

In some embodiments, the active agent moiety is a chelator, that is to say, is an active agent configured to bind metal ions by chelation. Any suitable chelator may be used in implementing the teachings herein, for example derivatives of DOTA (1,4,7,10-tetraazacyclododecane-1,4,7,10-tetraacetic acid), NOTA (2-(4,7-bis(2-(tert-butoxy)-2-oxoethyl)-1,4,7-triazonan-1-yl) acetic acid), NODA (4-(4,7-bis(2-(tert-butoxy)-2-oxoethyl)-1,4,7-triazacyclononan-1-yl)-5-(tert-butoxy)-5-oxopentanoic acid) or EDTA (ethylenediaminetetraacetic acid). In some such embodiments, the active agent moiety is a chelator that is chelating a metal, in some embodiments a radioactive or MRI detectable metal, see below.

In some embodiments, subsequent to administration of the Somatostatin receptor ligand to cells, the chelator (depending on the embodiment, with or without chelated metal) become concentrated in cells expressing one or more Somatostatin receptors to a greater degree than others, e.g., especially cells overexpressing Somatostatin receptors.

Some such embodiments can be used to concentrate metal ions (in some embodiments MRI-detectable metals, or/and radioactive metal ions) in cells overexpressing one or more Somatostatin receptor, e.g., for imaging and/or therapeutic purposes.

Moiety with a Metal Atom

In some embodiments, the active agent moiety is a moiety with a metal atom. Some such embodiments can be used to concentrate metal atoms in cells overexpressing Somatostatin receptors.

For example, in some embodiments the metal atom is a radioactive metal atom, and the Somatostatin is for use as a radiopharmaceutical in the field of nuclear medicine, e.g., for therapeutic and/or imaging purposes, see below.

For example, in some embodiments the metal atom is an MRI-detectable metal atom (e.g., Gadolinium, Fe2+) for use as an MRI contrasting agent in the field of magnetic resonance imaging, e.g., for imaging purposes.

Moiety with Radioactive Atom

In some embodiments, the active agent moiety is a moiety with a radioactive atom. Some such embodiments can be used to concentrate radioactive atoms in cells overexpressing one or more Somatostatin receptor, for example, for use as a radiopharmaceutical in the field of nuclear medicine, e.g., for therapeutic and/or imaging purposes.

In some such embodiments, subsequent to administration of the Somatostatin receptor ligand to cells, the radioactive atoms become concentrated in cells expressing one or more Somatostatin receptor to a greater degree than others (e.g., especially cells overexpressing one or more Somatostatin receptors), allowing identification of such cells with radiation-detecting moieties (e.g., PET/SPECT) and/or having a therapeutic (e.g., toxic) effect due to emitted radiation.

Any suitable moiety with any suitable radioactive agent may be used in implementing the teachings herein.

In some embodiments, the radioactive atom is covalently bonded to other parts of the active agent moiety. Typical such embodiments include one or more radioactive atoms, for example, atoms selected from the group consisting of iodine-123, iodine-125, iodine-131 in a iobenguane residue, fluorine-18, carbon-11, carbon-14, tritium, nitrogen-13, oxygen-15 and phosphorous-32.

In some embodiments, the radioactive agent is a radioactive metal atom ionically bonded (e.g., chelated) to other parts of the active the active agent moiety. Typical such embodiments include one or more radioactive atoms, for example, atoms selected from the group consisting of technetium-99m, chromium-51, cobalt-57, cobalt-58, erbium-169, gallium-67, gallium-68, indium-111, iron-59, radium-223, rubidium-82, samarium-153, selenium-75, strontium-89, thallium-201 and yttrium-90.

Nanoparticle

In some embodiments, the active agent moiety comprises a nanoparticle, and in some embodiments is a nanoparticle. A person having ordinary skill in the art is familiar with the definition of the term "nanoparticle", see for example, Murthy S K, Int J Nanomedicine 2007, 2(2) 129-141 which is included by reference as if fully set-forth herein, that also includes examples of specific nanoparticles that may be used in implementing the teachings herein. That said, in some embodiments, a nanoparticle is a particle of not less than 1 nanometer in size and not more than 1000 nanometers in size, and in some embodiments not more than 100 nanometers in size.

In some such embodiments, subsequent to administration of the Somatostatin receptor ligand to cells, the nanoparticles moieties become concentrated in cells expressing one or more Somatostatin receptor to a greater degree than others (e.g., especially cells overexpressing one or more Somatostatin receptor), allowing identification of such cells (see experimental section).

In some embodiments, the nanoparticle defines an internal volume containing a secondary active agent (e.g., a therapeutic or imaging agent). In some such embodiments, the nanoparticle is used as a container for delivery of the secondary active agents contained therein into a cell. Some such embodiments are used to deliver large amounts of the secondary active agents to cells overexpressing one or more Somatostatin receptors: once the nanoparticle is internalized in a cell, the secondary active agent is released inside the cell. In some such embodiments, subsequent to administration of the Somatostatin receptor ligand to cells, the nanoparticles moieties become concentrated in cells expressing one or more Somatostatin receptor to a greater degree than others (e.g., especially cells overexpressing one or more Somatostatin receptor), and then release the secondary active agent inside the cell.

Any suitable nanoparticle may be used in implementing the teachings herein, for example, nanoparticles such as described in PCT Publications WO2012/054923, WO2012/166923, WO2014/04361 and WO2014/043625 which are included by reference as if fully set-forth herein, as well as nanoparticles that are substantially albumin clusters.

In some embodiments, the nanoparticle comprises carbon nanotubes, especially single-walled carbon nanotubes. In some embodiments, the carbon nanotubes are (optionally fluorinated and then) modified with branched polyethyleneimine through which the cyclic peptide moiety is covalently bonded. In some embodiments, the carbon nanotube further comprises a therapeutic active agent bonded to the carbon nanotube, for example, through a branched polyethyleneimine. Such embodiments may be implemented by a person having ordinary skill in the art upon perusal of the specification in combination with the teachings of Andreoli E et al, in J. Mater. Chem. B 2014, 2, 4740-4747 which is included by reference as if fully set forth herein.

In some embodiments, the nanoparticle comprises a "nanoflower", for example, formed of a graft copolymer constructed by directly polymerizing gamma-camptothecin-glutamate N-carboxyanhydride (Glu(CPT)-NCA) on multiple sites of poly(ethylene glycol) (PEG)-based main chain via ring open polymerization (ROP). Such embodiments may be implemented by a person having ordinary skill in the art upon perusal of the specification in combination with the teachings of Tai W et al, in J. Biomaterials 2014, 35(25), 7194-7203 which is included by reference as if fully set forth herein.

Ethylene Glycol Polymer

In some embodiments, the active agent moiety comprises an ethylene glycol polymer (polyethylene glycol).

In some such embodiments, the ethylene glycol polymer is a component of a nanoparticle.

In some such embodiments, the peptide moiety of the Somatostatin receptor ligand as described herein is pegylated by the ethylene glycol polymer. Depending on the embodiment, pegylation may have one or more useful attributes including increasing solubility (in vivo and/or in vitro), reducing in vivo immunogenicity and antigenicity, and reducing the rate of renal clearance of the Somatostatin receptor ligand.

Photosensitizer

In some embodiments, the active agent moiety is a photosensitizer. As used herein, a photosensitizer is a molecule that absorbs energy from light to enter an excited state, and in the excited state interacts with triplet oxygen species to produce chemically-active singlet oxygen species. Known photosensitizers include phenothiazines such as Methylene Blue, xanthenes like Rose Bengal and porphyrins.

In some such embodiments, subsequent to administration of the Somatostatin receptor ligand to cells, the photosensitizer moieties become concentrated in cells expressing Somatostatin receptors to a greater degree than others (e.g., especially cells overexpressing one or more Somatostatin receptor). Once the photosensitizers are inside the cell, the cells are irradiated, causing the photosensitizers to generate active oxygen species inside the cell from oxygen molecules present inside the cell, the active oxygen species having a potential cytotoxic effect.

Liposome Constituent

In some embodiments, the active agent moiety is a liposome constituent, e.g., a phospholipid or an ethylene glycol polymer. In some such embodiments, the Somatostatin receptor ligand is used to form a liposome together with other liposome constituents (as known in the art) optionally with secondary active agent contained inside the liposome in analogy to the described with reference to nanoparticles above. In such embodiments, the liposome-constituent active-agent moiety becomes part of the liposome while at least part of the peptide moiety acts as a guiding moiety to preferentially or even selectively bind the liposome to cells that express or overexpress Somatostatin receptors. Some such embodiments are used to deliver liposomes (and in some embodiments, secondary active agents contained therein) into cells overexpressing one or more Somatostatin receptor.

In some such embodiments, subsequent to administration of the Somatostatin receptor ligand to cells, the liposome become concentrated in cells expressing one or more Somatostatin receptors to a greater degree than others (e.g., especially cells overexpressing one or more Somatostatin receptors), and then release the secondary active agent inside the cell.

Micelle Constituent

In some embodiments, the active agent moiety is a micelle constituent, e.g., a surfactant. In some such embodiments, the Somatostatin receptor ligand is used to form a micelle together with other micelle constituents (as known in the art) optionally with secondary active agent contained inside the micelle in analogy to the described with reference to nanoparticles and liposomes above. In such embodiments, the micelle-constituent active-agent moiety becomes part of the micelle while at least part of the peptide moiety acts as a guiding moiety to preferentially or even selectively bind the micelle to cells that express or overexpress one or more Somatostatin receptor. Some such embodiments are used to deliver micelles (and in some embodiments, secondary active agents contained therein) into cells overexpressing one or more Somatostatin receptor.

In some such embodiments, subsequent to administration of the Somatostatin receptor ligand to cells, the micelle become concentrated in cells expressing one or more Somatostatin receptor to a greater degree than others (e.g., especially cells overexpressing one or more Somatostatin receptor), and then release the secondary active agent inside the cell.

Pharmaceutical Composition and Method of Making Pharmaceutical Composition

According to an aspect of some embodiments of the teachings herein, there is also provided a pharmaceutical composition comprising: as an active ingredient, at least one (synthetic) Somatostatin receptor ligand according to one or more of the aspects (e.g., first, second, and/or third) of the teachings herein; and a pharmaceutically acceptable carrier.

According to an aspect of some embodiments of the teachings herein, there is also provided a method of making a pharmaceutical composition comprising: combining at least one (synthetic) Somatostatin receptor ligand according to one or more of the aspects (e.g., first, second and/or third) of the teachings herein; and a pharmaceutically acceptable carrier.

In some embodiments, the pharmaceutical composition is useful in the treatment of a disease or disorder associated with expression of SSTRx. In some embodiments, the pharmaceutical composition and or method includes at least one Somatostatin receptor ligand comprising a peptide moiety that includes the amino acid residue sequence set forth in SEQ ID NO:7. In some embodiments, the pharmaceutical composition and or method includes at least one Somatostatin receptor ligand comprising a peptide moiety that includes the amino acid residue sequence set forth in SEQ ID NO:8. In some embodiments, the pharmaceutical composition and or method includes at least one Somatostatin receptor ligand comprising a peptide moiety that includes the amino acid residue sequence set forth in SEQ ID NO:9. In some embodiments, the pharmaceutical composition and or method includes at least one Somatostatin receptor ligand comprising a peptide moiety that includes the amino acid residue sequence set forth in SEQ ID NO:10. In some embodiments, the pharmaceutical composition and or method includes at least one Somatostatin receptor ligand comprising a peptide moiety that includes the amino acid residue sequence set forth in SEQ ID NO:11.

In some embodiments, the pharmaceutical composition and or method includes at least one Somatostatin receptor ligand comprising a peptide moiety that includes the amino acid residue sequence set forth in any one of SEQ ID NO:12, 13, 14, 15 or 16. In some embodiments, the pharmaceutical composition and or method includes at least one Somatostatin receptor ligand comprising a peptide moiety that includes the amino acid residue sequence set forth in any one of SEQ ID NO:17, 18, 19 or 20. In some embodiments, the pharmaceutical composition and or method includes at least one Somatostatin receptor ligand comprising a peptide moiety that includes the amino acid residue sequence set forth in any one of SEQ ID NO:21, 22, 23 or 24. In some embodiments, the pharmaceutical composition and or method includes at least one Somatostatin receptor ligand comprising a peptide moiety that includes the amino acid residue sequence set forth in any one of SEQ ID NO:25, 26, 27, 28 or 29. In some embodiments, the pharmaceutical composition and or method includes at least one Somatostatin receptor ligand comprising a peptide moiety that includes the amino acid residue sequence set forth in any one of SEQ ID NO:30, 21, 32, 33 or 34. In some embodiments, the pharmaceutical composition and or method includes at least one Somatostatin receptor ligand comprising a peptide moiety that includes the amino acid residue sequence set forth in any one of SEQ ID NO:35, 36, 37 or 38. In some embodiments, the pharmaceutical composition and or method includes at least one Somatostatin receptor ligand comprising a peptide moiety that includes the amino acid residue sequence set forth in any one of SEQ ID NO:39, 40, 41, 42, 43 or 44. In some embodiments, the pharmaceutical composition and or method includes at least one Somatostatin receptor ligand comprising a peptide moiety that includes the amino acid residue sequence set forth in any one of SEQ ID NO:45, 46, 47, 48 or 49. In some embodiments, the pharmaceutical composition and or method includes at least one Somatostatin receptor ligand comprising a peptide moiety that includes the amino acid residue sequence set forth in any one of SEQ ID NO:50 or 51. In some embodiments, the pharmaceutical composition and or method includes at least one Somatostatin receptor ligand comprising a peptide moiety that includes the amino acid residue sequence set forth in any one of SEQ ID NO:52, 53, 54, 55, 56 or 57. In some embodiments, the pharmaceutical composition and or method includes at least one Somatostatin receptor ligand comprising a peptide moiety that includes the amino acid residue sequence set forth in any one of SEQ ID NO:58, 59, 60, or 61. In some embodiments, the pharmaceutical composition and or method includes at least one Somatostatin receptor ligand comprising a peptide moiety that includes the amino acid residue sequence set forth in any one of SEQ ID NO:62 or 63. In some embodiments, the pharmaceutical composition and or method includes at least one Somatostatin receptor ligand comprising a peptide moiety that includes the amino acid residue sequence set forth in any one of SEQ ID NO:64, 65, 66 or 67. In some embodiments, the pharmaceutical composition and or method includes at least one Somatostatin receptor ligand comprising a peptide moiety that includes the amino acid residue sequence set forth in SEQ ID NO:68.

The pharmaceutical composition and methods of making such a composition are in accordance to the known in the art of pharmacology using by any suitable method or combination of methods as known in the art such as described in "Remington's Pharmaceutical Sciences," Mack Publishing Co., Easton, PA, latest edition, which is incorporated herein by reference. Such methods include conventional mixing, dissolving, granulating, dragee-making, levigating, emulsifying, encapsulating, entrapping or lyophilizing. Pharmaceutical compositions may be formulated in conventional manner using one or more physiologically acceptable carriers, diluents, excipients or auxiliaries which facilitate processing of the receptor ligand into a pharmaceutical composition. Exact details of a specific composition are dependent, inter alia, upon a desired route of administration.

For topical administration, a receptor ligand according to the teachings herein may be formulated in a solution, gel, ointment, cream, suspension, foam and the like.

Systemic administration may be achieved by a composition configured for injection, e.g., subcutaneous, intravenous, intramuscular, intrathecal or intraperitoneal injection, as well as for transdermal, transmucosal, inhalation, oral or pulmonary administration.

For injection, a receptor ligand according to the teachings herein may be formulated in aqueous solutions, preferably in physiologically compatible buffers such as Hank's solution, Ringer's solution, or physiological saline buffer.

For oral administration, a composition comprising a receptor ligand according to the teachings herein may be formulated by combining with pharmaceutically-acceptable carriers for oral administration as known in the art, for example, to form tablets, pills, dragees, capsules, liquids, gels, syrups, slurries, suspensions and the like, for oral ingestion. Solid oral compositions typically include such as fillers such as sugars, e. g. lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. Liquid oral compositions such as suspensions, elixirs and solutions, typically include water, glycols, oils, alcohols, suspension agents, flavoring agents and preservatives.

A pharmaceutical composition may be configured as a suppository for rectal or vaginal administration and comprises conventional suppository bases such as cocoa butter and/or other glycerides.

Use of (Synthetic) Somatostatin Receptor Ligand

According to an aspect of some embodiments of the teachings herein, there is also provided a use of a (synthetic) Somatostatin receptor ligand according to one or more of the aspects of the teachings herein for the treatment of a living organism, comprising, administering a pharmaceutically effective amount of the receptor ligand to the organism.

Typically, the Somatostatin receptor ligand is administered to the organism by administering a pharmaceutical composition including the Somatostatin receptor ligand.

In some embodiments, the use is for targeting a cell expressing one or more Somatostatin receptor with an active agent moiety of the (synthetic) Somatostatin receptor ligand, in some embodiments for targeting a cell overexpressing one or more Somatostatin receptor.

In some embodiments, the use is for identifying a cell expressing one or more Somatostatin receptor, in some embodiments for identifying a cell overexpressing one or more Somatostatin receptor.

In some embodiments, the cell overexpressing one or more Somatostatin receptor is a pathological cell, in some embodiments a cancer cell.

Method of Treatment

According to an aspect of some embodiments of the teachings herein, there is also provided a method of treating a cell expressing one or more Somatostatin Receptor comprising: administering at least one (synthetic) Somatostatin receptor ligand according to one or more of the aspects of the teachings herein to a cell expressing (and in some embodiments, overexpressing) one or more Somatostatin Receptor, thereby treating the cell. In some embodiments, the method is for implementing a use as described above.

In some embodiments, the administering at least one Somatostatin receptor ligand is administering at least two different Somatostatin receptor ligands. In some such embodiments, at least two of the different Somatostatin receptor ligands are administered serially. In some such embodiments, at least two of the different Somatostatin receptor ligands are administered concurrently. In some such embodiments, at least two of the different Somatostatin receptor ligands are administered simultaneously.

In some embodiments, the cell and the administering are in vitro. In some such embodiments, the cell is alive.

In some embodiments, the cell is in vivo and the administering is to a living organism. In some such embodiments, the living organism is a non-human animal. In some such embodiments, the living organism is a human. Typically, the Somatostatin receptor ligand is administered to the organism by administering a pharmaceutical composition including the Somatostatin receptor ligand.

In some embodiments, the method further comprises: subsequently to the administering, applying an imaging modality to the cell to identify an interaction of the Somatostatin receptor ligand with the cell. Typically such embodiments include the administration of at least one peptide moiety—active agent moiety conjugate, especially a peptide moiety—imaging agent moiety conjugate. Some such embodiments are applied, for example, for diagnosis (e.g., presence or absence of pathological cells overexpressing one or more Somatostatin receptors) and/or intrasurgical pathology (cancer) visualization. Any suitable imaging modality may be used to implement such an embodiment, for example, microscope, fluorescence detector, radiation detector, light detector, NMR, X-Ray, CT, and Positron Emission Tomography.

In some embodiments, the method further comprises, subsequently to the administering, manipulating a cell as a result of interaction of the Somatostatin receptor ligand with the cell. Depending on the embodiment, such manipulating includes manipulations such as irradiation with light, heat, sound, ultrasound, shock wave, X-rays, radiation or physical contact (e.g., for excision).

Exemplary Peptide—Fluorescent Agent Conjugates

In Table 1 are listed the sequences of sixteen compounds 1-16. All sixteen compounds 1-16 are peptide-fluorescent agent conjugates, having a peptide part that includes a cyclic peptide moiety cyclized through a sulfur-sulfur bond, and a fluorescent active agent moiety (FITC-GABA), that includes fluorescein isothiocyanate fluorophore and a GABA linker, where the fluorescent active agent moiety is covalently bonded to the cyclic peptide moiety through the nitrogen atom of the N-terminal amine. In compounds 1-16, A is Xxx9 a GlyS2 moiety. As detailed in the experimental section, all sixteen compounds were synthesized and found to be Somatostatin receptor ligands that have a relatively high affinity to one or more Somatostatin receptor.

Compound 1 is identical to a known synthetic Somatostatin receptor ligand described in U.S. Pat. No. 7,700,717 designated 86, and when devoid of the fluorescent active agent moiety is designated 3207. Compounds 2-16 are novel compounds having novel amino acid residue sequence that are suitable for use in implementing the first aspect of the teachings herein.

Compounds 1-12, 14-16 are suitable for use in implementing the teachings of the second and third aspects of the teachings herein. Additionally, two compounds described in U.S. Pat. No. 7,700,717 and mentioned hereinabove are also considered exceptionally useful in implementing the second and third aspects of the teachings herein, specifically, Compound 30 (GlyS2*-Phe-Trp-DTrp-Lys-Thr-Phe-GlyS2*-NH$_2$, designated 3213) and Compound 31 (DPhe-GlyS2*-Phe-Trp-DTrp-Lys-Thr-Phe-GlyS2*-NH$_2$, designated 3173). Additionally, Lanreotide and Octreotide are also considered as being exceptionally useful for implementing the second and third aspects of the teachings herein.

ligand according to the teachings herein and was internalized selectively by cells overexpressing Somatostatin Receptors.

Bonding of Compounds 1-16 to SSTRx

As detailed in the experimental section below, the relative binding affinity of compounds 1-16 to cells expressing only a single type of SSTRx was studied. The found relative binding affinities of compounds 1-16 is detailed in Table 2.

TABLE 1 sequence of synthesized chemical compounds

|    |              | Xxx1  | Xxx2 | Xxx3 | Xxx4 | Xxx5 | Xxx6  | Xxx7    | Xxx8 | A = Xxx9-A' | SEQ ID |
|----|--------------|-------|------|------|------|------|-------|---------|------|-------------|--------|
| 1  | FITC-GABA-   | D-Phe |      | Cys  |      | Phe  | Trp   | D-Trp   | Lys  | Thr  | Phe | GlyS2 | 6  |
| 2  | FITC-GABA-   | D-Phe | Arg  | Cys  |      | Phe  |       | D-Trp   | Lys  | Thr  | Phe | GlyS2 | 12 |
| 3  | FITC-GABA-   | D-Phe |      | Cys  |      | Phe  | Trp   | D-Trp   | Orn  | Thr  | Phe | GlyS2 | 17 |
| 4  | FITC-GABA-   | D-Phe |      | Cys  |      | Tyr  | Trp   | D-Trp   | Lys  | Thr  | Phe | GlyS2 | 21 |
| 5  | FITC-GABA-   | D-Phe | Arg  | Cys  |      | Phe  |       | D-Trp   | Orn  | Thr  | Phe | GlyS2 | 25 |
| 6  | FITC-GABA-   | D-Phe | Arg  | Cys  |      | Tyr  |       | D-Trp   | Lys  | Thr  | Phe | GlyS2 | 30 |
| 7  | FITC-GABA-   | D-Phe |      | Cys  |      | Tyr  |       | D-Trp   | Orn  | Thr  | Phe | GlyS2 | 35 |
| 8  | FITC-GABA-   | D-Phe |      | Cys  | Arg  | Phe  | Phe   | D-Trp   | Lys  | Thr  | Phe | GlyS2 | 39 |
| 9  | FITC-GABA-   |       |      | Cys  | Arg  | Phe  |       | D-Trp   | Lys  | Thr  | Phe | GlyS2 | 45 |
| 10 | FITC-GABA-   | D-Phe |      | Cys  | Arg  | Phe  |       | D-Trp   | Lys  | Thr  | Phe | GlyS2 | 46 |
| 11 | FITC-GABA-   | D-Phe |      | H-Cys |     | Phe  | Trp   | D-Trp   | Lys  | Thr  | Phe | GlyS2 | 50 |
| 12 | FITC-GABA-   | D-Phe |      | D-Cys |     | Phe  | Trp   | D-Trp   | Lys  | Thr  | Phe | GlyS2 | 52 |
| 13 | FITC-GABA-   | D-Phe |      | Cys  |      | Phe  | Trp   | D-Trp   | Aib  | Thr  | Phe | GlyS2 | 54 |
| 14 | FITC-GABA-   | D-Phe |      | Cys  |      | Phe  | Trp   | D-Trp   | LysAc | Thr | Phe | GlyS2 | 58 |
| 15 | FITC-GABA-   | D-Phe |      | Cys  |      | Phe  | Trp   | D-Trp   | Arg  | Thr  | Phe | GlyS2 | 62 |
| 16 | FITC-GABA-   | D-Phe |      | Cys  |      | Phe  | Trp   | D-Trp   | Homo-Lys | Thr | Phe | GlyS2 | 64 |

Somatostatin Receptor Ligands Bonded to Nanoparticles

As detailed in the experimental section below, a number of the Compounds 1-12, 14-16 were conjugated with nanoparticles by covalent binding with the nitrogen atom of an internal amino acid side chain to yield Somatostatin receptor ligands according to the second aspect of teachings herein. As noted previously, despite the expectation that such conjugation would block the Somatostatin receptor-binding pharmacophore of the respective molecule, it was surprisingly found that in vivo, the peptide conjugated with FITC and the nanoparticle remained a Somatostatin receptor An "x" indicates that a given binding affinity was not determined. A "0" indicates that no binding was detected.

A conclusion that can be made from the results found in Table 2 is that all fifteen novel compounds 2-16 are ligands for at least one SSTRx with a binding affinity of the same order of magnitude as compound 1. Therefore, in at least one embodiment, the compounds according to the teachings herein are useful for binding to cells expressing, especially overexpressing, one or more SSTRx. As detailed above, and in the example below, such binding has utility in many fields, for example in the field of pathology.

TABLE 2

Relative binding affinity of compounds 1-16

| compound | SSTR1 | SSTR2 | SSTR3 | SSTR4 | SSTR5 |
|---|---|---|---|---|---|
| 1 | 3 | 6.5 | 17 | 22.5 | 28.5 |
| 2 | 5 | 5 | 4 | 4 | 5 |
| 3 | 3.6 | 4.3 | 15.7 | 13.3 | 9.3 |
| 4 | 3.6 | 4.3 | 15.7 | 13.3 | 9.3 |
| 5 | 0 | 1 | 3 | 1 | 0 |
| 6 | 0 | 1.5 | 22.5 | 1.5 | 0.5 |
| 7 | 0 | 1 | 2 | 1.5 | 1 |
| 8 | 2.6 | 4.5 | 11.5 | 31.5 | 27.5 |
| 9 | 0 | 10 | 14 | 15 | 20 |
| 10 | 5 | 5 | 4 | 4 | 5 |
| 11 | x | x | x | 29 | 41 |
| 12 | x | x | x | x | x |
| 13 | 1 | 0 | 6 | 4 | 9 |
| 14 | x | x | x | 3 | 2 |
| 15 | 4 | 5 | 13.5 | 9 | 7.5 |
| 16 | 0 | 2.5 | 12 | 4.5 | 7 |

Relative Binding Affinity of Compounds 1-16 to Different SSTRx

Comparison within a row of Table 2 shows the relative binding affinity of a given compound 1-16 to each one of the five SSTRx as an indication as to how selectively that compound binds to the different SSTRx. The results of Table 2 with each row normalized according to the highest binding affinity, are shown in Table 2-A.

TABLE 2-A

Adjusted binding affinity of compounds 1-16 to SSTRx

| compound | SSTR1 | SSTR2 | SSTR3 | SSTR4 | SSTR5 |
|---|---|---|---|---|---|
| 1 | 0.11 | 0.23 | 0.60 | 0.79 | 1 |
| 2 | 1 | 1 | 0.80 | 0.80 | 1 |
| 3 | 0.23 | 0.27 | 1 | 0.85 | 0.59 |
| 4 | 0.13 | 0.33 | 1 | 0.33 | 0.40 |
| 5 | 0 | 0.33 | 1 | 0.33 | 0 |
| 6 | 0 | 0.07 | 1 | 0.07 | 0.02 |
| 7 | 0 | 0.50 | 1 | 0.75 | 0.50 |
| 8 | 0.08 | 0.14 | 0.37 | 1 | 0.87 |
| 9 | 0 | 0.50 | 0.70 | 0.75 | 1 |
| 10 | 1 | 1 | 0.80 | 0.80 | 1 |
| 11 | x | x | x | 0.71 | 1 |
| 12 | x | x | x | x | x |
| 13 | 0.11 | 0 | 0.67 | 0.44 | 1 |
| 14 | x | x | x | 1 | 0.67 |
| 15 | 0.30 | 0.37 | 1 | 0.67 | 0.56 |
| 16 | 0 | 0.21 | 1 | 0.38 | 0.58 |

A conclusion that can be made from study of Table 2-A is that each one of compounds 1-16 has a unique set of relative affinities to the five different SSTRx. In some embodiments, such different relative affinities allows the teachings herein to be used to target cells expressing any SSTRx by selecting a suitable compound according to the teachings herein. As detailed above, and in the example below, such binding has utility in many fields, for example in the field of pathology.

For example, the results indicate that Compound 2 (SEQ ID NO:12) and Compound 10 (SEQ ID NO:46) have little binding specificity and bind to all five SSTRx with roughly the same affinity. Accordingly, in some embodiments a compound according to the teachings herein that comprises the amino acid residue sequence of any one of Compounds 2 and 10 are used to bind to any cells overexpressing one or more SSTRx.

The results indicate that Compound 7 (SEQ ID NO:35) and Compound 9 (SEQ ID NO:45) bind to SSTR2, SSTR3, SSTR4 and SSTR5, but not to SSTR1. Accordingly, in some embodiments a compound according to the teachings herein that comprises the amino acid residue sequence of any one of Compounds 7 and 9 are used to differentiate between cells overexpressing any of SSTR2-SSTR5, and cells overexpressing SSTR1.

The results indicate that Compound 6 (SEQ ID NO:30) is very specific and preferentially binds to SSTR3 while Compound 4 (SEQ ID NO:21) and Compound 5 (SEQ ID NO:25) are relatively specific and preferentially bind to SSTR3. Accordingly, in some embodiments a compound according to the teachings herein that comprises the amino acid residue sequence of any one of Compounds 4, 5 and 6 are used to identify cells overexpressing SSTR3.

Other compounds preferentially bind to two SSTRx with similar affinities and not to the other three SSTRx, specifically: Compound 8 (SEQ ID NO:39) to SSTR4 and SSTR5 and not SSTR1, SSTR2 and SSTR3, and Compound 13 (SEQ ID NO:54) and Compound 16 (SEQ ID NO:64) to SSTR3 and SSTR5 and not SSTR1, SSTR2 and SSTR4. Accordingly, in some embodiments a compound according to the teachings herein that comprises the amino acid residue sequence of any one of Compounds 8, 13 and 16 are used to differentiate between cells overexpressing some SSTRx and not other SSTRx.

Other compounds preferentially bind to three SSTRx with similar affinities and not to the other two SSTRx, specifically: Compound 1 (SEQ ID NO:6), Compound 3 (SEQ ID NO:17) and Compound 15 (SEQ ID NO:62) all preferentially bind to SSTR3, SSTR4 and SSTR5 and not to SSTR1 and SSTR2. Accordingly, in some embodiments a compound according to the teachings herein that comprises the amino acid residue sequence of any one of Compounds 1, 3 and 15 are used to differentiate between cells overexpressing some SSTRx and not other SSTRx.

Comparison within a row of Table 2, shows the relative binding affinity of a given compound 1-16 to each one of the five SSTRx as an indication as to how selectively that compound binds to the different SSTRx.

Relative binding affinity of the compounds 1-16 to the same SSTRx

Comparison within a column of Table 2 shows the relative binding affinity of a given compound 1-16 to a specific SSTRx relative to the other compounds 1-16, as an indication as to which chemical compound binds most effectively to which SSTRx. The results of Table 2 with each column normalized according to the binding affinity of prior art compound 1, are shown in Table 2-B.

TABLE 2-B

Binding affinity of Compounds 2-16 to SSTRx relative to Compound 1

| Compound | SSTR1 | SSTR2 | SSTR3 | SSTR4 | SSTR5 |
|---|---|---|---|---|---|
| 1 | 100 | 100 | 100 | 100 | 100 |
| 2 | 167 | 77 | 24 | 18 | 18 |
| 3 | 120 | 66 | 92 | 59 | 33 |
| 4 | 100 | 123 | 141 | 36 | 4 |
| 5 | 0 | 15 | 18 | 4 | 0 |
| 6 | 0 | 23 | 132 | 7 | 2 |
| 7 | 0 | 15 | 12 | 7 | 4 |
| 8 | 78 | 69 | 68 | 140 | 96 |
| 9 | 0 | 154 | 82 | 67 | 70 |
| 10 | 167 | 77 | 24 | 18 | 18 |
| 11 | x | x | x | 129 | 144 |
| 12 | x | x | x | x | x |
| 13 | 33 | 0 | 35 | 18 | 32 |
| 14 | x | x | x | 13 | 7 |
| 15 | 133 | 77 | 79 | 40 | 26 |
| 16 | 0 | 38 | 71 | 20 | 25 |

A conclusion that can be made from study of Table 2-B is that for each one of the five SSTRx, at least one compound 2-16 has a greater binding affinity than does prior art Compound 1.

Specifically, for SSTR1, Compounds 2, 3, 10 and 15 have a greater binding affinity than Compound 1.

For SSTR2, Compounds 4 and 9 have a greater binding affinity than Compound 1.

For SSTR3, Compounds 4 and 6 have a greater binding affinity than Compound 1.

For SSTR4, Compounds 8 and 11 have a greater binding affinity than Compound 1.

For SSTR5, Compound 11 have a greater binding affinity than Compound 1.

Use of Peptide-Active Agent Conjugates in Pathology

In the art of pathology it is known to determine the nature of a cell or tissue. For example, a biopsy of suspect tissue is retrieved and the pathologist attempts to determine whether or not the tissue is pathological.

Some compounds according to the teachings herein are peptide-active agent conjugates, comprising a SSTRx binding moiety comprising an amino acid residue sequence according to the teachings herein conjugated with an indicator active agent moiety. One or more peptide—active agent conjugate are administered to a cell. The conjugate or conjugates bind to SSTRx expressed by the cells with relation to the relative affinities of the administered binding moiety to the different SSTRx and the relative abundance of each SSTRx expressed by the cell.

Subsequently, the presence and relative abundance of the indicator active agent moiety or moieties is determined in the usual way (e.g., direct observation for dyes, observation under suitable conditions for fluorescent active agents, radiation detectors for radioactive active agents) allowing elucidation of which, if any, SSTRx are expressed (overexpressed) by the cell, and in some embodiments, the relative distribution thereof.

In some embodiments, compounds 1-16 are used to implement such embodiments.

Single Peptide-Active Agent Conjugate in Pathology

A biopsy sample of tissue recovered from a person is provided to a pathologist to identify whether or not the tissue is pathological tissue that overexpresses SSTRx.

The pathologist administers a dose of a composition comprising a peptide—indicator conjugate according to the teachings herein comprising the amino acid residue sequence of Compound 2 (e.g., Compound 2) in a buffer solution to the biopsy sample in the usual way, allows the biopsy sample to incubate in the presence of the conjugate and then removes excess liquids. Examination of the biopsy sample under suitable conditions that detect the presence of the indicator moiety on or in a cell, allows the pathologist to determine whether or not the biopsy sample is stained by the conjugate, providing evidence to help the pathologist conclude whether or not the biopsy sample or parts thereof include cells that overexpress SSTRx. In some embodiments when the active agent of the administered conjugate is fluorescent (e.g., Compound 2), examination is under a suitable microscope (e.g., Leica® TCS SP8 STED 3× microscope equipped with a Leica® DFC550 digital camera) with illumination conditions that allow the fluorophore of the conjugate (e.g., FITC in compound 2 to fluoresce and allow the pathologist to conclude what parts, if any, of the biopsy sample include cells that overexpress SSTRx.

Multiple Peptide-Active Agent Conjugate in Pathology

In some embodiments, at least two different peptide—indicator conjugates are provided, each having a peptide moiety having a different amino acid residue sequence according to the teachings herein, and a different indicator moiety. Typically but not necessarily, the indicator moieties are of the same type, e.g., are all dyes or are all fluorescent.

A combination of two or more different peptide—indicator conjugates are co-administered to a cell. The conjugates bind to SSTRx expressed by the cell with relation to the relative affinities of the administered binding moiety to the different SSTRx and the relative abundance of each SSTRx expressed by the cell.

Subsequently, the presence and relative abundance of the two or more indicator active agent moieties is determined in the usual way allowing elucidation of which, if any, SSTRx are expressed (overexpressed) by the cell, and in some embodiments, the relative distribution thereof.

In some embodiments, at least one of compounds 1-16 are used to implement such embodiments, together with at least one other compound according to the teachings herein. In some embodiments, at least one other compound is a derivative of a compound 1-16 having a different fluorophore. A person having ordinary skill in the art of synthetic chemistry is able to synthesize such derivatives without undue experimentation upon perusal of the specification, for example using syntheses based on the disclosed herein.

In some such embodiments, two different peptide—indicator conjugates are administered serially, that is to say, first one conjugate is administered, after an incubation time some of the first one is removed from contact with the cell (e.g., washed away), and then a second conjugate is administered.

In some such embodiments, two different peptide—indicator conjugates are administered concurrently, that is to say, first one conjugate is administered, followed by administration of a second conjugate.

In some such embodiments, two different peptide—indicator conjugates are administered substantially simultaneously.

For example, in one such embodiment, it is desired to determine the relative abundance of the SSTRx expressed by cells making up a biopsy sample of tissue recovered from a person provided to a pathologist.

A first peptide—indicator conjugate compound 5' (that binds to SSTR4 and not SSTR5) is synthesized that is similar to compound 5 but instead of conjugation with a FITC fluorophore, is conjugated with a Pacific Blue fluorophore that is excited with 403 nm light to fluoresces at 455 nm (blue).

A second peptide—indicator conjugate compound 6' (that binds almost exclusively to SSTR3) is synthesized that is similar to compound 6 but instead of conjugation with a FITC fluorophore, is conjugated with a TRITC (tetramethylrhodamine) fluorophore that is excited with 547 nm light to fluoresces at 572 nm (orange).

A third peptide—indicator conjugate compound 8' (that binds preferentially to SSTR4 and SSTR5) is synthesized that is similar to compound 8 but instead of conjugation with a FITC fluorophore, is conjugated with a BODIPY-TR (boron-dipyrromethene) fluorophore that is excited with 588 nm light to fluoresces at 616 nm (red).

A fourth peptide—indicator conjugate, compound 10, (that binds to substantially all SSTRx), above, is synthesized that is conjugated with a FITC fluorophore that is excited with 492 nm light to fluoresces at 520 nm (green).

A fifth peptide indicator conjugate, compound 13' (that binds to SSTR1 but not SSTR2) is synthesized that is similar to compound 13 but instead of conjugation with a FITC fluorophore, is conjugated with a methoxycoumarin fluorophore that is excited with 360 nm light to fluoresces at 410 nm (blue).

With the help of a fluorometer, a pharmacist prepares a composition comprising the five compounds 5', 6', 8', 10 and 13' in a buffer solution in relative concentrations that provide emissions with near-identical intensity.

The pathologist administers a dose of the composition with the five compounds, allows the biopsy sample to incubate in the presence of the composition and then removes excess liquids. The tissue is examined under a microscope with illumination conditions that allow the respective fluorophores of the administered compounds to fluoresce allows the pathologist to determine whether or not the biopsy sample is stained by which conjugate, providing evidence to help the pathologist conclude whether or not the biopsy sample or parts thereof include cells that overexpress each specific SSTRx, in some embodiments and if necessary, using basic algebra to solve a set of five equations with five unknowns.

EXPERIMENTAL

Materials

GlyS2 was synthesized according to the methods described in Gazal (Gazal S et al J Pept Res 2001, 58(6), 527-539).

All other required chemical compounds and reagents were purchased from well-known commercial suppliers, inter alia, Sigma-Aldrich (St. Louis, MO, USA).

Animals

All in vivo experiments were performed on anesthetized animals and were conducted in compliance with the regulations of the Animal Welfare Committee of the Sheba Medical Center.

Synthesis of Compounds 1-16 (Table 1)

Compounds 1-16 were synthesized using standard solid-phase peptide synthesis (SPSS) methods such as described in U.S. Pat. No. 7,700,717 and Gazal with appropriate modification. Conjugation with the fluorescent active agent (FITC) was performed while the still-linear synthesized peptides were attached to the peptidyl resin for 4 hours using DIEA (N,N-diisopropylethylamine). Removal of protecting groups, cyclization and cleavage from the resin was performed as described in Falb (Falb, E., et al., *Bioorg Med Chem*, 2001, 9, 3255). Such cleavage resulted in all the compounds being amide-terminated (chemical entity A being GlyS2-NH$_2$ and chemical entity A' being NH$_2$.

Subsequent to cleavage, the resulting chemical compounds 1-16 were purified using preparative HPLC using a LiChrospher® 100 RP-18 (5 micrometer) Hibar® column 250 mm×25 mm and a water/acetonitrile (each containing 0.1% TFA) gradient.

Subsequent to purification, the purity and identity of chemical compounds 1-16 was confirmed using analytical HPLC, ESI-MS and, in some instances, HPLC-MS (LCQ). An HPLC-UltiMate® 3000 system (Dionex) was used equipped with 3000 pump, VWD-3000 UV-Vis detector and Chromeleon® 6.80 software. MS-LCQ Fleet™ LC-MS System, 3D Ion Trap, Thermo Scientific and Waters Xevo TQD were used for the determination of the molecular weight of the compounds and Gly-S2(Acm) building block. Theoretical molecular weight was calculated using ChemDraw Ultra 10.0, CambridgeSoft.

Binding Affinity of Compounds 1-16 to SSTRx (Table 2) In Vitro

The affinity of compounds 1-16 to each of the five SSTRx was tested using an in vitro model of transfected cell lines (HEK—human embryonic kidney), each expressing a single human SSTRx subtype. Biological activity assessment of the compounds to define a specific affinity to each subtype was performed by FACS and fluorescence imaging methods.

Human SSTRx were expressed in the cells by transient transfection. Each SSTR was expressed separately, creating five different cell lines using human gene transcript.

The transfection process is illustrated in FIG. 1. The transient transfection process was carried out before each experiment. Briefly, HEK cells were cultured in standard cell growth conditions. For testing, the cells were transferred into 96-well plates. The tested compounds were dissolved in DMSO and then diluted in a buffer solution to a final DMSO concentration of 5% as a composition according to the teachings herein. Various amounts of the thus-prepared compositions were added to the cells in medium in the 96-well plates and allowed to incubate for between 1 and 24 hours. Binding was determined using fluorescent microscopy and FACS.

Qualitative assessment of binding efficiency was done by visual inspection and digital photography using an inverted fluorescent microscope. Quantitative assessment was done using FACS.

HEK-293 cells (human embryonic kidney) were grown in Dulbecco's modified Eagle's medium (DMEM) supplemented with 4 mM glutamine, 10% fetal bovine serum (FBS) and 100 units/ml penicillin/streptomycin at 37° C./5% carbon dioxide. One day prior to transfection, the cells were trypsinized, counted and plated at a density of $3\times10^5$ per 35 mm diameter dish. Until 70% confluency, cells were transiently transfected with the pcDNA 3.1 vector bearing the coding region for the human SSTR human somatostatin receptor subtypes SSTR1-SSTR5. Transfections were carried out with JetPei transfection reagent (Polyplus-transfection, NY, USA) according to the manufacturer's recommendation. Briefly, 2 micrograms of plasmid DNA and 6 microliter of JetPei transfection reagent were used for each transfection. Each of the components were resuspended in 100 microliter of 150 mM NaCl, mixed and incubated for 25 minutes at room temperature and after incubation added to cells.

Cells were then seeded in a 96-well flat-bottom microplate (Costar, Corning, NY) at a concentration of $5\times10^4$ cells/well. Twelve hours later, the supernatant was removed and replaced with fresh DMEM containing various (in the nM range) concentrations of tested compounds 1-16. The cells were incubated for additional time intervals ranging from 0.5-24 hr. At the end of the incubation period, supernatant was discarded and the cells were washed twice with cold PBS. The plates were examined using IX81 inverted microscope (Olympus, Japan) equipped with PR71 digital camera. Additionally, a FACS assay was used for quantitative analysis.

Figure 2:
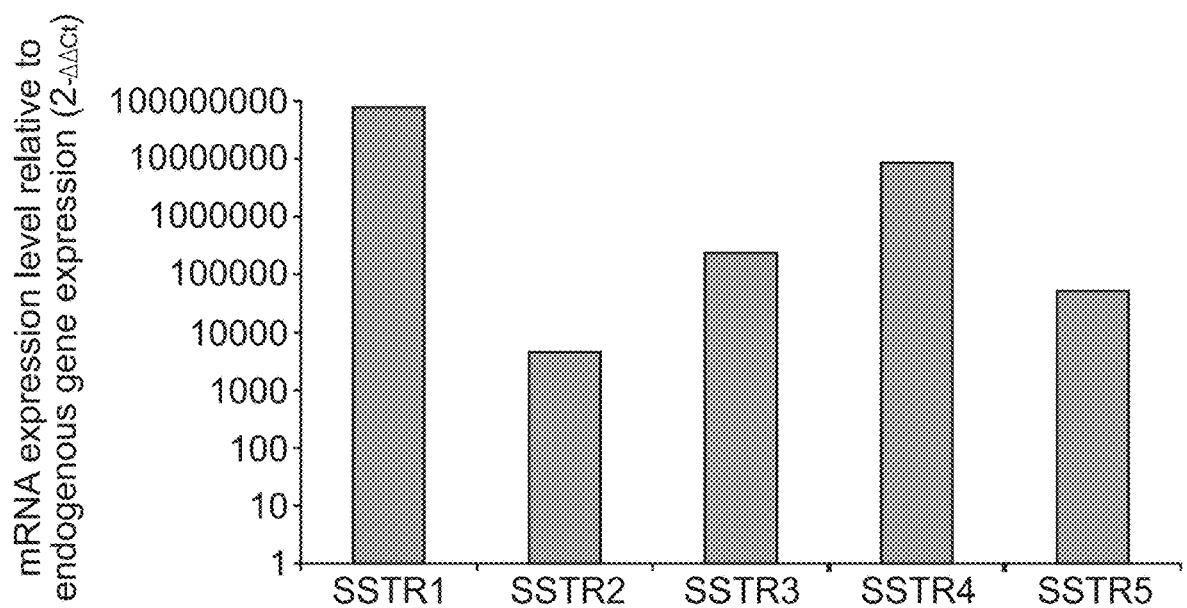
FIG. 2 is a bar graph showing SSTRx mRNA expression fold increase in transfected HEK-293 cells.
Figure 3:
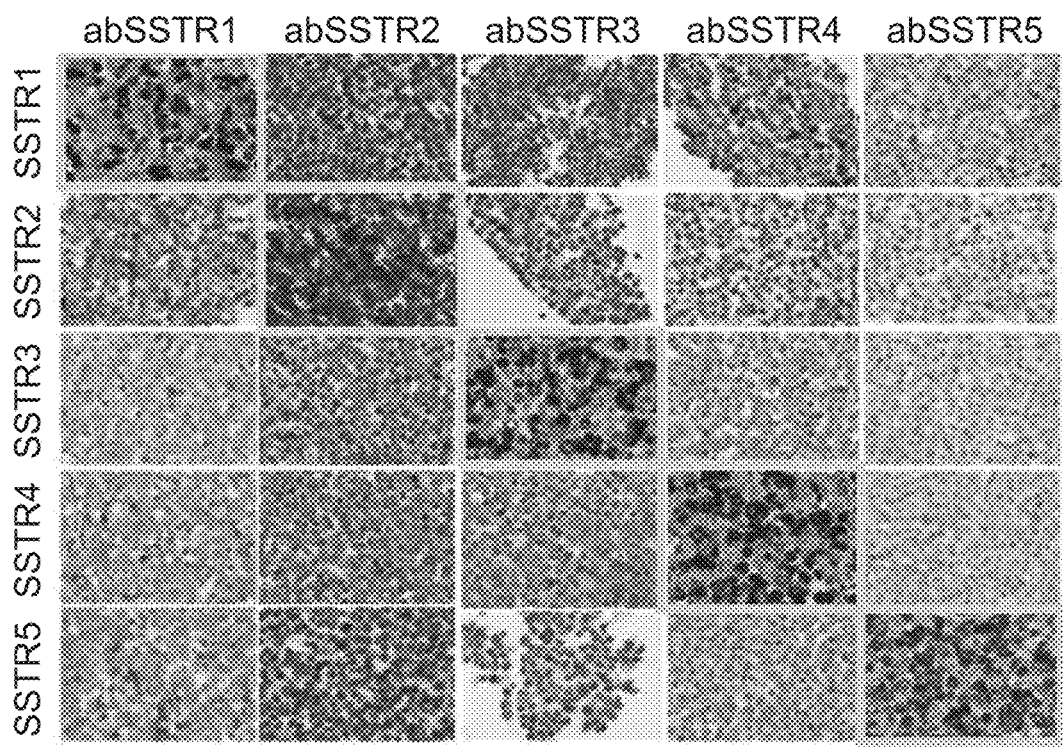
FIG. 3 shows reproductions of photographs validating of SSTRx expression in transfected cell blocks by specific antibodies.

Expression of the desired receptors was validated by RT-PCR (FIG. 2: SSTRx mRNA expression fold increase in transfected HEK-293) and IHC (FIG. 3: Validation of SSTRs expression in transfected cell blocks by specific antibodies), demonstrating efficient transfection and specific over-expression of all 5 human SSTRs.

Figures 4A, 4B, 4C:
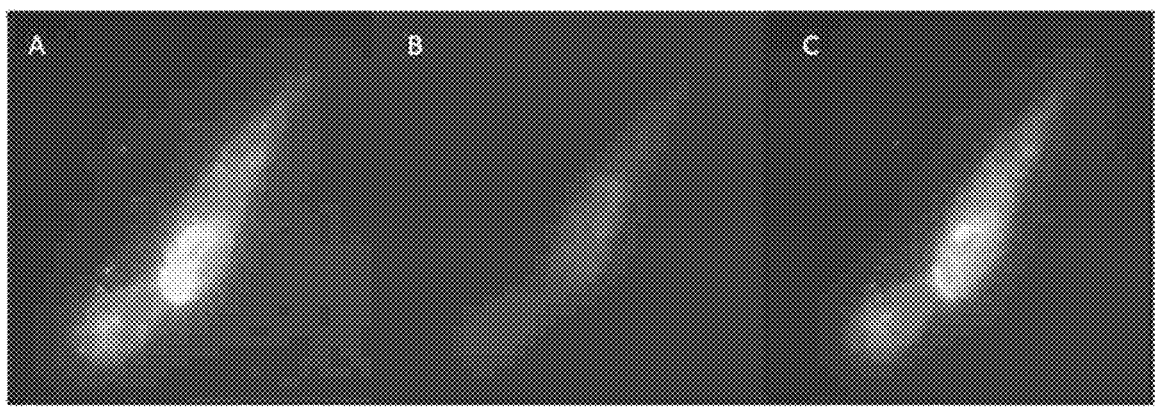
FIGS. 4A-4C shows reproductions of photographs illustrating internalization of Compound 1 into transfected HEK cells.

FIGS. 4A, 4B and 4C shows typical results of qualitative microscopic binding assay in HEK cells. Selective internalization of Compound 1 into transfected, SSTR5 over-expressing cells is clearly seen.

Figure 5A:
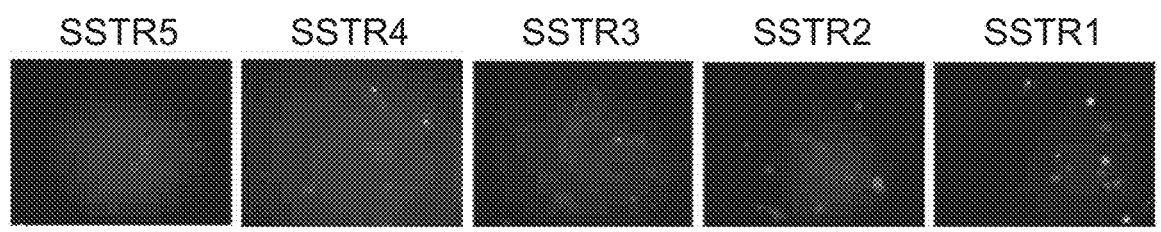
FIGS. 5A and 5B show reproductions of photographs indicating specific internalization of Compound 1 into SSTR1-SSTR5 transfected HEK cells.
Figure 5B:
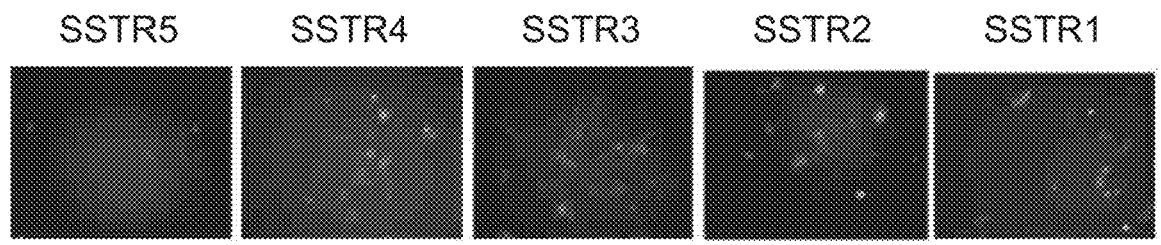

FIG. 5 shows comparative results of Compound 1 specific binding to all 5 transfected HEK cell lines, each expressing single SSTR.

Figure 6B:
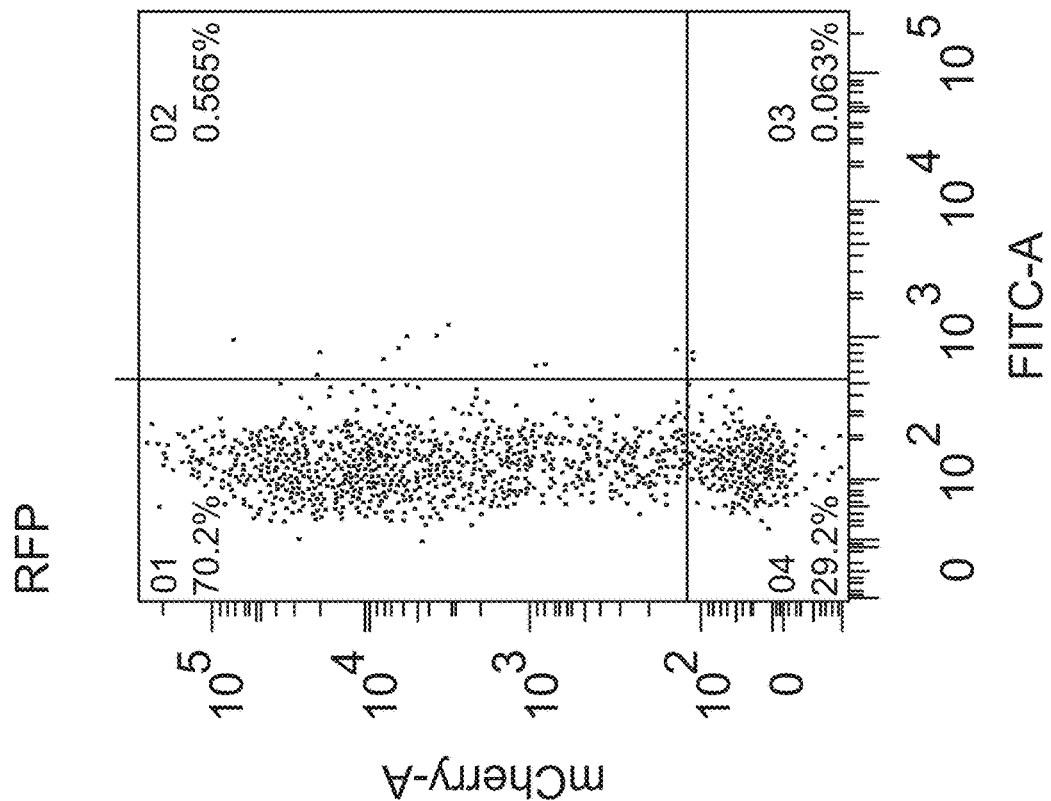
FIGS. 6A, 6B and 6C are graphs showing FACS results of Compound 1 in HEK cells.
Figure 6A:
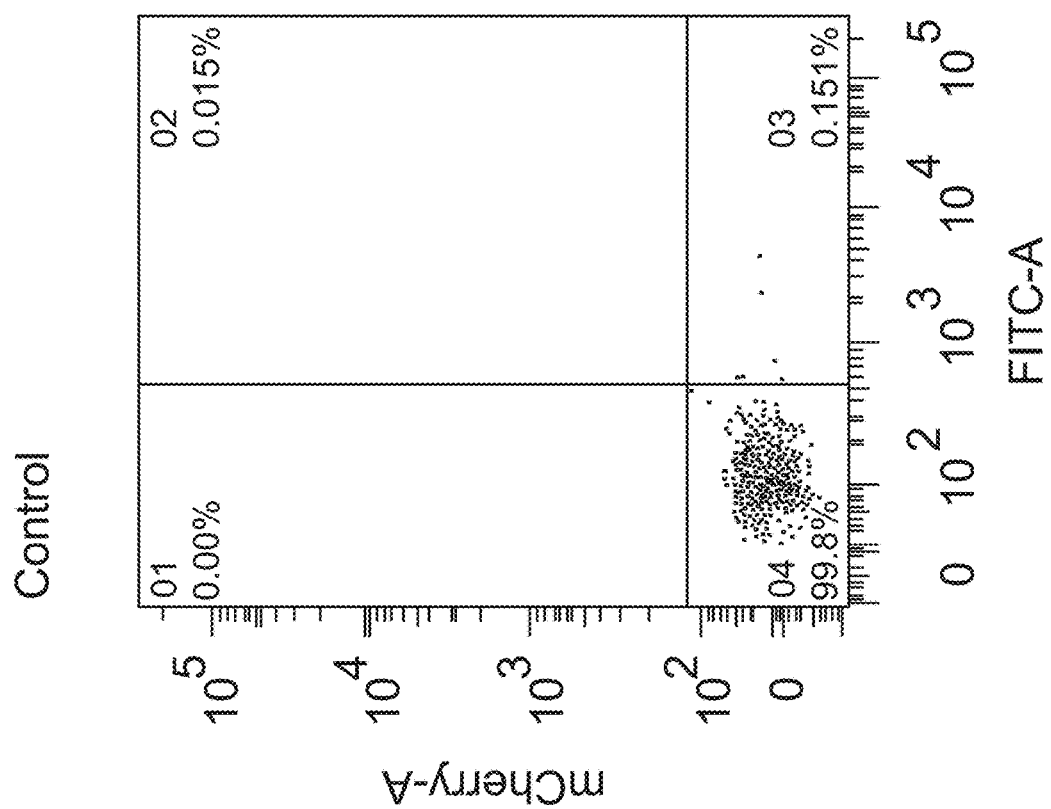
Figure 6C:
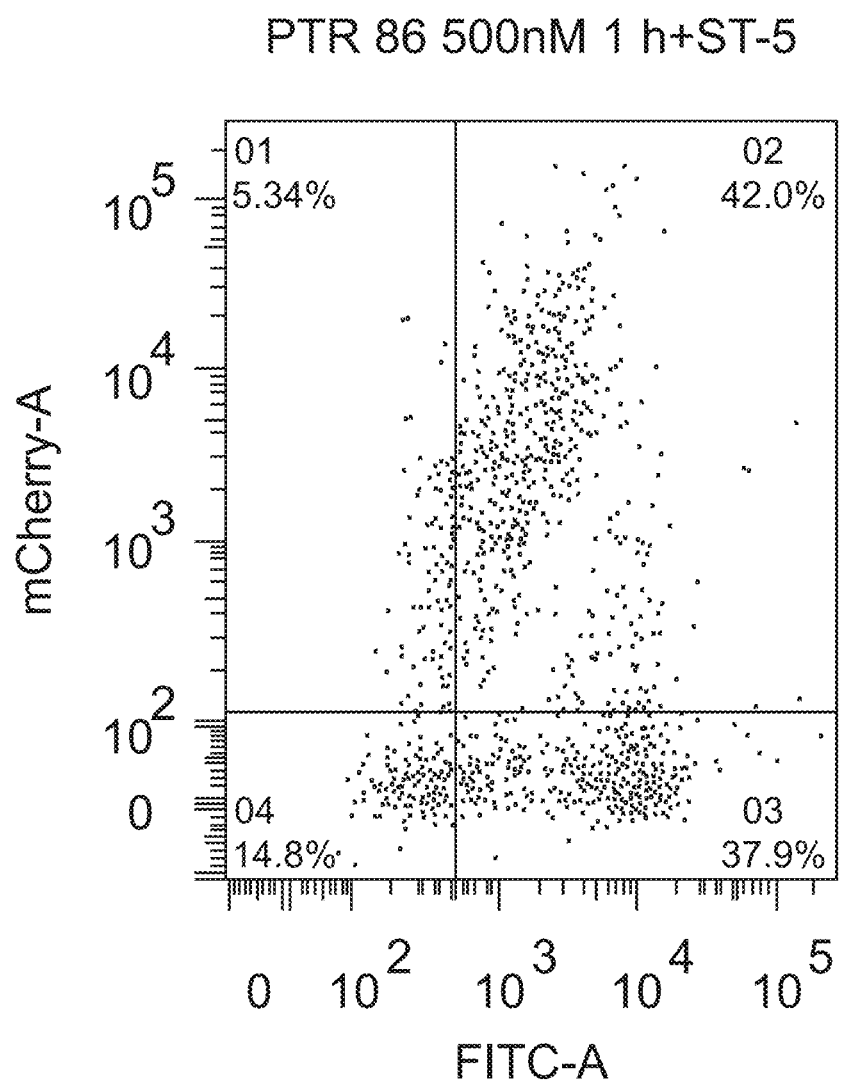

Quantitative assessment of binding affinity of Compounds 1-16 was performed by FACS in the transfected HEK cell model. Typical FACS results are shown in FIG. 6. Transition of fluorescence from the Green spectral region (lower left quarter) toward the double-stained Green-Red regions (GR) (upper right quarter) demonstrates specific binding of Compound 1 to SSTR-5 overexpressing transfected cells.

Quantitatively, specific binding affinity was assessed as the percentage of double stained [(GR=green and red indicating transfection)/(R is total red) less (G is green indicating unspecific binding)]:

specific binding affinity=$[GR/R-G]$

Control samples (PcDNA) showed generally >1% binding, thus, significant positive binding efficiency threshold was defined as >5%.

The results for all of the compounds binding to all of the SSTRx are presented and discussed in Tables 2, showing that all compounds have binding affinity and are therefor ligands for at least one SSTRx.

In Vivo

Pharmacokinetics and bio-distribution of some of the compounds was studied in mouse xenograft models for human cancer. Four pharmaceutical compositions according to the teachings herein, each comprising a single compound according to the teachings herein, were administered intravenously (IV) into lateral tail vein of nude mice bearing BON1 or H116 tumors. Animals were sacrificed at 1, 3, 6 and 24 hours after injection and tumor and normal tissues were excised. Tissue bio-distribution of the compounds were studied using fluorescence imaging techniques.

Solid human-derived tumors (BON-1 and HT116) were induced in nude mice by subcutaneous injection of a suspension containing ~5×$10^5$ cells into the flank area. Experiments were started 7-10 days after the injection, when the tumor diameter was approximately 5-10 mm.

Selected compounds (at a dose of 1 mg/ml, ~200 microliter/mouse, 10 mg/kg body weight) were administered intravenously to the lateral tail vein of tumor-bearing mice.

Whole-body fluorescence imaging, low-magnification fluorescence microscopy and cellular level fluorescence microscopy methods were used to study tissue biodistribution of the compounds. For these purposes, SZX-12 fluorescence microscope (Olympus, Japan), IX81 inverted fluorescence microscope (Olympus, Japan) equipped with appropriate filter-cubes and digital color camera (DP71, Olympus) were used. Additionally, whole-body fluorescence imaging was performed by WB imaging system (Prizmatix, Israel). Quantitative spectrally-resolved fluorescence imaging was carried out using a spectral imaging (SI) system (SD300, Applied Spectral Imaging, Migdal Ha'Emek, Israel).

The four compounds Compound 1 (86), Compound 2 (58), Compound 3 (Orn) and Compound 4 (Y) were chosen for assessment of in vivo bio-distribution and tumor targeting efficiency in 2 human tumor animal models. Fluorescence in tumor and normal tissues was studied by macro- and microscopic techniques at different time points after systemic administration of compositions including the compounds.

FIGS. 7 and 8 show the results of typical macroscopic evaluation of PTR bio-distribution in ex vivo tissue samples of tumor bearing mice 24 hrs after i.v. administration of the compounds. All 4 compounds clearly show selective accumulation in BON1 tumor, compared to normal tissues.

Figure 9:
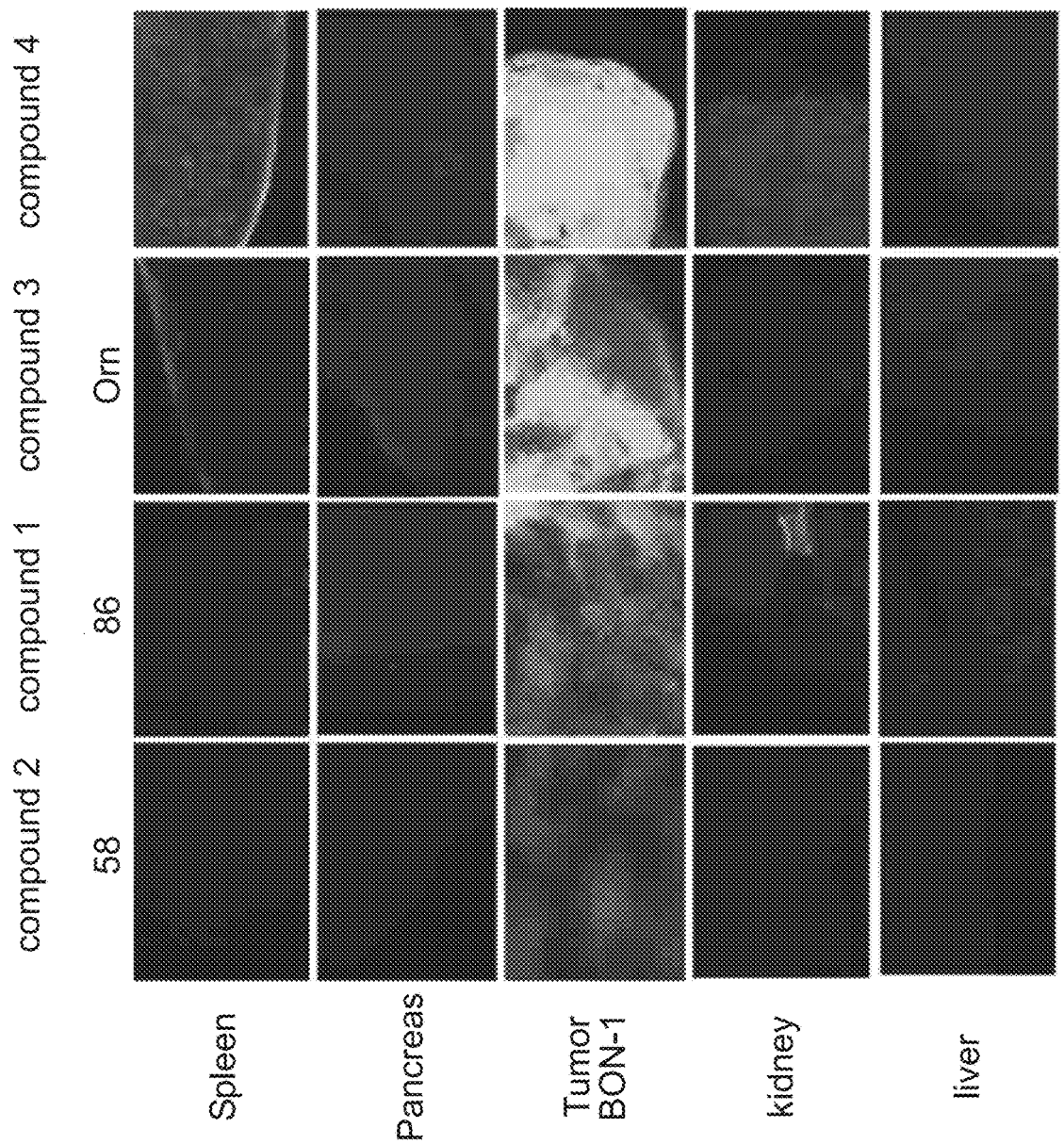
FIG. 9 shows a reproduction of photographs of the comparative bio-distribution assessment of compounds according to the teachings herein (10 mg/kg) 24 hr after IV administration, by microscopic fluorescence imaging (×40 magnification) (Left column Compound 2, followed by Compound 1, followed by Compound 3. Rightmost column Compound 4)

Comparative assessment of fluorescence intensity in tissue samples carried out by fluorescence microscopy revealed that all tested compounds had similar pattern of bio-distribution (FIG. 9). For example, 24 hrs after administration of Compound 4 (Y) maximal fluorescence was seen in tumor with decrease of fluorescence in the following order:

tumor>spleen>pancreas>kidney>liver

Figure 10:
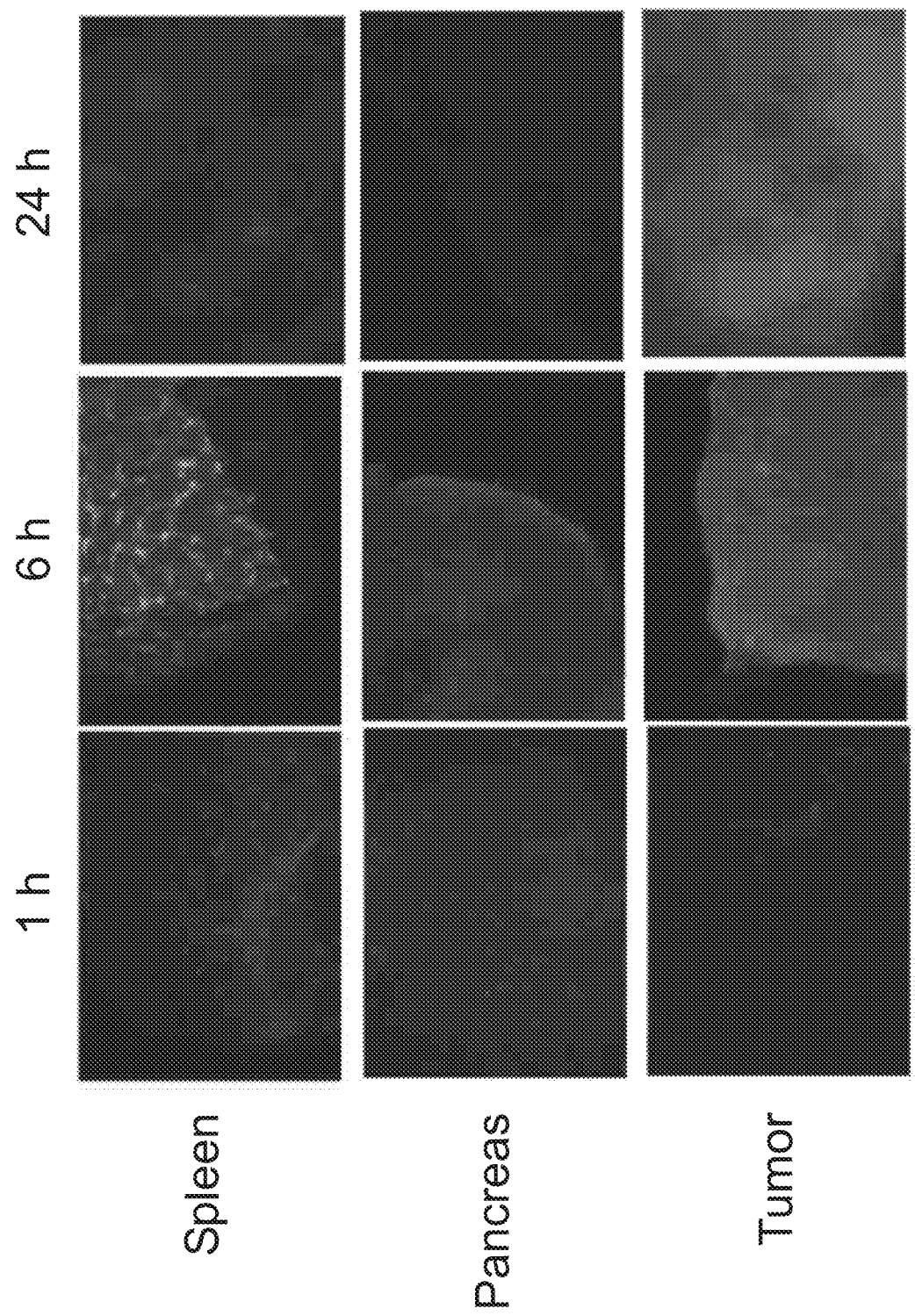
FIG. 10 shows a reproduction of photographs showing the time-dependent bio-distribution of Compound 3 (10 mg/kg) in spleen, pancreas and tumor after IV administration, by microscopic fluorescence imaging (×40 magnification)

FIG. 10 shows the bio-distribution pattern of Compound 3(Orn) as a function of time after administration by injection. Maximal fluorescence signal was detected in all tissues 6 hrs after agent administration. Then, in normal tissues fluorescence decreased significantly while in tumor the signal remained to be high, thus, resulting in 5-8 fold tumor-to-normal tissue ratio (TNR) at 24 hrs after injection. These results are in agreement with previous in vivo studies carried out using fiber optic spectroscopy.

Figure 11A:
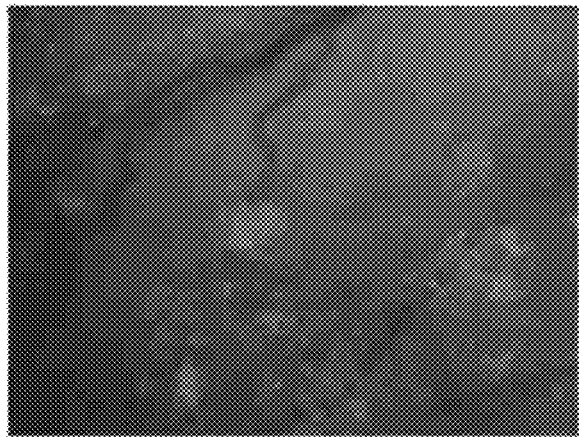
FIGS. 11A and 11B show the intra-cellular accumulation of Compound 3 (10 mg/kg) in BON1 tumor 1 hr after IV administration. Fluorescence microscopy (FIG. 11A: ×100, FIG. 11B: ×200 magnification)
Figure 11B:
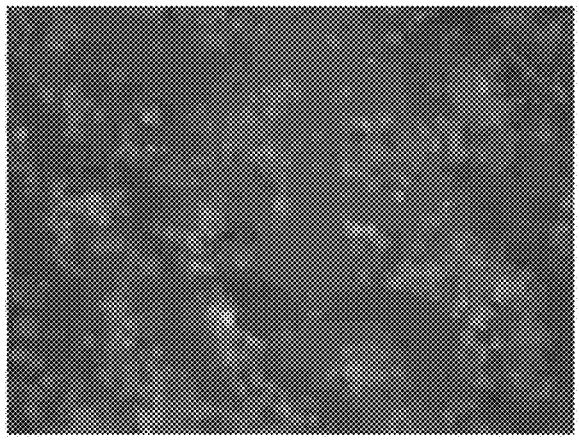
Figure 12A:
FIGS. 12A and 12B show the intra-cellular accumulation of Compound 3 (FIG. 12A) and Compound 2 (FIG. 12B) in an HT116 tumor 24 hr after IV administration. Fluorescence microscopy (×200 magnification)
Figure 12B:

Cellular level, high magnification microscopy revealed rapid internalization of compounds into tumor cells starting 1 hr after injection and lasted at least during 24 hrs (FIGS. 11 and 12).

In Vivo Administration of Pharmaceutical Compositions

Five different pharmaceutical compositions were prepared, each by dissolving 1 mg of a different Somatostatin receptor ligand in 1 liter PBS.

Solid human-derived tumors were induced in 15 nude mice by subcutaneous injection of a suspension containing ~5☐$10^5$ human cancer cells (PANC-1) into the flank area of the mice.

2-3 weeks after the injection of the cancer cells, it was observed that the mice developed solid tumors with diameters of approximately 5-10 mm.

0.3 ml of each one of the five pharmaceutical compositions were systemically administered to three of the fifteen xenograft mice by injection into the tail vein using a 30 G needle.

1 day after administration of the pharmaceutical compositions, none of the mice showed any unusual effect behavior, indicating that the administered compositions including Somatostatin receptor ligands were not toxic at the administered dose.

The fifteen mice were sacrificed and from the bodies tumors, pancreas, spleen, kidney and liver were harvested.

The fluorescence of the harvested tissue was determined using the Maestro™ in vivo fluorescence imaging system (Cambridge Research & Instrumentation, Inc., Woburn, MA, USA). The detected fluorescence was attributable to the fluorescence of the FITC moiety attached to the N-terminus of each Somatostatin receptor ligand that had been internalized by the cells of the tissue.

The results are presented in Table 3 where each one of columns a, b, c, d and e is the average of the results acquired from tissue of three mice to which the same composition was administered.

Col. a, total signal acquired from the tumors in units of counts/sec (average of three mice);
Col. b, ratio of signal from tumor divided by signal from pancreas (average of three mice); Col. c, ratio of signal from tumor divided by signal from spleen (average of three mice);
Col. d, ratio of signal from tumor divided by signal from kidney (average of three mice); and Col. e, ratio of signal from tumor divided by signal from liver (average of three mice).

Dashes ("-") indicate that the signal from the healthy tissue was below the lower limit of detection of the MAESTRO™ system.

TABLE 3 in vivo biodistribution of Somatostatin receptor ligands

| compound | code | a<br>Tumor<br>[count/s] | b<br>Tumor/<br>pancreas | c<br>Tumor/<br>spleen | d<br>Tumor/<br>kidney | e<br>Tumor/<br>liver |
|---|---|---|---|---|---|---|
| 1 | 86 | 130 | 150 | 298 | 38 | — |
| 2 | 58 | 80 | 80 | — | — | — |
| 3 | Orn | 80 | 29 | — | — | — |
| 9 | 21 | 290 | — | — | — | — |
| 4 | Y | 380 | 662 | 560 | 25 | 103 |

From the results in Table 3, it is seen that in all cases, tumor tissue fluoresced substantially more intensely than the healthy tissue, indicating that the Somatostatin receptor ligands were preferentially accumulated in tumor cells.

Compound 9 had the second highest absolute intensity in tumor tissue, but was undetectable in the healthy tissues.

Compound 4 had the highest absolute intensity in tumor tissue, which intensity was from 25× higher than in kidney tissue to 662× higher than in pancreas tissue.

Compound 1 had the third highest absolute intensity in tumor tissue, which intensity was undetectable in liver tissue, and from 38× higher than in kidney tissue to 298× higher than in spleen tissue.

Compounds 2 and 3 had the lowest absolute intensity in tumor tissue, which intensity was undetectable in spleen, kidney and liver tissue, and either 80× higher or 29× higher than in pancreas tissue, respectively.

The preceding experiment is repeated with different human cancer cell lines, e.g., BON-1 and HT116 with the same pharmaceutical compositions according to the teachings herein, and yield similar results.

The preceding experiment are repeated with different pharmaceutical compositions according to the teachings herein, inter alia pharmaceutical compositions comprising Somatostatin receptor ligands that include a cyclic peptide moiety based on any one of compounds 5-8 or 9-16, and yield substantially similar results.

Preparation of Somatostatin Receptor Ligands with Nanoparticles

Four Somatostatin receptor ligands according to the teachings herein where synthesized, each one of the four ligands including a residue of a Compound 1 with a cyclic peptide moiety defining a SSTRx binding pharmacophore and also having a fluorescent active agent (FITC-GABA-) covalently bonded to the N-terminus of the peptide moiety and one of four different nanoparticle active agents covalently bonded to the cyclic peptide moiety through the nitrogen atom of a functional group of an internal amino acid residue of the cyclic peptide moiety.

The four different nanoparticles were synthesized according to the procedure described in a scientific article describing the nanoparticle, see Table 4.

The synthesized nanoparticles were conjugated with Compound 1 to make a Somatostatin receptor ligand according to the teachings herein. Specifically, each nanoparticle was covalently bonded to Compound 1 through the nitrogen atom of the functional group of the internal amino acid residue Lys (designated Xxx6 in FIG. 13) using an appropriate chemistry, e.g., carbodiimide chemistry.

After purification in HPLC, the resulting four different Somatostatin receptor ligands were dissolved at a concentration of 1 mg in 1 milliliter of PBS solution to prepare four pharmaceutical compositions according to the teachings herein, the pharmaceutical compositions designated I-a, II-a, III-a and IV-a, see Table 4.

Four additional pharmaceutical compositions were prepared by dissolving each one of the four different nanoparticles at a concentration of 1 mg in 1 milliliter of PBS solution, the pharmaceutical compositions designated I-b, II-b, III-b and IV-b, see Table 4.

TABLE 4-A

Synthesized Somatostatin Receptor Ligands with nanoparticles

| composition | compound | code | nanoparticle |
|---|---|---|---|
| I-a<br>I-b | 1 | 86 | Human Serum Albumin based, described by:<br>Langer et al in Intl J Pharm 2008, 347(1-2), 109-117 |
| II-a<br>II-b | 1 | 86 | Can Maghernite based, described by:<br>Israel et al in ACS Appl Mater Interfaces 2015, 7(28), 15240-15255 |
| III-a<br>III-b | 1 | 86 | poly (N,N-DMAEMA) based, described by:<br>Plamper et al in Macromolecules 2007, 40(16), 5689-5697 |
| IV-a<br>IV-b | 1 | 86 | PLGA based, described by:<br>Sempf et al in Eur J Pharm Biopharm 2013, 85(1), 53-60 |

In Vivo Administration of Pharmaceutical Compositions Comprising Nanoparticles

Solid human-derived tumors were induced in eight nude mice by subcutaneous injection of a suspension containing $\sim 5 \times 10^5$ human cancer cells PANC-1 into the flank area. 2-3 weeks after the injection of the cancer cells, it was observed that the mice developed solid tumors with diameter approximately 5-10 mm.

0.3 ml of each one of the eight pharmaceutical compositions were systemically administered to one of the eight xenograft mice by injection into the tail vein using a 30 G needle.

24 hours after administration of the pharmaceutical compositions, none of the mice showed any unusual effect behavior, indicating that the administered pharmaceutical compositions were not toxic at the administered dose.

1 day after administration of the pharmaceutical compositions, none of the mice showed any unusual effect behavior, indicating that the administered Somatostatin receptor ligands were not toxic at the administered dose.

The mice were sacrificed. Tissue to be examined were excised and prepared for fluorescence microscopy examination in the usual way.

Fluorescence microscopy examination of the tissue of the four mice to which only nanoparticles were administered (compositions I-b, II-b, III-b and IV-b) showed minor background-intensity fluorescence in the kidney, liver, lung, spleen, pancreas and tumor.

Fluorescence microscopy examination of the tissue of the four mice to which compositions comprising Somatostatin receptor ligands (comprising a nanoparticle active agent) were administered (compositions I-a, II-a, III-a and IV-a) showed minor background-intensity fluorescence of the non-pathological tissue of the kidney, liver, lung, spleen and pancreas but substantially more intense fluorescence in the tumor, attributable to selective accumulation of the Somatostatin receptor ligand in the tumor tissue.

Although not wishing to be held to any one theory, the results indicate that the Somatostatin receptor ligands according to the teachings herein selectively recognized the Somatostatin receptors expressed by the tumor cells and that the receptor ligands were subsequently internalized together with the nanoparticle moiety.

Somatostatin receptor ligands according to the teachings herein selectively recognized the Somatostatin receptors expressed by the tumor cells and that the receptor ligands were subsequently internalized together with the nanoparticle moiety.

The preceding experiment are repeated with different pharmaceutical compositions according to the teachings herein, inter alia pharmaceutical compositions comprising Somatostatin receptor ligands that include a cyclic peptide moiety residue based on any one of compounds 5-8 or 9-16, and yield substantially similar results.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

We claim:

1. A somatostatin receptor ligand having the structure: DOTA-DPhe-Arg-Cys-Phe-DTrp-Lys-Thr-Phe-N($CH_2CH_2S$—)$CH_2CO$—$NH_2$ wherein a disulfide bond is formed between the N($CH_2CH_2S$—)$CH_2CO$ and the cysteine residue, and wherein DOTA is (1,4,7,10-tetraazacyclododecane-1,4,7,10-tetraacetic acid), and is either non-chelated or chelated to a metal atom or a radioactive atom, or a salt thereof.

2. The somatostatin receptor ligand, or a salt thereof, according to claim 1 wherein the metal atom is an MRI-detectable metal atom.

3. The somatostatin receptor ligand, or a salt thereof according to claim 2 wherein the MRI-detectable metal atom is iron or gadolinium.

4. The somatostatin receptor ligand, or a salt thereof according to claim 1 wherein the somatostatin receptor ligand is chelated to a radioactive atom.

5. The somatostatin receptor ligand, or a salt thereof according to claim 4 wherein the radioactive atom is atoms selected from the group consisting of technetium-99m, chromium-51, cobalt-57, cobalt-58, erbium-169, gallium-67, gallium-68, indium-111, iron-59, radium-223, rubidium-82, samarium-153, selenium-75, strontium-89, thallium-201 and yttrium-90.

6. A method for determining presence of a somatostatin receptor in a human comprising administering the somatostatin receptor ligand, or a salt thereof according to claim 1; and imaging the human.

7. The method according to claim 6 wherein the imaging is magnetic resonance imaging.

8. The method according to claim 7 wherein the metal atom is gadolinium.

9. The method according to claim 6 wherein the imaging is positron emission tomography (PET).

10. The method according to claim 9 wherein the radioactive atom is: Gallium-68.

11. The method according to claim 6 wherein the imaging is single-photon emission computerized tomography (SPECT).

12. The method according to claim 11 wherein the radioactive atom is iodine-123, iodine-131, or indium-111.

13. A pharmaceutical composition comprising a somatostatin receptor ligand, or a salt thereof according to claim 1 and a pharmaceutically acceptable carrier.

* * * * *

SEQUENCE LISTING

```
<160> NUMBER OF SEQ ID NOS: 70

<210> SEQ ID NO 1
<211> LENGTH: 116
<212> TYPE: PRT
<213> ORGANISM: HOMO_SAPIENS

<400> SEQUENCE: 1

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
                20                  25                  30

Gln Phe Leu Gln Lys Ser Leu Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
                100                 105                 110

Phe Thr Ser Cys
        115

<210> SEQ ID NO 2
<211> LENGTH: 14
<212> TYPE: PRT
<213> ORGANISM: HOMO_SAPIENS

<400> SEQUENCE: 2

Ala Gly Cys Lys Asn Phe Phe Trp Lys Thr Phe Thr Ser Cys
1               5                   10

<210> SEQ ID NO 3
<211> LENGTH: 28
<212> TYPE: PRT
<213> ORGANISM: HOMO_SAPIENS

<400> SEQUENCE: 3
```

-continued

```
Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 4
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-naphthylalanine (D-Nal)
<220> FEATURE:
<221> NAME/KEY: DISULFID
<222> LOCATION: (2)..(7)

<400> SEQUENCE: 4

Xaa Cys Tyr Trp Lys Val Cys Thr
1               5

<210> SEQ ID NO 5
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: DISULFID
<222> LOCATION: (2)..(7)
<220> FEATURE:
<221> NAME/KEY: MOD_RES
<222> LOCATION: (4)..(4)
<223> OTHER INFORMATION: D-tryptophan
<220> FEATURE:
<221> NAME/KEY: MOD_RES
<222> LOCATION: (8)..(8)
<223> OTHER INFORMATION: L-threoninol

<400> SEQUENCE: 5

Xaa Cys Phe Xaa Lys Thr Cys Xaa
1               5

<210> SEQ ID NO 6
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MISC_FEATURE
<222> LOCATION: (1)..(1)
<223> OTHER INFORMATION: FITC-GABA covalently attached to D-Phe at
      position 1
<220> FEATURE:
<221> NAME/KEY: MISC_FEATURE
<222> LOCATION: (1)..(1)
<223> OTHER INFORMATION: Optional FITC-GABA covalently attached to D-
      Phe at position 1
<220> FEATURE:
<221> NAME/KEY: DISULFID
<222> LOCATION: (2)..(9)
```

```
<220> FEATURE:
<221> NAME/KEY: MOD_RES
<222> LOCATION: (5)..(5)
<223> OTHER INFORMATION: D-tryptophan
<220> FEATURE:
<221> NAME/KEY: MOD_RES
<222> LOCATION: (9)..(9)
<223> OTHER INFORMATION: N-Thioethyl glycine

<400> SEQUENCE: 6

Xaa Cys Phe Trp Xaa Lys Thr Phe Xaa
1               5

<210> SEQ ID NO 7
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: selected from the group consisting of Phe and
      Tyr
<220> FEATURE:
<221> NAME/KEY: MISC_FEATURE
<222> LOCATION: (1)..(4)
<223> OTHER INFORMATION: at least one of: X at position 1 is Tyr,  X at
      position 2 is present or absent but if present is Phe, X at
      position 4 is other than Lys
<220> FEATURE:
<221> NAME/KEY: MISC_FEATURE
<222> LOCATION: (2)..(2)
<223> OTHER INFORMATION: present or absent and if present is selected
      from the group consisting of Trp and Phe
<220> FEATURE:
<221> NAME/KEY: MOD_RES
<222> LOCATION: (3)..(3)
<223> OTHER INFORMATION: D-tryptophan
<220> FEATURE:
<221> NAME/KEY: MISC_FEATURE
<222> LOCATION: (4)..(4)
<223> OTHER INFORMATION: group consisting of amino acid residues having
      a side chain with at least one nitrogen atom
<220> FEATURE:
<221> NAME/KEY: MISC_FEATURE
<222> LOCATION: (6)..(6)
<223> OTHER INFORMATION: "A" a chemical entity covalently attached to
      Phe

<400> SEQUENCE: 7

Xaa Xaa Xaa Xaa Thr Phe
1               5

<210> SEQ ID NO 8
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: selected from the group consisting of Phe and
      Tyr
<220> FEATURE:
<221> NAME/KEY: MISC_FEATURE
<222> LOCATION: (2)..(5)
<223> OTHER INFORMATION: at least one of: X at position 2 is Tyr,  X at
      position 3 is present or absent but if present is Phe, X at
      position 5 is other than Lys
<220> FEATURE:
<221> NAME/KEY: MISC_FEATURE
<222> LOCATION: (3)..(3)
<223> OTHER INFORMATION: s present or absent and if present is selected
```

```
        from the group consisting of Trp and Phe
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: MISC_FEATURE
<222> LOCATION: (5)..(5)
<223> OTHER INFORMATION: selected from the group consisting of amino
        acid residues having a side chain with at least one nitrogen atom
<220> FEATURE:
<221> NAME/KEY: MISC_FEATURE
<222> LOCATION: (7)..(7)
<223> OTHER INFORMATION: "A" a chemical entity covalently attached to
        Phe

<400> SEQUENCE: 8

Arg Xaa Xaa Xaa Xaa Thr Phe
1               5

<210> SEQ ID NO 9
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X is selected from HomoCysteine and D-Cysteine
<220> FEATURE:
<221> NAME/KEY: MOD_RES
<222> LOCATION: (1)..(1)
<223> OTHER INFORMATION: X is selected from GlyS2, Cys, HomoCysteine
        and D-Cysteine
<220> FEATURE:
<221> NAME/KEY: MOD_RES
<222> LOCATION: (1)..(1)
<223> OTHER INFORMATION: X is selected from Cysteine, HomoCysteine and
        D-Cysteine.
<220> FEATURE:
<221> NAME/KEY: MISC_FEATURE
<222> LOCATION: (2)..(2)
<223> OTHER INFORMATION: X is present or absent but if present is Arg
<220> FEATURE:
<221> NAME/KEY: MISC_FEATURE
<222> LOCATION: (3)..(3)
<223> OTHER INFORMATION: selected from the group consisting of Phe and
        Tyr
<220> FEATURE:
<221> NAME/KEY: MISC_FEATURE
<222> LOCATION: (4)..(4)
<223> OTHER INFORMATION: X present or absent and if present is selected
        from the group consisting of Trp and Phe
<220> FEATURE:
<221> NAME/KEY: MOD_RES
<222> LOCATION: (5)..(5)
<223> OTHER INFORMATION: D-tryptophan
<220> FEATURE:
<221> NAME/KEY: MISC_FEATURE
<222> LOCATION: (6)..(6)
<223> OTHER INFORMATION: X is selected from the group consisting of
        amino acid residues having a side chain with at least one
        nitrogen atom
<220> FEATURE:
<221> NAME/KEY: MISC_FEATURE
<222> LOCATION: (8)..(8)
<223> OTHER INFORMATION: "A" is a chemical entity covalently attached
        to Phe

<400> SEQUENCE: 9

Xaa Xaa Xaa Xaa Xaa Xaa Thr Phe
1               5

<210> SEQ ID NO 10
```

```
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: X selected from the group consisting of
      HomoCysteine and D-Cysteine
<220> FEATURE:
<221> NAME/KEY: MISC_FEATURE
<222> LOCATION: (3)..(3)
<223> OTHER INFORMATION: X is present or absent but if present is Arg
<220> FEATURE:
<221> NAME/KEY: MISC_FEATURE
<222> LOCATION: (4)..(4)
<223> OTHER INFORMATION: X is selected from the group consisting of Phe
      and Tyr
<220> FEATURE:
<221> NAME/KEY: MISC_FEATURE
<222> LOCATION: (5)..(5)
<223> OTHER INFORMATION: X is present or absent and if present is
      selected from the group consisting of Trp and Phe
<220> FEATURE:
<221> NAME/KEY: MOD_RES
<222> LOCATION: (6)..(6)
<223> OTHER INFORMATION: X is D-tryptophan
<220> FEATURE:
<221> NAME/KEY: MISC_FEATURE
<222> LOCATION: (7)..(7)
<223> OTHER INFORMATION: X is selected from the group consisting of
      amino acid residues having a side chain with at least one
      nitrogen atom
<220> FEATURE:
<221> NAME/KEY: MISC_FEATURE
<222> LOCATION: (9)..(9)
<223> OTHER INFORMATION: A chemical entity covalently bound to Phe

<400> SEQUENCE: 10

Arg Xaa Xaa Xaa Xaa Xaa Xaa Thr Phe
1               5

<210> SEQ ID NO 11
<211> LENGTH: 10
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: X is present or absent and if present is Arg
<220> FEATURE:
<221> NAME/KEY: MOD_RES
<222> LOCATION: (3)..(3)
<223> OTHER INFORMATION: X is selected from the group consisting of
      HomoCysteine and D-Cysteine
<220> FEATURE:
<221> NAME/KEY: MISC_FEATURE
<222> LOCATION: (4)..(4)
<223> OTHER INFORMATION: X is present or absent and if present is Arg
<220> FEATURE:
<221> NAME/KEY: MISC_FEATURE
<222> LOCATION: (5)..(5)
<223> OTHER INFORMATION: X is selected from the group consisting of Phe
      and Tyr
<220> FEATURE:
<221> NAME/KEY: MISC_FEATURE
<222> LOCATION: (6)..(6)
<223> OTHER INFORMATION: X is present or absent and if present is
      selected from the group consisting of Trp and Phe
<220> FEATURE:
```

```
<221> NAME/KEY: MOD_RES
<222> LOCATION: (7)..(7)
<223> OTHER INFORMATION: D-tryptophan
<220> FEATURE:
<221> NAME/KEY: MISC_FEATURE
<222> LOCATION: (8)..(8)
<223> OTHER INFORMATION: X is selected from the group consisting of
      amino acid residues having a side chain with at least one
      nitrogen atom
<220> FEATURE:
<221> NAME/KEY: BINDING
<222> LOCATION: (10)..(10)
<223> OTHER INFORMATION: A chemical entity covalently bound to Phe
<220> FEATURE:
<221> NAME/KEY: MISC_FEATURE
<222> LOCATION: (10)..(10)
<223> OTHER INFORMATION: A chemical entity covalently bound to Phe

<400> SEQUENCE: 11

Xaa Xaa Xaa Xaa Xaa Xaa Xaa Xaa Thr Phe
1               5                   10

<210> SEQ ID NO 12
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe at position 1
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (3)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MISC_FEATURE
<222> LOCATION: (9)..(9)
<223> OTHER INFORMATION: N-Thioethyl glycine

<400> SEQUENCE: 12

Xaa Arg Cys Phe Xaa Lys Thr Phe Xaa
1               5

<210> SEQ ID NO 13
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-tryptophan
<220> FEATURE:
<221> NAME/KEY: BINDING
<222> LOCATION: (5)..(5)
<223> OTHER INFORMATION: "A" is a chemical entity covalently attached
      to Phe

<400> SEQUENCE: 13

Phe Xaa Lys Thr Phe
1               5
```

```
<210> SEQ ID NO 14
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-tryptophan
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 14

Cys Phe Xaa Lys Thr Phe
1               5

<210> SEQ ID NO 15
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-tryptophan
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 15

Arg Cys Phe Xaa Lys Thr Phe
1               5

<210> SEQ ID NO 16
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-phenylalanine
<220> FEATURE:
<221> NAME/KEY: MOD_RES
<222> LOCATION: (5)..(5)
<223> OTHER INFORMATION: D-tryptophan
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 16

Xaa Arg Cys Phe Xaa Lys Thr Phe
1               5

<210> SEQ ID NO 17
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: Active agent Z or FITC-GABA covalently
      attached to D-Phe
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: Ornithine
<220> FEATURE:
<221> NAME/KEY: MOD_RES
<222> LOCATION: (9)..(9)
<223> OTHER INFORMATION: N-Thioethyl glycine

<400> SEQUENCE: 17

Xaa Cys Phe Trp Xaa Xaa Thr Phe Xaa
1               5

<210> SEQ ID NO 18
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-tryptophan
<220> FEATURE:
<221> NAME/KEY: MOD_RES
<222> LOCATION: (4)..(4)
<223> OTHER INFORMATION: Ornithine
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 18

Phe Trp Xaa Xaa Thr Phe
1               5

<210> SEQ ID NO 19
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: MOD_RES
<222> LOCATION: (5)..(5)
<223> OTHER INFORMATION: Ornithine
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 19

Cys Phe Trp Xaa Xaa Thr Phe
1               5
```

```
<210> SEQ ID NO 20
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: Ornithine
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 20

Xaa Cys Phe Trp Xaa Xaa Thr Phe
1               5

<210> SEQ ID NO 21
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (9)..(9)
<223> OTHER INFORMATION: N-Thioethyl glycine

<400> SEQUENCE: 21

Xaa Cys Tyr Trp Xaa Lys Thr Phe Xaa
1               5

<210> SEQ ID NO 22
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Tryptophan
<220> FEATURE:
<221> NAME/KEY: misc_feature
<222> LOCATION: (3)..(3)
<223> OTHER INFORMATION: Xaa can be any naturally occurring amino acid
<220> FEATURE:
```

```
<221> NAME/KEY: BINDING
<222> LOCATION: (6)..(6)
<223> OTHER INFORMATION: "A" is a chemical entity covalently attached
      to Phe

<400> SEQUENCE: 22

Tyr Trp Xaa Lys Thr Phe
1               5

<210> SEQ ID NO 23
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 23

Cys Tyr Trp Xaa Lys Thr Phe
1               5

<210> SEQ ID NO 24
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 24

Xaa Cys Tyr Trp Xaa Lys Thr Phe
1               5

<210> SEQ ID NO 25
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MISC_FEATURE
<222> LOCATION: (1)..(1)
<223> OTHER INFORMATION: Active agent Z or FITC-GABA covalently
      attached to DPhe
<220> FEATURE:
<221> NAME/KEY: MISC_FEATURE
<222> LOCATION: (1)..(1)
<223> OTHER INFORMATION: FITC-GABA covalently attached to D-Phe at
      position 1
```

```
<220> FEATURE:
<221> NAME/KEY: DISULFID
<222> LOCATION: (3)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: Ornithine
<220> FEATURE:
<221> NAME/KEY: MOD_RES
<222> LOCATION: (9)..(9)
<223> OTHER INFORMATION: N-Thioethyl glycine

<400> SEQUENCE: 25

Xaa Arg Cys Phe Xaa Xaa Thr Phe Xaa
1               5

<210> SEQ ID NO 26
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Phenylalanine
<220> FEATURE:
<221> NAME/KEY: MOD_RES
<222> LOCATION: (3)..(3)
<223> OTHER INFORMATION: Ornithine
<220> FEATURE:
<221> NAME/KEY: BINDING
<222> LOCATION: (5)..(5)
<223> OTHER INFORMATION: "A" is a chemical entity covalently attached
      to Phe

<400> SEQUENCE: 26

Phe Xaa Xaa Thr Phe
1               5

<210> SEQ ID NO 27
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Phenylalanine
<220> FEATURE:
<221> NAME/KEY: MOD_RES
<222> LOCATION: (4)..(4)
<223> OTHER INFORMATION: Ornithine
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 27

Cys Phe Xaa Xaa Thr Phe
1               5

<210> SEQ ID NO 28
<211> LENGTH: 7
<212> TYPE: PRT
<213> ORGANISM: ARTIFICIAL
<220> FEATURE:
```

```
<223> OTHER INFORMATION: Synthetic peptide
<220> FEATURE:
<221> NAME/KEY: MOD_RES
<222> LOCATION: (4)..(4)
<223> OTHER INFORMATION: D-Phenylalanine
<220> FEATURE:
<221> NAME/KEY: MOD_RES
<222> LOCATION: (5)..(5)
<223> OTHER INFORMATION: Ornithine
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 28

Arg Cys Phe Xaa Xaa Thr Phe
1               5

<210> SEQ ID NO 29
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: Ornithine
<220> FEATURE:
<221> NAME/KEY: MOD_RES
<222> LOCATION: (8)..(8)
<223> OTHER INFORMATION: "A" is a chemical entity covalently attached
      to Phe

<400> SEQUENCE: 29

Xaa Arg Cys Phe Xaa Xaa Thr Phe
1               5

<210> SEQ ID NO 30
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MISC_FEATURE
<222> LOCATION: (1)..(1)
<223> OTHER INFORMATION: Active agent Z or FITC-GABA covalently
      attached to DPhe
<220> FEATURE:
<221> NAME/KEY: MISC_FEATURE
<222> LOCATION: (1)..(1)
<223> OTHER INFORMATION: FITC-GABA covalently attached to D-Phe at
      position 1
<220> FEATURE:
<221> NAME/KEY: DISULFID
<222> LOCATION: (3)..(9)
<220> FEATURE:
<221> NAME/KEY: MOD_RES
<222> LOCATION: (5)..(5)
<223> OTHER INFORMATION: D-Tryptophan
<220> FEATURE:
```

```
<221> NAME/KEY: MOD_RES
<222> LOCATION: (9)..(9)
<223> OTHER INFORMATION: N-Thioethyl glycine

<400> SEQUENCE: 30

Xaa Arg Cys Tyr Xaa Lys Thr Phe Xaa
1               5

<210> SEQ ID NO 31
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Tryptophan
<220> FEATURE:
<221> NAME/KEY: BINDING
<222> LOCATION: (5)..(5)
<223> OTHER INFORMATION: "A" is a chemical entity covalently attached
      to Phe

<400> SEQUENCE: 31

Tyr Xaa Lys Thr Phe
1               5

<210> SEQ ID NO 32
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Phenylalanine
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 32

Cys Tyr Xaa Lys Thr Phe
1               5

<210> SEQ ID NO 33
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 33

Arg Cys Tyr Xaa Lys Thr Phe
1               5

<210> SEQ ID NO 34
<211> LENGTH: 8
<212> TYPE: PRT
```

```
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 34

Xaa Arg Cys Tyr Xaa Lys Thr Phe
1               5

<210> SEQ ID NO 35
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to DPhe
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (2)..(8)
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (8)..(8)
<223> OTHER INFORMATION: N-Thioethyl glycine

<400> SEQUENCE: 35

Xaa Cys Tyr Xaa Xaa Thr Phe Xaa
1               5

<210> SEQ ID NO 36
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Tryptophan
<220> FEATURE:
<221> NAME/KEY: MOD_RES
<222> LOCATION: (3)..(3)
<223> OTHER INFORMATION: Ornithine
<220> FEATURE:
<221> NAME/KEY: BINDING
<222> LOCATION: (5)..(5)
<223> OTHER INFORMATION: "A" is a chemical entity covalently attached
      to Phe
```

<400> SEQUENCE: 36

Tyr Xaa Xaa Thr Phe
1               5

<210> SEQ ID NO 37
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Tryptophan
<220> FEATURE:
<221> NAME/KEY: MOD_RES
<222> LOCATION: (4)..(4)
<223> OTHER INFORMATION: Ornithine
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 37

Cys Tyr Xaa Xaa Thr Phe
1               5

<210> SEQ ID NO 38
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: MOD_RES
<222> LOCATION: (5)..(5)
<223> OTHER INFORMATION: Ornithine
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 38

Xaa Cys Tyr Xaa Xaa Thr Phe
1               5

<210> SEQ ID NO 39
<211> LENGTH: 10
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to DPhe
<220> FEATURE:
<221> NAME/KEY: MOD_RES
<222> LOCATION: (1)..(1)
<223> OTHER INFORMATION: D-Phenylalanine
<220> FEATURE:

```
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: D-Tryptophan
<220> FEATURE:
<221> NAME/KEY: MOD_RES
<222> LOCATION: (10)..(10)
<223> OTHER INFORMATION: N-Thioethyl glycine

<400> SEQUENCE: 39

Xaa Cys Arg Phe Phe Xaa Lys Thr Phe Xaa
 1               5                  10

<210> SEQ ID NO 40
<211> LENGTH: 5
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Tryptophan
<220> FEATURE:
<221> NAME/KEY: BINDING
<222> LOCATION: (5)..(5)
<223> OTHER INFORMATION: "A" is a chemical entity covalently attached
      to Phe

<400> SEQUENCE: 40

Phe Xaa Lys Thr Phe
 1               5

<210> SEQ ID NO 41
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Tryptophan
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 41

Phe Phe Xaa Lys Thr Phe
 1               5

<210> SEQ ID NO 42
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Tryptophan
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: BINDING
<222> LOCATION: (7)..(7)
<223> OTHER INFORMATION: "A" is a chemical entity covalently attached
```

```
              to Phe

<400> SEQUENCE: 42

Arg Phe Phe Xaa Lys Thr Phe
1               5

<210> SEQ ID NO 43
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 43

Cys Arg Phe Phe Xaa Lys Thr Phe
1               5

<210> SEQ ID NO 44
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (6)..(6)
<223> OTHER INFORMATION: D-Tryptophan
<220> FEATURE:
<221> NAME/KEY: BINDING
<222> LOCATION: (9)..(9)
<223> OTHER INFORMATION: "A" is a chemical entity covalently attached
      to Phe

<400> SEQUENCE: 44

Xaa Cys Arg Phe Phe Xaa Lys Thr Phe
1               5

<210> SEQ ID NO 45
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to Cys at position 1
<220> FEATURE:
<221> NAME/KEY: DISULFID
<222> LOCATION: (1)..(8)
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: MOD_RES
<222> LOCATION: (8)..(8)
<223> OTHER INFORMATION: N-Thioethyl glycine
```

<400> SEQUENCE: 45

Cys Arg Phe Xaa Lys Thr Phe Xaa
1               5

<210> SEQ ID NO 46
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to DPhe at position 1
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (9)..(9)
<223> OTHER INFORMATION: N-Thioethyl glycine

<400> SEQUENCE: 46

Xaa Cys Arg Phe Xaa Lys Thr Phe Xaa
1               5

<210> SEQ ID NO 47
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Tryptophan
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 47

Arg Phe Xaa Lys Thr Phe
1               5

<210> SEQ ID NO 48
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 48

```
Cys Arg Phe Xaa Lys Thr Phe
1               5
```

<210> SEQ ID NO 49
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 49

```
Xaa Cys Arg Phe Xaa Lys Thr Phe
1               5
```

<210> SEQ ID NO 50
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe at position 1
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (2)..(2)
<223> OTHER INFORMATION: HomoCysteine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (9)..(9)
<223> OTHER INFORMATION: N-Thioethyl glycine

<400> SEQUENCE: 50

```
Xaa Xaa Phe Trp Xaa Lys Thr Phe Xaa
1               5
```

<210> SEQ ID NO 51
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES

```
<222> LOCATION: (2)..(2)
<223> OTHER INFORMATION: Homocysteine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 51

Xaa Xaa Phe Trp Xaa Lys Thr Phe
1               5

<210> SEQ ID NO 52
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe at position 1
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (2)..(2)
<223> OTHER INFORMATION: D-Cysteine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (9)..(9)
<223> OTHER INFORMATION: N-Thioethyl glycine

<400> SEQUENCE: 52

Xaa Xaa Phe Trp Xaa Lys Thr Phe Xaa
1               5

<210> SEQ ID NO 53
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (2)..(2)
<223> OTHER INFORMATION: D-Cysteine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: BINDING
<222> LOCATION: (8)..(8)
<223> OTHER INFORMATION: "A" is a chemical entity covalently attached
      to Phe
```

```
<400> SEQUENCE: 53

Xaa Xaa Phe Trp Xaa Lys Thr Phe
1               5

<210> SEQ ID NO 54
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe at position 1
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: 2-Aminoisobutyric acid
<220> FEATURE:
<221> NAME/KEY: MOD_RES
<222> LOCATION: (9)..(9)
<223> OTHER INFORMATION: N-Thioethyl glycine

<400> SEQUENCE: 54

Phe Cys Phe Trp Xaa Xaa Thr Phe Xaa
1               5

<210> SEQ ID NO 55
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Phenylalanine
<220> FEATURE:
<221> NAME/KEY: MOD_RES
<222> LOCATION: (4)..(4)
<223> OTHER INFORMATION: 2-Aminoisobutyric acid
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 55

Phe Trp Xaa Xaa Thr Phe
1               5

<210> SEQ ID NO 56
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-Phenylalanine
```

```
<220> FEATURE:
<221> NAME/KEY: MOD_RES
<222> LOCATION: (5)..(5)
<223> OTHER INFORMATION: 2-Aminoisobutyric acid
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 56

Cys Phe Trp Xaa Xaa Thr Phe
1               5

<210> SEQ ID NO 57
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: 2-Aminoisobutyric acid
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 57

Xaa Cys Phe Trp Xaa Xaa Thr Phe
1               5

<210> SEQ ID NO 58
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe at position 1
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: acetyllysine
<220> FEATURE:
<221> NAME/KEY: MOD_RES
<222> LOCATION: (9)..(9)
<223> OTHER INFORMATION: N-Thioethyl glycine

<400> SEQUENCE: 58
```

```
Xaa Cys Phe Trp Xaa Xaa Thr Phe Xaa
1               5
```

<210> SEQ ID NO 59
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Tryptophan
<220> FEATURE:
<221> NAME/KEY: MOD_RES
<222> LOCATION: (4)..(4)
<223> OTHER INFORMATION: Acetyllysine
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 59

```
Phe Trp Xaa Xaa Thr Phe
1               5
```

<210> SEQ ID NO 60
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: MOD_RES
<222> LOCATION: (5)..(5)
<223> OTHER INFORMATION: Acetyllysine
<220> FEATURE:
<221> NAME/KEY: BINDING
<222> LOCATION: (5)..(5)
<223> OTHER INFORMATION: "A" is a chemical entity covalently attached
      to Phe

<400> SEQUENCE: 60

```
Cys Phe Trp Xaa Xaa Thr Phe
1               5
```

<210> SEQ ID NO 61
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: acetyllysine
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 61

Xaa Cys Phe Trp Xaa Xaa Thr Phe
1               5

<210> SEQ ID NO 62
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe at position 1
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (9)..(9)
<223> OTHER INFORMATION: N-Thioethyl glycine

<400> SEQUENCE: 62

Xaa Cys Phe Trp Xaa Arg Thr Phe Xaa
1               5

<210> SEQ ID NO 63
<211> LENGTH: 8
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 63

Xaa Cys Phe Trp Xaa Arg Thr Phe
1               5

<210> SEQ ID NO 64
<211> LENGTH: 9
<212> TYPE: PRT
<213> ORGANISM: ARTIFICIAL
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Active agent Z or FITC-GABA covalently
      attached to D-Phe at position 1
<220> FEATURE:
<221> NAME/KEY: MOD_RES

```
<222> LOCATION: (1)..(1)
<223> OTHER INFORMATION: D-Phenylalanine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: HomoLysine
<220> FEATURE:
<221> NAME/KEY: MOD_RES
<222> LOCATION: (9)..(9)
<223> OTHER INFORMATION: N-Thioethyl glycine

<400> SEQUENCE: 64

Xaa Cys Phe Trp Xaa Xaa Thr Phe Xaa
1               5

<210> SEQ ID NO 65
<211> LENGTH: 6
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: D-Tryptophan
<220> FEATURE:
<221> NAME/KEY: MOD_RES
<222> LOCATION: (4)..(4)
<223> OTHER INFORMATION: HomoLysine
<220> FEATURE:
<221> NAME/KEY: BINDING
<222> LOCATION: (6)..(6)
<223> OTHER INFORMATION: "A" is a chemical entity covalently attached
      to Phe

<400> SEQUENCE: 65

Phe Trp Xaa Xaa Thr Phe
1               5

<210> SEQ ID NO 66
<211> LENGTH: 7
<212> TYPE: PRT
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: D-Tryptophan
<220> FEATURE:
<221> NAME/KEY: MOD_RES
<222> LOCATION: (5)..(5)
<223> OTHER INFORMATION: HomoLysine
<220> FEATURE:
<221> NAME/KEY: BINDING
<222> LOCATION: (7)..(7)
<223> OTHER INFORMATION: "A" is a chemical entity covalently attached
      to Phe

<400> SEQUENCE: 66

Cys Phe Trp Xaa Xaa Thr Phe
1               5

<210> SEQ ID NO 67
<211> LENGTH: 8
<212> TYPE: PRT
```

```
<213> ORGANISM: ARTIFICIAL
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phenylalanine
<220> FEATURE:
<221> NAME/KEY: MOD_RES
<222> LOCATION: (5)..(5)
<223> OTHER INFORMATION: D-Tryptophan
<220> FEATURE:
<221> NAME/KEY: MOD_RES
<222> LOCATION: (6)..(6)
<223> OTHER INFORMATION: HomoLysine
<220> FEATURE:
<221> NAME/KEY: BINDING
<222> LOCATION: (8)..(8)
<223> OTHER INFORMATION: "A" is a chemical entity covalently attached
      to Phe

<400> SEQUENCE: 67

Xaa Cys Phe Trp Xaa Xaa Thr Phe
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(9)
<220> FEATURE:
<221> NAME/KEY: MISC_FEATURE
<222> LOCATION: (1)..(9)
<223> OTHER INFORMATION: B' is any chemical entity covalently bonded to
      the terminal amino group of the N-terminal amino acid residue
<220> FEATURE:
<221> NAME/KEY: MOD_RES
<222> LOCATION: (1)..(9)
<223> OTHER INFORMATION: Each of the residues may each by any naturally
      occuring or synthetic amino acid rediude with the proviso that
      the N-terminal amino acid and the C-terminal amino acids are
      amino acids which are capable of forming disulfide bonds, and at
      least one of the
<220> FEATURE:
<221> NAME/KEY: MOD_RES
<222> LOCATION: (2)..(8)
<223> OTHER INFORMATION: Peptide is 6-9 amino acid residues, therefore
      three of the seven internal residues are optionally present or
      absent.
<220> FEATURE:
<221> NAME/KEY: MOD_RES
<222> LOCATION: (4)..(7)
<223> OTHER INFORMATION: At least one of 4, 5, 6, 7 internal amino
      acids  includes a side chain functional group having a nitrogen
      atom (N) to which a nanoparticle active agent moiety is
      covalently attached (Q in Figure 13)
<220> FEATURE:
<221> NAME/KEY: MISC_FEATURE
<222> LOCATION: (9)..(9)
<223> OTHER INFORMATION: B is any chemical entity covalently bonded to
      the terminal carbonyl group of the C-terminal amino acid residue

<400> SEQUENCE: 68

Xaa Xaa Xaa Xaa Xaa Xaa Xaa Xaa Xaa
1               5

<210> SEQ ID NO 69
<211> LENGTH: 8
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: N-Thioethyl glycine
<220> FEATURE:
<221> NAME/KEY: DISULFID
<222> LOCATION: (1)..(8)
<220> FEATURE:
<221> NAME/KEY: MOD_RES
<222> LOCATION: (4)..(4)
<223> OTHER INFORMATION: D-tryptophan
<220> FEATURE:
<221> NAME/KEY: MOD_RES
<222> LOCATION: (8)..(8)
<223> OTHER INFORMATION: N-Thioethyl glycine

<400> SEQUENCE: 69

Xaa Phe Trp Xaa Lys Thr Phe Xaa
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-tryptophan
<220> FEATURE:
<221> NAME/KEY: MOD_RES
<222> LOCATION: (2)..(2)
<223> OTHER INFORMATION: N-Thioethyl glycine
<220> FEATURE:
<221> NAME/KEY: DISULFID
<222> LOCATION: (2)..(9)
<220> FEATURE:
<221> NAME/KEY: MOD_RES
<222> LOCATION: (5)..(5)
<223> OTHER INFORMATION: D-tryptophan
<220> FEATURE:
<221> NAME/KEY: MOD_RES
<222> LOCATION: (9)..(9)
<223> OTHER INFORMATION: N-Thioethyl glycine

<400> SEQUENCE: 70

Xaa Xaa Phe Trp Xaa Lys Thr Phe Xaa
1               5
```